United States Patent
Dai et al.

(10) Patent No.: US 6,235,786 B1
(45) Date of Patent: *May 22, 2001

(54) REVERSE HYDROXAMATE INHIBITORS OF MATRIX METALLOPROTEINASES

(75) Inventors: Yujia Dai, Gurnee; Steven K. Davidsen; Michael R. Michaelides, both of Livertyville, all of IL (US); Jamie R. Stacey, Racine, WI (US); Douglas H. Steinman, Morton Grove; Carol K. Wada, Gurnee, both of IL (US)

(73) Assignee: Abbott Laboratories, Abbott Park, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/492,718

(22) Filed: Jan. 27, 2000

Related U.S. Application Data

(63) Continuation-in-part of application No. 09/238,377, filed on Jan. 27, 1999, now abandoned, which is a continuation-in-part of application No. 09/129,360, filed on Aug. 5, 1998, now abandoned.
(60) Provisional application No. 60/055,103, filed on Aug. 6, 1997, now abandoned.

(51) Int. Cl.⁷ ..................... C07C 317/50; A61K 31/165
(52) U.S. Cl. ..................... 514/575; 548/319.5; 549/373; 562/621
(58) Field of Search ..................... 562/621; 514/575; 548/319.5; 549/373

(56) References Cited

U.S. PATENT DOCUMENTS

| | | | |
|---|---|---|---|
| 4,859,706 | 8/1989 | Buerstinghaus et al. | 514/624 |
| 4,981,865 | 1/1991 | Belliotti et al. | 514/480 |
| 5,605,923 | 2/1997 | Christensen, IV et al. | 514/417 |

FOREIGN PATENT DOCUMENTS

| | | |
|---|---|---|
| 0196184 | 3/1986 | (EP) . |
| 0780386 | 6/1997 | (EP) . |
| 9402448 | 2/1994 | (WO) . |
| 9533731 | 12/1995 | (WO) . |
| 9718188 | 5/1997 | (WO) . |
| 9838179 | 9/1998 | (WO) . |
| 9906361 | 2/1999 | (WO) . |

OTHER PUBLICATIONS

S.F. Wnuk, et al., "Nucleic Acid Related Compounds. 67.", *Canadian Journal of Chemistry*, vol. 69, No. 12, pp. 2104–2111.

Biochemistry, vol. 31 (1992), pp. 11231–11235, Ye et al., "Purification and Characterization of the Human Stromelysin Catalytic Domain Expressed in *Escherichia coli*".

Analytical Biochemistry, vol. 147 (1985), pp. 437–440, Weingarten et al., "Spectrophotometric Assay for Vertebrate Collagenase".

K. M. Mohler et al., "Protection against a lethal dose of endotoxin by an inhibitor of tumor necrosis factor processing", *Letters To Nature*, vol. 370, Jul. 21, 1994, pp. 218–220.

A.J. H. Gearing et al., Processing of tumor necrosis factor–α by metalloproteinases, *Letters To Nature*, vol. 370, Aug. 18, 1994, pp. 555–557.

G. M. McGeehan et al., "Regulation of tumor necrosis factorα processing by a metalloproteinase inhibitor", *Letters To Nature* vol. 370, Aug. 18, 1994, pp. 558–560.

S. M. Berge et al., "Pharmaceutical Salts", *Journal of Pharmaceutical Sciences*, vol. 66, No. 1, Jan. 1997, pp. 1–19.

T. Higuchi & V. Stella, "Pro–drugs as Novel Drug Delivery Systems", vol. 14 of the A.C.S. Symposium Series.

Edward B. Roche, ed., "Bioreversible Carriers in Drug Design—Theory and Application", *American Pharmaceutical Association and Pergamon Press*, 1987.

D. B. Dess et al., "A Useful 12–I–5 Triacetoxyperiodinane (the Dess–Martin Periodinane) for the Selective Oxidation of Primary or Secondary Alcohols and a Variety of Realted 12–I–5 Species", *J. Am. Chem. Soc.*, 1991, 113, 7277–7287.

Green, "Protective Groups min Organic Synthesis", John Wiley & Sons, New York (1981).

*Primary Examiner*—Robert Gerstl
(74) *Attorney, Agent, or Firm*—B. Gregory Donner; Gregory W. Steele

(57) ABSTRACT

Compounds having the formula

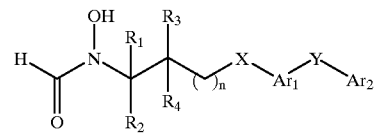

are matrix metalloproteinase inhibitors. Also disclosed are matrix metalloproteinase-inhibiting compositions and methods of inhibiting matrix metalloproteinase in a mammal.

13 Claims, No Drawings

REVERSE HYDROXAMATE INHIBITORS OF MATRIX METALLOPROTEINASES

CROSS REFERENCE TO RELATED APPLICATIONS

This application is a continuation-in-part of U.S. patent application Ser. No. 09/238,377, filed Jan. 27, 1999, abandoned which is a continuation-in-part of U.S. patent application Ser. No. 09/129,360, filed Aug. 5, 1998, abandoned, which is a continuation-in-part of provisional patent application Ser. No. 60/055,103, filed Aug. 6, 1997, abandoned.

TECHNICAL FIELD

This invention relates to compounds having activity to inhibit matrix metalloproteinases, to pharmaceutical compositions comprising these compounds and to a medical method of treatment. More particularly, this invention concerns reverse hydroxamate-containing compounds which inhibit matrix metalloproteinases, pharmaceutical compositions comprising these compounds and a method of inhibiting matrix metalloproteinases.

BACKGROUND OF THE INVENTION

The matrix metalloproteinases (MMP's) are a class of extracellular enzymes including collagenase, stromelysin, and gelatinase which are believed to be involved in the tissue destruction which accompanies a large number of disease states varying from arthritis to cancer.

Typical connective tissue cells are embedded within an extracellular matrix of high molecular weight proteins and glycoproteins. In healthy tissue, there is a continual and delicately-balanced series of processes which include cell division, matrix synthesis and matrix degradation. In certain pathological conditions, an imbalance of these three processes can lead to improper tissue restructuring. In arthritis, for example, joint mobility can be lost when there is improper remodeling of load-bearing joint cartilage. With cancer, lack of coordination of cell division and the two processes of matrix synthesis and degradation may lead to conversion of transformed cells to invasive phenotypes in which increased matrix turnover permits tumor cells to penetrate basement membranes surrounding capillaries which, in turn, may lead to subsequent metastasis.

There has been heightened interest in discovering therapeutic agents which bind to and inhibit MMP's. The discovery of new therapeutic agents possessing this activity will lead to new drugs having a novel mechanism of action for combating disease states involving tissue degenerative processes including, for Example, rheumatoid arthritis, osteoarthritis, osteopenias such as osteoporosis, periodontitis, gingivitis, corneal, epidermal or gastric ulceration, and tumor growth and metastasis or invasion.

SUMMARY OF THE INVENTION

In its principle embodiment, the present invention provides a matrix metalloproteinase inhibitory compound of formula (I),

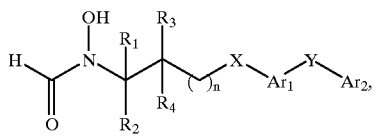

or a pharmaceutically acceptable salt or prodrug thereof, wherein n is zero;

$R^1$ is hydrogen;

$R^2$ and $R^4$ are independently selected from the group consisting of (1) hydrogen,
(2) alkyl,
(3) alkenyl,
(4) alkynyl,
(5) alkoxyalkyl,
(6) alkoxycarbonylalkyl,
(7) haloalkyl,
(8) hydroxyalkyl,
(9)-(alkylene)-$S(O)_p$-alkyl, wherein p is zero to two,
(10) phenyl,
(11) phenylalkoxyalkyl,
(12) phenylalkyl,
(13) phenoxyalkyl,
(14)-(alkylene)-$N(R_{20})SO_2$-phenyl, wherein $R_{20}$ is hydrogen or alkyl,
(15) (heterocycle)oxyalkyl,
(16)-(alkylene)-$S(O)_p$-heterocycle,
(17)-(alkylene)-heterocycle,
(18) heterocycle,
and
(19)-(alkylene)-$NR^6R^7$, wherein for (15)–(18), the heterocycle is selected from the group consisting of
(a) pyridyl,
(b) pyrazinyl,
(c) pyridazinyl,
(d) furyl,
(e) thienyl,
(f) isoxazolyl,
(g) oxazolyl,
(h) thiazolyl,
(i) isothiazolyl,

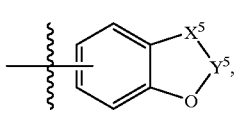

wherein $X^5$ is selected from the group consisting of —O—, —$NR^5SO_2$—, —$S(O)_p$—, and —C(O)—, and $Y^5$ is selected from the group consisting of a covalent bond, —O—, alkylene of two to four carbon atoms, piperidineneyl, alkenylene of two carbon atoms, alkynylene of two carbon atoms, —$S(O)_p$—, and —C(O)—,

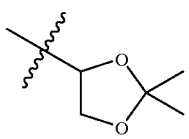
(k)

and wherein for (10)–(18), the phenyl and the phenyl part of the phenylalkoxyalkyl, the phenylalkyl, -the (alkylene)-N($R^{20}$)$SO_2$-phenyl, the phenoxyalkyl, and the -(alkylene)-S(O)$_p$-phenyl, the heterocycle, and the heterocycle part of the (heterocycle)oxyalkyl, the -(alkylene)-heterocycle and the -(alkylene)-S(O)$_p$-heterocycle are optionally substituted with one, two, or three substituents independently selected from the group consisting of
(a) alkyl,
(b) alkoxy,
(c) alkoxyalkyl,
(d) halo,
(e) haloalkyl,
(f) hydroxy,
(g) hydroxyalkyl,
(h) -(alkylene)-heterocycle,
(i) -(alkylene)-phenyl,
(j) —N($R^{20}$)$SO_2$-alkyl,
(k) phenyl, wherein the phenyl is optionally substituted with one, two, three, four, or five substituents independently selected from the group consisting of
(i) cyano,
(ii) nitro,
and
(iii) halo,
(l) —C(O)O$R^{20}$,
and
(m) —C(O)N$R^xR^y$, wherein $R^x$ and $R^y$ are independently selected from the group consisting of
(i) alkyl,
(ii) phenyl,
and
(iii) phenylalkyl,
wherein for (ii) and (iii), the phenyl and the phenyl part of phenylalkyl are optionally substituted with substituents independently selected from the group consisting of
(a) halo,
and
(b) alkoxy,
and wherein for (19), $R^6$ and $R^7$ are independently selected from the group consisting of
(a) hydrogen,
(b) alkyl,
(c) cycloalkyl,
(d) cycloalkylalkyl,
(e) alkanoyl,
(f) phenyl,
and
(g) phenylalkyl,
wherein for (f) and (g), the phenyl and the phenyl part of the phenylalkyl are optionally substituted with one or two substituents independently selected from the group consisting of
(i) alkyl,
(ii) alkoxy,
(iii) perfluoroalkyl,
(iv) halo,
(v) haloalkyl,
and
(vi) alkanoyl,
or
$R^6$ and $R^7$, taken together with the nitrogen atom to which they are attached, form a ring selected from the group consisting of
(a) morpholinyl,
(b) thiomorpholinyl,
(c) thiomorpholinyl sulfone,
(d) pyrrolidinyl,
(e) piperazinyl,
(f) piperidinyl,
(g) succinimidyl,
(h) maleimidyl,
(i) glutarimidyl,
(j) phthalimidyl,
(k) naphthalimidyl,

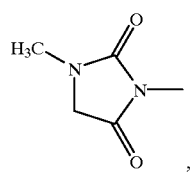
(l)

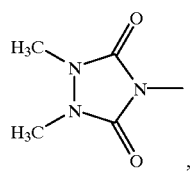
(m)

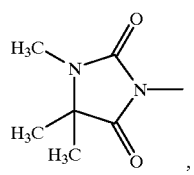
(n)

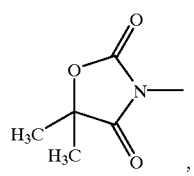
(o)

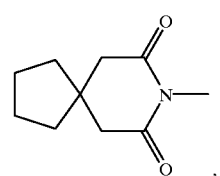
(p)

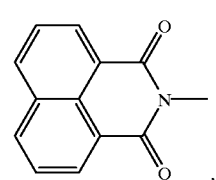
(q)

-continued

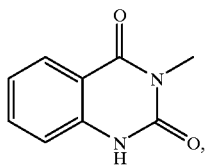
(r)

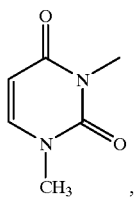
(s)

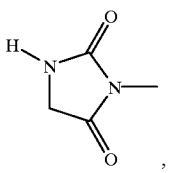
(t)

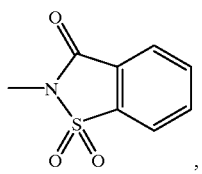
(u)

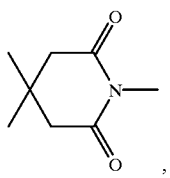
and

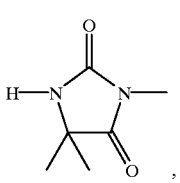
(w)

wherein for (a)–(w), the groups defined by $R^6$ and $R^7$, together with the nitrogen atom to which they are attached, are optionally substituted with one or two substituents independently selected from the group consisting of
(i) halo,
(iii) alkyl,
(iii) alkoxy,
(iv) phenoxy,
(v) phenylalkyl,
and
(vi) benzyloxy;
$R^3$ is selected from the group consisting of
(1) hydrogen,
(2) alkyl,
and
(3) hydroxyalkyl;

or
(r) $R^3$ and $R^4$, taken together with the carbon atom to which they are attached, form a dioxanyl ring;
or
$R^2$ and $R^3$ taken together with the carbon atoms to which they are attached form a 5, 6, or 7-membered saturated carbocyclic ring;
$Ar^1$ is phenyl, wherein the phenyl can be optionally substituted with one or two substituents independently selected from the group consisting of
(1) alkyl,
(2) perfluoroalkyl,
(3) halo,
(4) haloalkyl,
(5) alkoxy,
(6) hydroxy,
(7) hydroxyalkyl,
(8) alkoxyalkyl,
and
(9) nitro;
X is selected from the group consisting of
(1) —CH$_2$SO$_2$—,
(2) —SO$_2$—,
and
(3) —NR$^8$SO$_2$—, wherein $R^8$ is either hydrogen or alkyl;
wherein each group is drawn with its left-hand end being the end which attaches to the carbon containing $R^3$ and $R^4$, and its right-hand end being the end which attaches to $Ar^1$;
Y is selected from the group consisting of
(1) a covalent bond,
(2) —O—,
(3) alkylene-of two to four carbon atoms,
(4) piperidineneyl,
(5) alkenylene of two carbon atoms,
(6) alkynylene of two carbon atoms,
(7) —SO$_2$—,
(8) —NHC(O)—,
and
(9) —C(O)—;
$Ar^2$ is selected from the group consisting of
(1) phenyl,
(2) pyridyl,
(3) pyrazinyl,
(4) pyridazinyl,
(5) furyl,
(6) thienyl,
(7) isoxazolyl,
(8) oxazolyl,
(9) thiazolyl,
and
(10) isothiazolyl,
wherein (1)–(10) can be optionally substituted with one, two, or three substituents independently selected from the group consisting of
(a) alkyl,
(b))alkoxy, wherein the alkoxy can be optionally substituted with alkoxy,
(c) -(alkylene)-CO$_2$R$^8$,
(d) -(alkylene)-NR$^9$R$^{10}$, wherein $R^9$ and $R^{10}$ are independently selected from the group consisting of (i) alkyl,
(ii) phenyl,
and
(iii) phenylalkyl,
wherein for (ii) and (iii), the phenyl and the phenyl part of the phenylalkyl can be optionally substituted with one or two substituents independently selected from the group consisting of halo and alkoxy,
(e) alkoxyalkyl,
(f) cyano,
(g) cyanoalkyl,
(h) halo,
(i) haloalkyl,
(j) hydroxy,
(k) hydroxyalkyl,
(l) thioalkoxy,
(m) thioalkoxyalkyl,
(n) phenylalkoxy,
(o) phenoxy,
(p) phenoxyalkyl,
(q) (heterocycle)oxy,
(r) (heterocycle)oxyalkyl,
(s) perfluoroalkyl,
(t) perfluoroalkoxy,
(u) sulfinylalkyl,
(v) sulfonylalkyl,

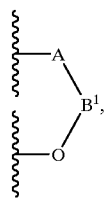

(w)

wherein A is selected from the group consisting of —CH$_2$—, CH$_2$O— and —O—, and B$^1$ is selected from the group consisting of —C(O)— and —(C(R")$_2$)$_v$—, wherein R" is either hydrogen or alkyl, and v is 1–3,
and
(x) —N(R$^8$)SO$_2$R$^{11}$, wherein R$^{11}$ is selected from the group consisting of
(i) hydrogen,
(ii) alkyl,
and
(iii) —N(R$^8$)(R$^{12}$), wherein R$^{11}$ is hydrogen or alkyl,
wherein for (q) and (r), the heterocycle part of (heterocycle)oxy, and (heterocycle)oxyalkyl are selected from the group consisting of
(i) pyridyl,
(ii) pyrazinyl,
(iii) pyridazinyl,
(iv) furyl,
(v) thienyl,
(vi) isoxazolyl,
(vii) oxazolyl,
(viii) thiazoloyl,
and
(ix) isothiazolyl,
and wherein for (q) and (r), the heterocycle part of the (heterocycle)oxy and the (heterocycle)oxyalkyl can be optionally substituted with one or two substituents independently selected from the group consisting of (i) alkyl,
(ii) alkoxy,
(iii) perfluoroalkyl,
(iv) halo,
(v) cyano,
(vi) cyanoalkyl,
(vii) haloalkyl,
and
(viii) alkanoyl,
and
wherein for (o) and (p), the phenyl part of the phenoxy and the phenoxyalkyl can be optionally substituted with one or two substituents independently selected from the group consisting of
(i) alkyl,
(ii) alkoxy,
(iii) perfluoroalkyl,
(iv) halo,
(v) cyano,
(vi) cyanoalkyl,
(vii) haloalkyl,
and
(viii) alkanoyl.

In another embodiment, the present invention provides pharmaceutical compositions which comprise a therapeutically effective amount of compound of formula I in combination with a pharmaceutically acceptable carrier.

In yet another embodiment, the present invention provides a method of inhibiting matrix metalloproteinases in a host mammal in recognized need of such treatment comprising administering to a mammal in need of such treatment a therapeutically effective amount of a compound of formula I.

DETAILED DESCRIPTION OF THE INVENTION

Definition of Terms

As used throughout this specification and the appended claims, the following terms have the meanings specified:

The term "alkyl," as used herein, represents a monovalent group derived from a straight or branched chain saturated hydrocarbon by the removal of a single hydrogen atom and is exemplified by methyl, ethyl, n- and iso-propyl, n-, sec-, iso-, and tert-butyl, neopentyl, and the like. The alkyl groups of this invention can be optionally substituted.

The term "alkanoyl," as used herein, represents an alkyl group, as defined above, attached to the parent molecular group through a carbonyl group and is exemplified by formyl, acetyl, propionyl, butanoyl, and the like. The alkanoyl groups of this invention can be optionally substituted.

The term "alkenyl," as used herein, represents monovalent straight or branched chain groups containing a carbon—carbon double bond derived from an alkene by the removal of one hydrogen atom and is exemplified by ethenyl, 1-propenyl, 2-propenyl, 2-methyl-1-propenyl, 1-butenyl, 2-butenyl, and the like. The alkenyl groups of this invention can be optionally substituted.

The term "alkoxy," as used herein, represents an alkyl group attached to the parent molecular group through an oxygen atom and is exemplified by methoxy, isopropoxy, tert-butoxy, and the like. The alkoxy groups of this invention can be optionally substituted.

The term "alkoxyalkyl" as used herein, represents an alkyl group to which is attached an alkoxy group. The alkoxyalkyl groups of this invention can be optionally substituted.

The term "alkoxycarbonyl," as used herein, represents an ester group, i.e. an alkoxy group attached to the parent molecular group through a carbonyl group, and is exemplified by methoxycarbonyl, ethoxycarbonyl, and the like. The alkoxycarbonyl groups of this invention can be optionally substituted.

The term "alkoxycarbonylalkyl," as used herein, represents an alkyl group, as defined above, substituted by a alkoxycarbonyl group. The alkoxycarbonylalkyl groups of this invention can be optionally substituted.

The term "alkylene," as used herein, represents a saturated divalent hydrocarbon group derived from a straight or branched chain saturated hydrocarbon by the removal of two hydrogen atoms and is exemplified by methyene, ethylene, isopropylene, and the like. The alkylene groups of this invention can be optionally substituted.

The term "alkynyl," as used herein, represents represents monovalent straight or branched chain groups of two to six carbon atoms containing a carbon—carbon triple bond derived from an alkyne by the removal of one hydrogen atom and is exemplified by ethynyl, 1-propynyl, and the like. The alkynyl groups of this invention can be optionally substituted.

The term "benzyloxy," as used herein, represents phenyl-(CH$_2$)—O—. The benzyloxy groups of this invention can be optionally substituted.

The term "carbocyclic," as used herein, represents a ring comprising 5,6, or 7 carbon atoms and zero doulbe bonds.

The term "cyano," as used herein, represents a —CN group.

The term "cyanoalkyl," as used herein, represents a cyano group attached to the parent molecular moiety through an alkyl group. The cyanoalkyl groups of this invention can be optionally substituted.

The term "cycloalkyl," as used herein represents a monovalent saturated cyclic hydrocarbon group and is exemplified by cyclopropyl, cyclobutyl, cyclopentyl, cyclohexyl, cycloheptyl, bicyclo(2.2.1)heptyl, and the like. The cycloalkyl groups of this invention can be optionally substituted.

The term "cycloalkylalkyl," as used herein, represents a cycloalkyl group attached to the parent molecular group through an alkylene group. The cycloalkylalkyl groups of this invention can be optionally substituted.

The term "dioxanyl," as used herein, represents {—(CH$_2$)—O—(CH$_2$)—O—(CH$_2$)—}, both carbons of which are attached to the same carbon atom of the parent group to form a cyclic moiety.

The term "halo," as used herein, represents F, Cl, Br, and I.

The term "haloalkyl," as used herein, represents an alkyl group substituted by one, two, three or four halogen atoms and is exemplified by chloromethyl, bromoethyl, chlorodifluoromethyl, and the like. The haloalkyl groups of this invention can be optionally substituted.

The term "heterocycle," as used herein, represents a five-, six- or seven-membered ring containing one, two or three heteroatoms independently selected from the group consisting of nitrogen, oxygen and sulfur. The five-membered ring has zero to two double bonds and the six- and seven-membered rings have zero to three double bonds. Hererocycles include indolyl, quinolyl, isoquinolyl, tetrahydroquinolyl, benzofuryl, benzothienyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiomorpholino sulfone, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, triazolyl, tetrazolyl, oxadiazolyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl, succinimidyl, maleimidyl, glutarimidyl, phthalimidyl, naphthalimidyl, and the like. The heterocycle groups of this invention can be optionally substituted.

Heterocycles also include 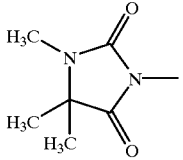 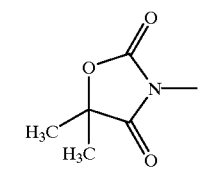,

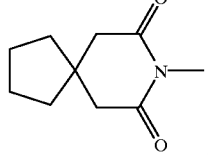 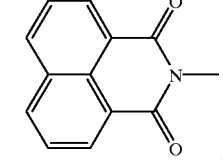,

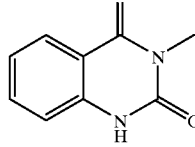 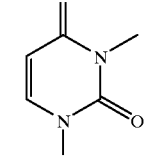,

 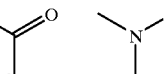,

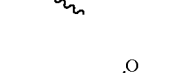 ,

 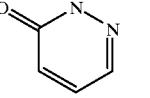,

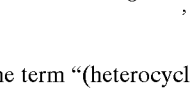 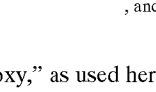, and the like.

The term "(heterocycle)oxy," as used herein, represents a heterocycle group attached to the parent molecular moiety through oxygen. The (heterocycle)oxy groups of this invention can be optionally substituted.

The term "(heterocycle)oxyalkyl," as used herein, represents a (heterocycle)oxy group attached to the parent molecular group through an alkyl group. The (heterocycle)oxyalkyl groups of this invention can be optionally substituted.

The term "hydroxy" as used herein, represents an —OH group.

The term "hydroxyalkyl," as used herein, represents an alkyl group, as defined above, substituted by one to three hydroxy groups, with the proviso that no more than one hydroxy group may be attached to a single carbon atom of the alkyl group and is exemplified by hydroxymethyl, dihydroxypropyl, and the like. The hydroxyalkyl groups of this invention can be optionally substituted.

The term "nitro," as used herein, refers to —NO$_2$.

The term "perfluoroalkyl," as used herein, represents an alkyl group, as defined herein, wherein each hydrogen radical bound to the alkyl group has been replaced by a fluoride radical. Perfluoroalkyl groups are exemplified by trifluoromethyl, pentafluoroethyl, and the like. The perfluoroalkyl groups of this invention can be optionally substituted.

The term "perfluoroalkoxy," as used herein, refers to a perfluoroalkyl group, as defined herein, attached to the parent molecular group through an oxygen atom. The perfluoroalkoxy groups of this invention can be optionally substituted.

The term "pharmaceutically acceptable salt," as use herein, represents those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well known in the art. For Example, S. M Berge, et al. describe pharmaceutically acceptable salts in detail in J. Pharmaceutical Sciences, 1977, 66:1–19. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "phenoxy," as used herein, represents a phenyl group attached to the parent molecular group through an oxygen atom. The phenoxy groups of this invention can be optionally substituted.

The term "phenoxyalkyl," as used herein, represents a phenoxy group attached to the parent molecular group through an alkyl group. The phenoxyalkyl groups of this invention can be optionally substituted.

The term "phenyl," as used herein, represents a 6-membered, monocyclic, aromatic carbocyclic ring. The phenyl groups of this invention can be optionally substituted.

The term "phenylalkyl," as used herein, represents an phenyl group attached to the parent molecular group through an alkylene group and is exemplified by benzyl, phenethyl, and the like. The phenylalkyl groups of this invention can be optionally substituted.

The term "phenylalkoxy," as used herein, represents a phenyl group attached to the parent molecular group through an alkoxy group. The phenylalkoxy groups of this invention can be optionally substituted.

The term "phenylalkoxyalkyl" as used herein, represents a phenylalkoxy group, as defined above, attached to the parent molecular group through an alkyl group. The phenylalkoxyalkyl groups of this invention can be optionally substituted.

The term "piperidineneyl," as used herein, represents a divalent group derived from piperidine by the removal of two hydrogen atoms. The piperidineneyl groups of this invention can be optionally substituted.

The term "prodrug," as used herein, represents compounds which are rapidly transformed in vivo to the parent compound of the above formula, for Example, by hydrolysis in blood. A thorough discussion is provided in T. Higuchi and V. Stella, *Pro-drugs as Novel Delivery Systems,* Vol. 14 of the A.C.S. Symposium Series, and in Edward B. Roche, ed., *Bioreversible Carriers in Drug Design,* American Pharmaceutical Association and Pergamon Press, 1987, both of which are incorporated herein by reference. Prodrugs of the compounds of the present invention are, within the scope of sound medical judgement, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "spiroalkyl," as used herein, represents an alkylene diradical, both ends of which are bonded to the same carbon atom of the parent group to form a spirocyclic group. The spiroalkyl groups of this invention can be optionally substituted.

The term "sulfinyl," as used herein, refers to an —S(O)— group.

The term "sulfinylalkyl," as used herein, refers to an alkyl group, as defined herein, attached to the parent mplecular group through a sulfinyl group.

The term "sulfonyl," as used herein, refers to an —SO$_2$— group.

The term "sulfonylalkyl," as used herein, refers to an alkyl group, as defined herein, attached to the parent mplecular group through a sulfonyl group. The sulfonylalkyl groups of this invention can be optionally substituted.

The term "thioalkoxy," as used herein, represents represents an alkyl group attached to the parent molecular group through a sulfur atom. The thioalkoxy groups of this invention can be optionally substituted.

Compounds of the present invention may exist as stereoisomers, wherein asymmetric or chiral centers are present. These compounds are designated by the symbols "R" or "S," depending on the configuration of subsitiuents around the chiral carbon atom. The present invention contemplates various stereoisomers and mixtures thereof. Stereoisomers include enantiomers and diastereomers, and mixtures of enantiomers or diastereomers are designated (±). Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Preferred Embodiments

Preferred compounds of the present invention have formula (I), wherein $R_3$, and $R_4$ are independently selected from the group consisting of
(1) hydrogen,
(2) alkyl of one to six carbon atoms, and
(3) hydroxyalkyl;
X is selected from the group consisting of
(1) —$SO_2$—,
(2) —$NR_8SO_2$—, wherein $R_8$ is hydrogen or alkyl,
(3) —$CH_2SO_2$—,
wherein (2) and (3) are drawn with the left-hand ends attached to the carbon bearing $R_3$ and $R_4$ and the right-hand ends attached to $Ar_1$; and
$Ar_1$ is phenyl which is optionally substituted.

More preferred compounds of the present invention have formula (I), wherein
$R_1$, $R_3$ and $R_4$ are H;
X is $CH_2SO_2$—;
$Ar_1$ is phenyl;

Preferred compounds falling within the scope of formula (I) include but are not limited to:

(±)-N-(1-(((4'-cyano-(1,1'-biphenyl)-4-yl)oxy)methyl)-2-phenoxyethyl)-N-hydroxyformamide;

(±)-N-(1-(((4'-cyano-(1,1'-biphenyl)-4-yl)oxy)methyl)-2-(phenylthio)ethyl)-N-hydroxyformamide;

(±)-N-(1-(((4'-cyano-(1,1'-biphenyl)-4-yl)oxy)methyl)-2-(2,3-dihydro-1,3-dioxo-1H-isoindol-2-yl)ethyl)-N-hydroxyformamide;

(±)-N-(1-(((4'-cyano-(1,1'-biphenyl)-4-yl)oxy)methyl)-2-(3,4,4-trimethyl-2,5-dioxoimidazolidin-1-yl)ethyl)-N-hydroxyformamide;

(±)-N-(1-(((4'-cyano-(1,1'-biphenyl)-4yl)oxy)methyl)-3-(3,4,4-trimethyl-2,5-dioxoimidazolidin-1-yl)propyl)-N-hydroxyformamide;

(±)-N-(1-(((3'-(cyanomethyl)-(1,1'-biphenyl)-4-yl)oxy)methyl)pentyl)-N-hydroxyformamide;

(±)-N-(1-(((4'-cyano-(1,1'-biphenyl)-4-yl)oxy)methyl)-3-methylbutyl)-N-hydroxyformamide;

(±)-N-(1-(((4'-cyano-(1,1'-biphenyl)-4yl)oxy)methyl)-2-methylbutyl)-N-hydroxyformamide;

(±)-N-(1-(((4'-cyano-(1,1'-biphenyl)-4-yl)oxy)methyl)pentyl)-N-hydroxyformamide;

(±)-N-(1-(((4'-cyano-(1,1'-biphenyl)-4-yl)oxy)methyl)-2-(4-methylphenyl)ethyl)-N-hydroxyformamide;

(±)-N-(2-((4'-cyano-(1,1'-biphenyl)-4-yl)oxy)-1-(4-fluorophenyl)ethyl)-N-hydroxyformamide;

(±)-N-(1-(((4'-cyano-(1,1'-biphenyl)-4-yl)oxy)methyl)-2-(4-fluorophenyl)ethyl)-N-hydroxyformamide;

(±)-N-(1-(((4'-cyano-(1,1'-biphenyl)-4-yl)oxy)methyl)ethyl)-N-hydroxyformamide;

(±)-N-(2-((4'-cyano-(1,1'-biphenyl)-4yl)oxy)ethyl)-N-hydroxyformamide;

(±)-N-(1-(4-((2E-phenylethenyl)phenoxy)methyl)-2-(3,4,4-trimethyl-2,5-dioxo-1-imidazolidinyl)ethyl)-N-hydroxyformamide;

(±)-N-(1-((4-(2-furanyl)phenoxy)methyl)-2-(3,4,4-trimethyl-2,5-dioxo-1-imidazolidinyl)ethyl)-N-hydroxyformamide;

(±)-N-(1-(((4'-butoxy(1,1'-biphenyl)-4-yl)oxy)methyl)-2-(3,4,4-trimethyl-2,5-dioxo-1-imidazolidinyl)ethyl)-N-hydroxyformamide;

(±)-N-(1-(((4'-fluoro(1,1'-biphenyl)-4-yl)oxy)methyl)-2-(3,4,4-trimethyl-2,5-dioxo-1-imidazolidinyl)ethyl)-N-hydroxyformamide;

(±)-N-(1-((3,4,4-trimethyl-2,5-dioxo-1-imidazolidinyl)methyl)-2-((4'-(trifluoromethyl)(1,1'-biphenyl)-4-yl)oxy)ethyl)-N-hydroxyformamide;

(±)-N-(1-(((4'-methoxy(1,1'-biphenyl)-4-yl)oxy)methyl)-2-(3,4,4-trimethyl-2,5-dioxo-1-imidazolidinyl)ethyl)-N-hydroxyformamide;

(±)-N-(1-(((4'-methyl(1,1'-biphenyl)-4-yl)oxy)methyl)-2-(3,4,4-trimethyl-2,5-dioxo-1-imidazolidinyl)ethyl)-N-hydroxyformamide;

(±)-N-(1-(((4'-butoxy(1,1'-biphenyl)-4-yl)oxy)methyl)-2-(4,4-dimethyl-2,5-dioxo-1-imidazolidinyl)ethyl)-N-hydroxyformamide;

(±)-N-(1-((4,4-dimethyl-2,5-dioxo-1-imidazolidinyl)methyl)-2-((4'-ethoxy(1,1'-biphenyl)-4-yl)oxy)ethyl)-N-hydroxyformamide;

(±)-N-(1-((4-(1,3-benzodioxol-5-yl)phenoxy)methyl)-2-(4,4-dimethyl-2,5-dioxo-1-imidazolidinyl)ethyl)-N-hydroxyformamide;

(±)-N-(1-(((4'-butoxy(1,1'-biphenyl)-4-yl)oxy)methyl)-2-(3-methyl-2,5-dioxo-1-imidazolidinyl)ethyl)-N-hydroxyformamide;

(±)-N-(1-((4-(3-thienyl)phenoxy)methyl)-2-(3,4,4-trimethyl-2,5-dioxo-1-imidazolidinyl)ethyl)-N-hydroxyformamide;

(±)-N-(1-((((1,1'-biphenyl)-4-yl)oxy)methyl)-2-(3,4,4-trimethyl-2,5-dioxo-1-imidazolidinyl)ethyl)-N-hydroxyformamide;

(±)-N-(1-(((3'-chloro-4'-fluoro(1,1'-biphenyl)-4-yl)oxy)methyl)-2-(3,4,4-trimethyl-2,5-dioxo-1-imidazolidinyl)ethyl)-N-hydroxyformamide;

(±)-N-(1-(((2'-methyl(1,1'-biphenyl)-4-yl)oxy)methyl)-2-(3,4,4-trimethyl-2,5-dioxo-1-imidazolidinyl)ethyl)-N-hydroxyformamide;

(±)-N-(1-(((4'-cyanol(1,1'-biphenyl)-4-yl)oxy)methyl)-2-(2,5-dioxo-1-imidazolidinyl)ethyl)-N-hydroxyformamide;

(±)-N-(1-(((4'-cyanol(1,1'-biphenyl)-4-yl)oxy)methyl)-2-(1,1-dioxido-3-oxo-1,2-benzisothiazol-2(3H)-yl)ethyl)-N-hydroxyformamide;

(±)-N-(1-((4,4-dimethyl-2,5-dioxo-1-imidazolidinyl)methyl)-2-((4'-(trifluoromethoxy)(1,1'-biphenyl)-4-yl)oxy)ethyl)-N-hydroxyformamide;

(±)-N-(1-((4-(4-phenyl-1-piperidinyl)phenoxy)methyl)-2-(3,4,4-trimethyl-2,5-dioxo-1-imidazolidinyl)ethyl)-N-hydroxyformamide;

(±)-N-(1-((4,4-dimethyl-2,5-dioxo-1-imidazolidinyl)methyl)-2-((4'-(trifluoromethyl)(1,1'-biphenyl)-4-yl)oxy)ethyl)-N-hydroxyformamide;

(±)-N-(1-(((3'-cyano(1,1'-biphenyl)-4-yl)oxy)methyl)-2-(methyl((4-methylphenyl)sulfonyl)amino)ethyl)-N-hydroxyformamide;

(±)-N-(1-(((4'-cyano(1,1'-biphenyl)-4-yl)oxy)methyl)-2-(4,4-dimethyl-2,5-dioxo-3-(3-pyridinylmethyl)-1-imidazolidinyl)ethyl)-N-hydroxyformamide;

(±)-N-(2-((4'-cyano(1,1'-biphenyl)-4yl)oxy)-1-methylpropyl)-N- hydroxyformamide;

(±)-N-(1-(((3'-cyano(1,1'-biphenyl)-4-yl)oxy)methyl)-2-(3,4,4-trimethyl-2,5-dioxo-1-imidazolidinyl)ethyl)-N-hydroxyformamide;

(±)-N-(1-(((4'-(methylthio)(1,1'-biphenyl)-4-yl)oxy)methyl)-2-(3,4,4-trimethyl-2,5-dioxo-1-imidazolidinyl)ethyl)-N-hydroxyformamide;

(±)-N-(1-(4-((4-(trifluoromethyl)phenoxy)phenoxy)methyl)-2-(3,4,4-trimethyl-2,5-dioxo-1-imidazolidinyl)ethyl)-N-hydroxyformamide;

(±)-N-(1-(((4'-(trifluoromethoxy)(1,1'-biphenyl)-4-yl)oxy)methyl)-2-(3,4,4-trimethyl-2,5-dioxo-1-imidazolidinyl)ethyl)-2-N-hydroxyformamide;

(±)-N-(1-(((4'-(methylsulfonyl)(1,1'-biphenyl)-4-yl)oxy)methyl)-2-(3,4,4-trimethyl-2,5-dioxo-1-imidazolidinyl)ethyl)-N-hydroxyformamide;

(±)-N-(1-(((3'-(cyanomethyl)-4'-methoxy(1,1'-biphenyl)-4-yl)oxy)methyl)-2-(3,4,4-trimethy-2,5dioxo-1-imidazolidinyl)ethyl)-N-hydroxyformamide;

(±)-N-(1-(((3'-(cyanomethyl)(1,1'-biphenyl)-4-yl)oxy)methyl)-3-(4,4-dimethyl-2,5-dioxo-1-imidazolidinyl)propyl))-N-hydroxyformamide;

(±)-N-(1-(((4'-butoxy(1,1'-biphenyl)-4-yl)sulfonyl)methyl)-2-(4,4-dimethyl-2,5-dioxo-1-imidazolidinyl)ethyl)-N-hydroxyformamide;

(±)-N-(1-(((4'-cyano(1,1'-biphenyl)-4-yl)oxy)methyl)-3-(4,4-dimethyl-2,5-dioxo-1-imidazolidinyl)propyl)-N-hydroxyformamide;

(±)-N-(1-(((4'-(methylsulfonyll)(1,1'-biphenyl)-4-yl)oxy)methyl)-2-(4,4-dimethyl-2,5-dioxo-1-imidazolidinyl)ethyl)-N-hydroxyformamide;

(±)-N-(1-(((3'-cyano(1,1'-biphenyl)-4-yl)oxy)methyl)-2-(2,5-dioxo-1-pyrrolidinyl)ethyl)-N-hydroxyformamide;

(±)-N-(1-(((4'-cyano(1,1'-biphenyl)-4-yl)oxy)methyl)-2-(4,4-dimethyl-2,6-dioxo-1-piperidinyl)ethyl)-N-hydroxyformamide;

(±)-N-(1S-(((4'-cyano(1,1'-biphenyl)-4-yl)oxy)methyl)-2-(2,5-dioxo-1-pyrrolidinyl)ethyl)-N-hydroxyformamide;

(±)-N-(1R-(((4'-cyano(1,1'-biphenyl)-4-yl)oxy)methyl)-2-(2,5-dioxo-1 -pyrrolidinyl)ethyl)-N-hydroxyformamide;

(±)-N-(1-(((4'-cyano(1,1'-biphenyl)-4-yl)oxy)methyl)-2-(3-ethyl-3-methyl-2,5-dioxo-1-pyrrolidinyl)ethyl)-N-hydroxyformamide;

N-(4-(4-(((4-chlorophenoxy)phenyl)sulfonyl)methyl)tetrahydro-2H-pyran-4-yl)-N-hydroxyformamide;

(±)-N-(1-(((4'-cyano(1,1'-biphenyl)-4-yl)oxy)methyl)-2-(((2-methoxycarbonyl)-phenyl)thio)ethyl)-N-hydroxyformamide;

(±)-N-(1-(((4'-cyano(1,1'-biphenyl)-4-yl)oxy)methyl)-5-((4-methyl-2-oxo-2H-1-benzopyran-6-yl)oxy)pentyl)-N-hydroxyformamide;

(±)-N-(1-(((4'-cyano(1,1'-biphenyl)-4-yl)oxy)methyl)-4-((4-methyl-2-oxo-2H-1-benzopyran-6-yl)oxy)butyl)-N-hydroxyformamide;

(±)-N-(1-(((4'-cyano(1,1'-biphenyl)-4-yl)oxy)methyl)-4-((4-methyl-2-oxo-2H-1-benzopyran-7-yl)oxy)butyl)-N-hydroxyformamide;

(±)-N-(1-(((4'-cyano(1,1'-biphenyl)-4-yl)oxy)methyl)-5-((4-methyl-2-oxo-2H-1-benzopyran-7-yl)oxy)pentyl)-N-hydroxyformamide;

(±)-N-(1-(((4'-cyano(1,1'-biphenyl)-4-yl)oxy)methyl)-2-(5,5-dimethyl-2,4-dioxo-3-oxazolidinyl)ethyl)-N-hydroxyformamide;

(±)-N-(1-(((4'-cyano(1,1'-biphenyl)-4-yl)sulfonyl)methyl)-2-(3,4,4-trimethy-2,5-dioxo-1-imidazolidinyl)ethyl)-N-hydroxyformamide;

(±)-N-(1-(((4'-cyano(1,1'-biphenyl)-4-yl)oxy)methyl)-2-(3-methyl-2,5-dioxo-1-imidazolidinyl)ethyl)-N-hydroxyformamide;

(±)-N-(1-(((4'-cyano(1,1'-biphenyl)-4-yl)sulfonyl)methyl)-2-(4,4-dimethyl-2,5-dioxo-1-imidazolidinyl)ethyl)-N-hydroxyformamide;

(±)-N-(1-(((4'-chloro-(1,1'-biphenyl)-4-yl)oxy)methyl)-2-(3,4,4-trimethyl-2,5-dioxo-1-imidazolidinyl)ethyl)-N-hydroxyformamide;

(±)-N-(1-(((3'-cyanomethyl-(1,1'-biphenyl)-4-y)oxy)methyl)-2-(3,5,5-trimethyl-2,4-dioxo-1-imidazolidinyl)propyl)-N-hydroxyformamide;

(±)-N-(1-(((4'-cyano-(1,1'-biphenyl)-4-y)oxy)methyl)-2-isopropylthioethyl)-N-hydroxyformamide;

(±)-N-(1-(((3'-cyanomethyl-(1,1'-biphenyl)-4-y)oxy)methyl)-2-(3,4,4-trimethyl-2,5-dioxo-1-imidazolidinyl)ethyl)-N-hydroxyformamide;

(±)-N-(1-(((4'-cyano-(1,1'-biphenyl)-4-yl)oxy)methyl)-2-(3-ethyl-4,4-dimethyl-2,5-dioxo-1-imidazolidinyl)ethyl)-N-hydroxyformamide;

(±)-N-(1-(((4'-cyano-(1,1'-biphenyl)-4-yl)oxy)methyl)-2-(3-benzyl-4,4-dimethyl-2,5-dioxo-1-imidazolidinyl)ethyl)-N-hydroxyformamide;

(±)-N-(1-(((4'-cyano-(1,1'-biphenyl)-4-y)oxy)methyl)-2-(3,5,5-trimethyl-2,4 -dioxo-1-imidazolidinyl)ethyl)-N-hydroxyformamide;

(±)-N-(1-(((4'-methoxy(1,1'-biphenyl)-4-yl)sulfonyl)methyl)ethyl)-N-hydroxyformamide;

(±)-N-(1-(((4'-chloro(1,1'-biphenyl)-4-yl)sulfonyl)methyl)ethyl)-N-hydroxyformamide;

(±)-N-(1-(((4-(1,3-benzodioxol-5-yl)phenyl)sulfonyl)methyl)ethyl)-N-hydroxyformamide;

(±)-N-(1-(((4-(4-chlorophenoxy)phenyl)sulfonyl)methyl)ethyl)-N-hydroxyformamide;

(±)-N-(1-(((4'-methoxy(1,1'-biphenyl)-4-yl)sulfonyl)methyl)propyl)-N-hydroxyformamide;

(±)-N-(1-(1,1-dimethyl-2-((4'-(trifluoromethyl)(1,1'-biphenyl)-4-yl)sulfonyl)ethyl)-N-hydroxyformamide;

(±)-N-(1-((phenylmethoxy)methyl)-2-((4'-(trifluoromethyl)(1,1'-biphenyl)-4-yl)sulfonyl)ethyl)-N-hydroxyformamide;

(±)-N-(1-(hydroxymethyl)-2-(((4'-(trifluoromethyl)(1,1'-biphenyl)-4-yl)sulfonyl)ethyl)-N-hydroxyformamide;

(±)-N-(1-((4,4-dimethyl-2,5-dioxo-1-imidazolidinyl)methyl)-2-((4'-(trifluoromethyl)(1,1'-biphenyl)-4-yl)thio)ethyl)-N-hydroxyformamide;

(±)-N-(1-((4,4-dimethyl-2,5dioxo-1-imidazolidinyl)methyl)-2-((4'-(trifluoromethyl)(1,1'-biphenyl)-4-yl)sulfonyl)ethyl)-N-hydroxyformamide;

(±)-N-(1-((2,5-dioxo-1-imidazolidinyl)methyl)-2-((4'-(trifluoromethoxy)(1,1'-biphenyl)-4-yl)oxy)ethyl)-N-hydroxyformamide;

(±)-N-(1-(((4'-(trifluoromethyl)(1,1'-biphenyl)-4-yl)sulfonyl)methyl)-2-(3,4,4-trimethyl-2,5-dioxo-1-imidazolidinyl)ethyl)-N-hydroxyformamide;

(±)-N-(1-(((4'-butyl(1,1'-biphenyl)-4-yl)oxy)methyl)-2-(3-methy-2,5-dioxo-1-imidazolidinyl)ethyl)-N-hydroxyformamide;

(±)-N-(1-((3-methy-2,5-dioxo-1-imidazolidinyl)methyl)-2-((4'-(trifluoromethoxy)(1,1'-biphenyl)-4-yl)oxy) ethyl)-N-hydroxyformamide;

N-(4-(4-((4'-chloro(1,1'-biphenyl)-4-yl)sulfonyl)methyl) tetrahydro-2H-pyran-4-yl)-N-hydroxyformamide;

(±)-N-(1-(((4-(4-chlorophenoxy)phenyl)sulfonyl) methyl)-2-(4,4-dimethyl-2,5-dioxo-1-imidazolidinyl) ethyl)-N-hydroxyformamide;

(±)-N-(1-(((4-(4-chlorophenoxy)phenyl)sulfonyl) methyl)-2-(3,4,4-trimethyl-2,5-dioxo-1-imidazolidinyl)ethyl)-N-hydroxyformamide;

(±)-N-(1-(((4-butyl(1,1'-biphenyl)-4-yl)sulfonyl)methyl)-2-(3,4,4-trimethyl-2,5-dioxo-1-imidazolidinyl)ethyl)-N-hydroxyformamide;

(±)-N-(1-(((4'-butyl(1,1'-biphenyl)-4-yl)oxy)methyl)-2-(4,4-dimethyl-2,5-dioxo-1-imidazolidinyl)ethyl)-N-hydroxyformamide;

(±)-N-(1-(((3'-(cyanomethyl)(1,1'-biphenyl)-4-yl)oxy) methyl)-2-(4,4-dimethyl-2,5-dioxo-1-imidazolidinyl) ethyl)-N-hydroxyformamide;

(±)-N-(1-(4-(2-thienyl)phenoxy)methyl)-2-(1-(3,4,4-trimethyl-2,5-dioxo-1-imidazolidinyl)ethyl)-N-hydroxyformamide;

(±)-N-(1-(((3-nitro(1,1'-biphenyl)-4-yl)oxy)methyl)-2-(3,4,4-trimethyl-2,5-dioxo-1-imidazolidinyl)ethyl)-N-hydroxyformamide;

(±)-N-(1-(((4'-methyl(1,1'-biphenyl)-4-yl)oxy)methyl)-2-((3-(methylsulfonyl)-amino)phenyl)ethyl)-N-hydroxyformamide;

(±)-N-(1-(((3-(diethylamino)carbonyl)phenyl)methyl)-2-((4'-methyl(1,1'-biphenyl)-4-yl)oxy)ethyl)-N-hydroxyformamide;

(±)-N-(1-(((4'-cyano(1,1'-biphenyl)-4-yl)oxy)methyl)-2-((4'-cyano (1,1'-biphenyl)-4-yl)oxy)ethyl)-N-hydroxyformamide;

(±)-N-(1-(((4'-cyano(1,1'-biphenyl)-4-yl)oxy)methyl)-2-(4,4-dimethyl-2,5-dioxo-1-imidazolidinyl)ethyl)-N-hydroxyformamide;

(±)-N-(1-((4,4-dimethyl-2,5-dioxo-1-imidazolidinyl) methyl)-2-((4'-(2-methoxyethoxy)(1,1'-biphenyl)-4-yl) oxy)ethyl)-N-hydroxyformamide;

(±)-N-(1-((4,4-dimethyl-2,5-dioxo-1-imidazolidinyl) methyl)-2-((4'-propoxy(1,1'-biphenyl)-4-yl)oxy)ethyl)-N-hydroxyformamide;

(±)-N-(1-((4,4-dimethyl-2,5-dioxo-1-imidazolidinyl) methyl)-2-((4'-pentyloxy(1,1'-biphenyl)-4-yl)oxy) ethyl)-N-hydroxyformamide;

(±)-N-(1-(((3'-(cyanomethyl)(1,1'-biphenyl)-4-yl) sulfonyl)methyl)-3-(4,4-dimethyl-2,5-dioxo-1-imidazolidinyl)propyl)-N-hydroxyformamide;

(±)-N-(1-(((4'-(trifluoromethoxy)(1,1'-biphenyl)-4-yl) sulfonyl)methyl)-2-(3,4,4-trimethy-2,5-dioxo-1-imidazolidinyl)ethyl)-N-hydroxyformamide;

(±)-N-(1-(((4'-cyano(1,1'-biphenyl)-4-yl)sulfonyl) methyl)-2-(3-methy-2,5-dioxo-1-imidazolidinyl) ethyl)-N-hydroxyformamide;

(±)-N-(1-(((3'-(cyanomethyl)(1,1'-biphenyl)-4-yl) sulfonyl)methyl)-2-(3,4,4-trimethyl-2,5-dioxo-1-imidazolidinyl)ethyl)-N-hydroxyformamide;

(±)-N-(1-(((4'-cyano(1,1"-biphenyl)-4-yl)oxyl)methyl)-2-(1,6-dihydro-3-methyl-6-oxo-1-pyridazinyl)ethyl)-N-hydroxyformamide;

(±)-N-(1-(((4'-cyano(1,1'-biphenyl)-4yl)sulfonyl) methyl)-2-(4,4-dimethyl-2,5 -dioxo-1-imidazolidinyl) ethyl)-N-hydroxyformamide;

(±)-N-(1-(((4-(4-fluorophenoxy)phenyl)sulfonyl) methyl)-2-(4,4-dimethyl-2,5-dioxo-1-imidazolidinyl) ethyl)-N-hydroxyformamide;

(±)-N-(1-((4-(4-pyridinyl)phenoxy)methyl)-2-(3,4,4-trimethy-2,5-dioxo-1-imidazolidinyl)ethyl)-N-hydroxyformamide;

(S)-N-(1-((4,4-dimethyl-2,5-dioxo-1-imidazolidinyl) methyl)-2-((4'-(trifluoromethoxy)(1,1'-biphenyl)-4-yl) oxy)ethyl)-N-hydroxyformamide;

(R)-N-(1-((4,4dimethyl-2,5-dioxo-1-imidazolidinyl) methyl)-2-((4'-(trifluoromethoxy)(1,1'-biphenyl)-4-yl) oxy)ethyl)-N-hydroxyformamide;

N-(1-(((4'-(trifluoromethoxy))(1,1'-biphenyl)-4-yl)oxy) methyl)-3-(4,4-dimethyl-2,5-dioxo-1-imidazolidinyl) propyl)-N-hydroxyformamide;

N-(1-(4-((4-pyridinylthio)phenoxy)methyl)-2-(4,4-dimethyl-2,5-dioxo-1-imidazolidinyl)ethyl)-N-hydroxyformamide;

N-(1-((((4-chlorophenoxy)phenyl)sulfonyl)methyl)-3-(4,4-dimethyl-2,5-dioxo-1-imidazolidinyl)propyl)-N-hydroxyformamide;

N-(1-(((4'-cyano(1,1"-biphenyl)-4-yl)oxyl)methyl)-2-(1,6-dihydro-6-oxo-1-pyridazinyl)ethyl)-N-hydroxyformamide;

N-(1-(((4'-(aminosulfonyl)(1,1'-biphenyl)-4-yl)oxy) methyl)-2-(3,4,4-trimethyl-2,5-dioxo-1-imidazolidinyl)ethyl)-N-hydroxyformamide;

N-(1-(((4'-(trifluoromethoxy)(1,1'-biphenyl)-4-yl) sulfonyl)methyl)-2-(4,4-dimethyl-2,5-dioxo-1-imidazolidinyl)ethyl)-N-hydroxyformamide;

N-(1-(4-((4-pyridinyloxy)phenyl)sulfonyl))ethyl)-N-hydroxyformamide;

N-(1-((((4-cyanophenoxy)phenyl)sulfonyl)methyl)-2-(4,4-dimethyl-2,5-dioxo-1-imidazolidinyl)ethyl)-N-hydroxyformamide;

N-(1-((4-((4-(trifluoromethoxy)phenoxy)phenyl) sulfonyl)methyl)-3-(4,4-dimethyl-2,5-dioxo-1-imidazolidinyl)propyl)-N-hydroxyformamide;

N-(1-((4-((4-(trifluoromethoxy)phenoxy)phenyl) sulfonyl)methyl)-2-(4,4-dimethyl-2,5-dioxo-1-imidazolidinyl)ethyl)-N-hydroxyformamide;

(±)-N-hydroxy-N-(1-methyl-3-((4-phenoxyphenyl) sulfonyl)propyl)-formamide;

(±)-N-hydroxy-N-(1-methyl-3-((4-(4-(trifluoromethoxy) phenoxy)phenyl)-sulfonyl)propyl)formamide;

(±)-N-(3-((4-(4-fluorophenoxy)phenyl)sulfonyl)-1-methylpropyl)-N-hydroxy-formamide;

(R)-N-(1-((4,4-dimethyl-2,5-dioxo-1-imidazolidinyl) methyl)-3-((4-phenoxy-phenyl)sulfonyl)propyl)-N-hydroxyformamide;

(R)-N-(1-((2,5-dioxo-3,4,4-trimethyl-1-imidazolidinyl) methyl)-3-((4-phenoxy-phenyl)sulfonyl)propyl)-N-hydroxyformamide;

N-hydroxy-N-(((2-(4-(4pyridinyloxy)phenyl)sulfonyl) methylamino)ethyl)-formamide;

N-hydroxy-N-(1-(hydroxymethyl)-2-((4-((4-(trifluoromethoxyphenyl)carbonyl)amino)-phenyl) sulfonyl)ethyl)formamide;

N-hydroxy-N-(3-hydroxy-2-((4-((phenylcarbonyl)amino) phenyl)sulfonyl)propyl)-formamide;

N-hydroxy-N-(1-(hydroxymethyl)-2-((4-(((4-pentylphenyl)carbonyl)amino)-phenyl)sulfonyl)ethyl) formamide;

2,2-dimethyl-3-((4-phenoxyphenyl)sulfonyl)propyl (hydroxy)formamide;

(1R)-3-((4-(4-chlorophenoxy)phenyl)sulfonyl)-1-((4,4-dimethyl-2,5-dioxo-1-imidazolidinyl)methyl)propyl (hydroxy)formamide;

2,2-dimethyl-3-((4-(4-(trifluoromethoxy)phenoxy) phenyl)sulfonyl)propyl(hydroxy)formamide;

(1R)-3-((4(4-fluorophenoxy)phenyl)sulfonyl)-1-((3,4,4-trimethyl-2,5-dioxo-1-imidazolidinyl)methyl)propyl (hydroxy)formamide;

(1R)-1-((4,4-dimethyl-2,5-dioxo-1-imidazolidinyl) methyl)-3-((4'-(trifluoromethyl)(1,1'-biphenyl)-4-yl) sulfonyl)propyl(hydroxy)formamide;

(±)-2-(((4-(4-fluorophenoxy)phenyl)sulfonyl)methyl) cyclohexyl(hydroxy)formamide; and hydroxy((5-(((4-(4-(trifluoromethoxy)phenoxy)phenyl) sulfonyl)methyl)-1,3-dioxan-5-yl)methyl)formamide.

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection or for rectal administration.

The pharmaceutical compositions of this invention can be administered to humans and other animals orally, rectally, parenterally , intracisternally, intravaginally, intraperitoneally or topically (such as powders, ointments or drops), bucally or as an oral or nasal spray. The term "parenteral" administration, as used herein, refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), and suitable mixtures thereof, vegetable oils (such as olive oil) and injectable organic esters such as ethyl oleate. Proper fluidity can be maintained, for Example, by the use of coating materials such as lecithin, by the maintenance of the required particle size in the case of dispersions and by the use of surfactants.

These compositions may also contain adjuvants such as preservative, wetting agents, emulsifying agents and dispersing agents. Prevention of the action of microorganisms may be ensured by the inclusion of various antibacterial and antifungal agents, for Example, paraben, chlorobutanol, phenol sorbic acid and the like. It may also be desirable to include isotonic agents such as sugars, sodium chloride and the like. Prolonged absorption of the injectable pharmaceutical form may be brought about by the inclusion of agents (such as aluminum monostearate and gelatin) which delay absorption.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues. The injectable formulations can be sterilized, for Example, by filtration through a bacterial-retaining filter or by incorporating sterilizing agents in the form of sterile solid compositions which can be dissolved or dispersed in sterile water or other sterile injectable media just prior to use.

Solid dosage forms for oral administration include capsules, tablets, pills, powders and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar—agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and may also be of a composition such that they release the active ingredient(s) only, or preferentially, in a certain part of the intestinal tract, optionally or in delayed fashion. Examples of embedding compositions which can be used include polymeric substances and waxes.

The active compounds may also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar—agar, and tragacanth and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are the phospholipids and the phosphatidyl cholines (lecithins), both natural and synthetic. Methods to form liposomes are known in the art. See, for Example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants which may be required. Opthalmic formulations, eye ointments, powders and solutions are also contemplated as being within the scope of this invention. Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg, of active compound per kilogram of body weight per day when administered orally to a mammalian patient. If desired, the effective daily dose may be divided into multiple doses for purposes of administration, e.g. two to four separate doses per day.

Determination of Stromelysin Inhibition

The efficacy of the compounds of this invention as matrix metalloproteinase inhibitors was determined by measuring the inhibition of stromelysin. The inhibition of stromelysin by the compounds of this invention was determined as follows: Recombinant truncated stromelysin (human sequence) produced in E. coli was prepared by expression and purification of the protein as described by Ye et al. (Biochemistry, 1992, 31, 11231–11235, which is incorporated herein by reference). The enzyme was assayed by its cleavage of the thiopeptide ester substrate Ac-Pro-Leu-Gly-(2-mercapto-4-methyl-pentanoyl)-Leu-Gly-OEt as described by Weingarten and Feder (Anal. Biochem., 1985, 147, 437–440 (1985), which is incorporated herein by reference) as a substrate of vertebrate collagenase. The reported conditions were modified to allow assays to be carried out in a microtiter plate. Upon hydrolysis of the thioester bond, the released thiol group reacted rapidly with 5,5'-dithio-bis(2-nitrobenzoic acid) (DTNB) to produce a yellow color which was measured by a microtiter plate reader set at 405 nm. The rates of cleavage of the substrate by stromelysin in the presence or absence of inhibitors were measured in a 30 minute assay at ambient temperature. Solutions of the compounds in DMSO were prepared, and these were diluted at various concentrations into the assay buffer (50 mM MES/NaOH pH 6.5 with 10 mM $CaCl_2$ and 0.2% Pluronic F-68), which was also used for dilution of the enzyme and substrate. The potency of the compounds ($IC_{50}$) was calculated from the inhibition/inhibitor concentration data. The compounds of this invention inhibited stromelysin as shown by the data for representative Examples in Table 1.

TABLE 1

| Example | $IC_{50}$ (nM) |
| --- | --- |
| 1 | 130 |
| 2 | 36 |
| 3 | 21 |
| 4 | 9.1 |
| 5 | 17 |
| 6 | 30 |
| 7 | 120 |
| 8 | 170 |
| 9 | 100 |
| 11 | 300 |
| 12 | 180 |
| 13 | 310 |
| 15 | 620 |
| 120 | 4.3 |
| 121 | 130 |
| 123 | 270 |

The efficacy of the compounds of this invention as matrix metalloproteinase inhibitors was also determined by measuring inhibition as outlined below for Gelatinase A, a member of this family of enzymes. Recombinant active gelatinase-A (MMP-2) is purchased from Oncogene Research. The enzyme is assayed by its cleavage of a fluorescent in 150 uL volume in a microfluor plate as described in Science 1990, 247, 954–958. Upon cleavage of the substrate, the fluorescence of the EDANS group is increased 30-fold, and this increase is monitored using a f-max (Molecular Devices) fluorescent plate reader (ex: 335 nm; em: 485 nm). The rates of cleavage of the substrate by gelatinase-A in the presence or absence of inhibitors are measured in a 40 min assay at ambient temperature. Stock solutions of the compounds in DMSO are prepared, and these solutions are diluted into the assay buffer (50 mM Tris HCl, pH 7.4, with 150 mM NaCl and 10 mM $CaCl_2$), which is also used for dilution of the enzyme and substrate. The potencies of the compound [$IC_{50}$], shown below in Table 2, are calculated by plotting the logit function of the percent inhibition data relative to control vs. the logarithm of the inhibitor concentrations.

TABLE 2

| Example | IC$_{50}$ (nM) |
|---------|----------------|
| 129 | 4.3 |
| 130 | 12 |
| 131 | 4.9 |
| 132 | 15 |
| 134 | 120 |
| 135 | 0.6 |

Preparation of Compounds of this Invention

The compounds and processes of the present invention will be better understood in connection with the following synthetic schemes which are merely illustrative of the methods by which the compounds of the invention may be prepared and are not intended to limit the scope of the invention as defined in the appended claims. Representative procedures are outlined in the following Schemes 1–5.

Abbreviations

Abbreviations which have been used in the descriptions of the schemes and the Examples that follow are: THF for tetrahydrofuran; DMF for N,N-dimethylformamide; rt for room temperature; TBDMSCI for tert-butyldimethylsilyl chloride; h for hour; decomp. for decomposition; sat. for saturated; LAH for lithiumaluminum hydride; min for minutes; aq. for aqueous; m-CPBA for meta-chloroperbenzoic acid, Boc for tert-butoxycarbonyl, LDA for lithium diisopropylamide, TFA for trifluoracetic acid, n-BuLi for n-butyllithium, DME for dimethoxyethane, and DMSO for dimethylsulfoxide.

As shown in Scheme 1, deprotonation of the phenolic moiety of 1 with a base, preferably sodium or potassium hydride, and alkylation of the resulting anion with an excess, preferably a two to four-fold excess, of an electrophile, preferably epibromohydrin or epichlorohydrin, provided the alkylated epoxide 2. An excess of a second nucleophile, preferably a two to four-fold excess, was deprotonated with a base such as sodium or potassium hydride and condensed with 2 to provide alcohol 3 which was treated with bis-Boc-hydroxylamine under Mitsunobu conditions to provide the bis-Boc protected hydroxylamine 6. Removal of the Boc-protecting groups with acid, preferably HCl in dioxane or trifluoroacetic acid in dichloromethane, and neutralization of the amine salt with a base, preferably sodium bicarbonate, provided an exposed hydroxylamine moiety which was treated with a formylating agent, preferably formicacetyl anhydride, in solvents such as THF or dichloromethane to provide hydroxamic acid 7.

Alternatively, 2 was converted to the corresponding iodoketone 4 by a two-step procedure which comprised (a) treatment of the epoxide with triphenylphosphine and an iodinating agent, preferably iodine, in an inert solvent such as dichloromethane to provide the corresponding iodoalcohol followed by (b) oxidation to the corresponding iodoketone 4 with a mild oxidizing agent, preferably Dess-Martin periodinane (Dess, D. B.; Martin, J. C., J. Am. Chem. Soc. 1991, 113, 7277–7287, which is incorporated herein by reference). Introduction of $R_1$ was accomplished by alkylation of the desired phenol or benzenenethiol derivative with 4 in the presence of base, preferably potassium carbonate, in a polar solvent such as DMF The resulting ketone was converted to the corresponding oxime 5 by treatment with hydroxylamine hydrochloride in a hydroxylic solvent, preferably ethanol, with a catalytic amount of base, preferably pyridine. When $R_1$ contained sulfur, the alcohol was oxidized to the corresponding ketone using Dess-Martin periodinane in an inert solvent such as dichloromethane then converted to 5 as described above. Treatment of 5 with a reducing agent, preferably boranepyridine complex, in a hydroxylic solvent, preferably ethanol, and adding excess aqueous hydrochloric acid provided the corresponding hydroxylamine which was formylated as described above to provide 7. Depending on the nature of RI group, protection and subsequent deprotection of other reactive groups was required to successfully complete the described synthetic sequences. Commonly used protecting groups are disclosed in Greene, "Protective Groups In Organic Synthesis," (John Wiley & Sons, New York (1981)), which is incorporated herein by reference.

Scheme 1

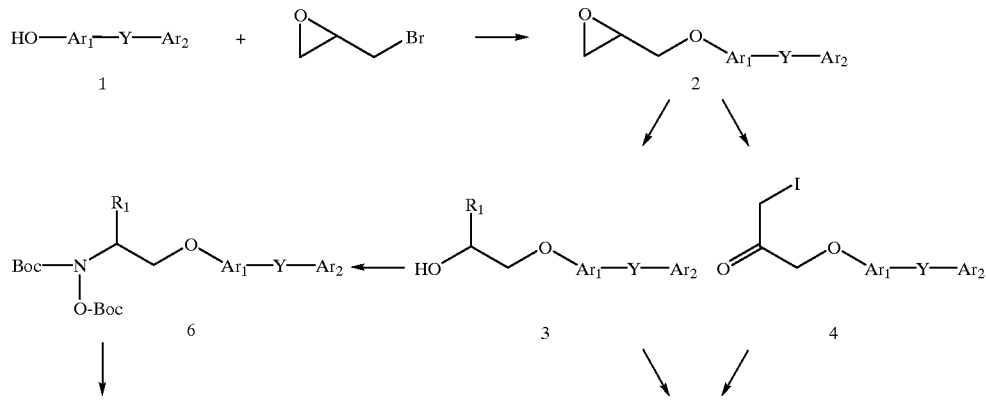

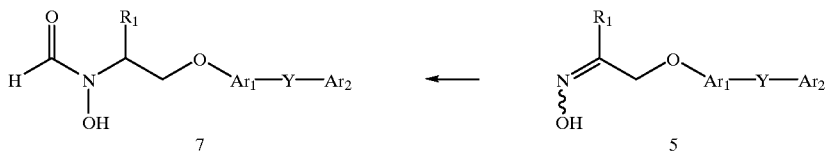

Scheme 2 shows an alternate preparation of intermediate 5. Alkylation of 1 with ethyl bromoacetate was accomplished in the presence of base, preferably potassium carbonate, in a polar solvent, preferably DMF, to provide 8, which was subsequently hydrolyzed to 9 by treatment with aqueous base, preferably lithium hydroxide in a solvent mixture, preferably water and dioxane. Amide 10 was prepared by coupling N,O-dimethylhydroxylamine hydrochloride to 9 with a coupling agent, preferably bis(2-oxo-3-oxazolidinyl)phosphinic chloride (BOP-Cl). Treatment of 10 with $R_1$-MgX, wherein X is Br or Cl, at reduced temperature, preferably −78° C. in an inert solvent, preferably THF, provided ketone 11, which was converted to 5, and finally to 7, as described in Scheme 1.

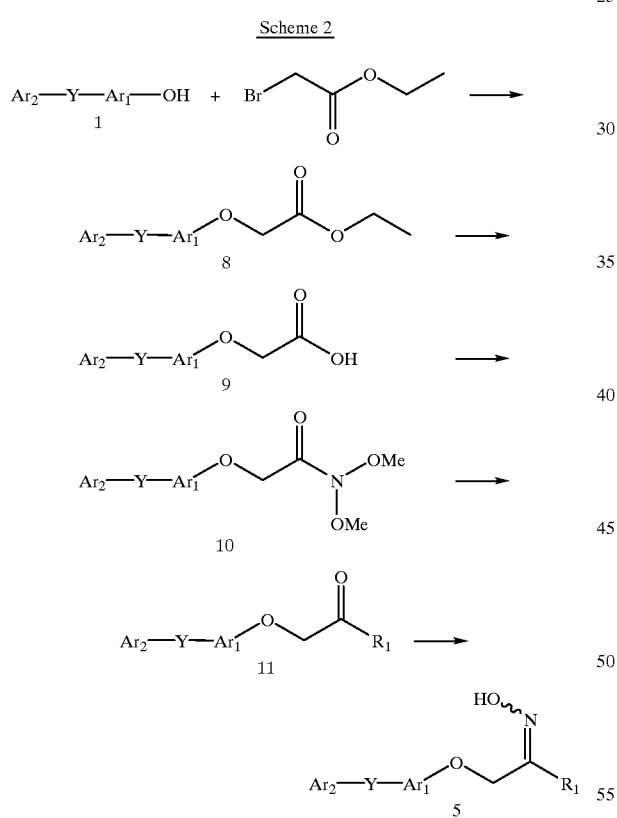

tions to provide the corresponding N-alkenylheterocycle 12. Treatment of 12 with an alkylating agent, preferably methyl iodide, in the presence of base, preferably sodium hydride, provided N-methyl alkenylheterocycle 13, which was epoxidized with meta-chloroperbenzoic acid (mCPBA) in dichloromethane to provide 14. The reaction sequence described in Scheme 1 was then used to convert 14 to hydroxamic acid 5.

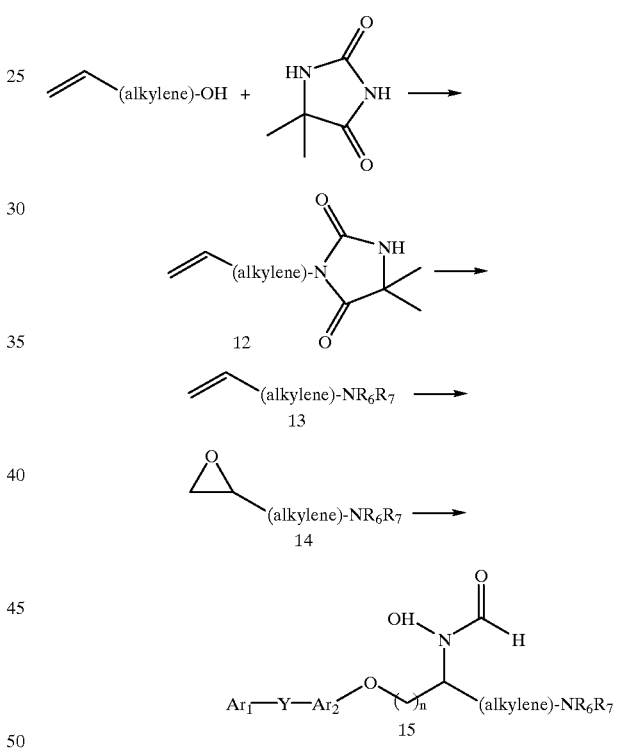

Scheme 3 shows the synthesis of compounds where the introduction of the phenolic and $R_1$ groups was reversed. This route intersects with the route described in Scheme 1 at epoxide 14, and the chemistry described in Scheme 1 may be utilized to convert 14 into the hydroxamic acid by employing HO—$Ar_1$—Y—$Ar_2$ for $R_1$13 H. Heterocyclic derivatives of $R_1$—H, preferably those having appropriate pKa's, such as the hydantoin in this scheme, were condensed with the desired olefinic alcohol under Mitsunobu condiwherein the alkylene group is of one to six carbon atoms, n is 1, and $R_6$ and $R_7$ together with the nitrogen aton to which they are attached, form

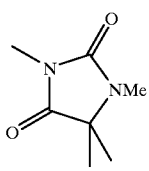

Scheme 4 shows an alternate synthesis of the hydantoin substituted compounds 22 and 23. Alkylation of 16 with a substituted hydantoin 17 in the presence of base, preferably potassium carbonate provides the enol ether 18. Treatment of 18 with a brominating agent such as NBS in acetone, gives the the bromoketone 19 which can then be alkylated with either aryl thiols (20, X=S) or substituted phenols (20, X=O) to afford the ketones 21. Ketones 21, wherin Y is a covalent bond could also be prepared from 19 in a two step procedure, first alkylating with either bromo thiophenols (20a, X=S) or bromophenols (20a, H=O), then coupling the aryl bomides 10a with an appropriate aryl boronic acid following the Suzuki protocol, or an appropriate arul stannane. The reaction sequence described in scheme 1 can then be used to convert 21 into the hydroxamic acids 22. The compounds wherein X=S can be converted to the sulfones 23 via oxidation with an appropriate oxidant such as m-chloroperbenzoic acid or oxone.

Scheme 5 shows an alternate synthesis of the sulfones 29. Deprotonation of the sulfone 25 with a base such as LDA followed by addition to a ketone or aldehyde 24 gives an alcohol which can be dehydrated either by reaction with acid, such as toluene sulfonic acid or by a stepwide 2 step procedure: first convering the alcohol into a leaving group, such as mesylate via treatment with mesyl chloride and triethyl amine, then eliminating with a base, preferably 1,8-diazabicyclo(5.4.0)undec-7-ene. Reaction of the olefin with an O-protected hydroxylamime preferably O-benzyl gives the adduct 28. Formylation as previously described in scheme 1 followed by removal of the protecting group, preferably under hydrogenation conditions for the compounds wherin P is benzyl affords the sulfone 29. The sulfone 28 can also be prepared directly via the deprotonation of sulfone 25, with a base such as n-BuLi and subsequent addition, preferably in the presence of boron trifluoride etherate, to a O-protected oxime 30.

Scheme 4

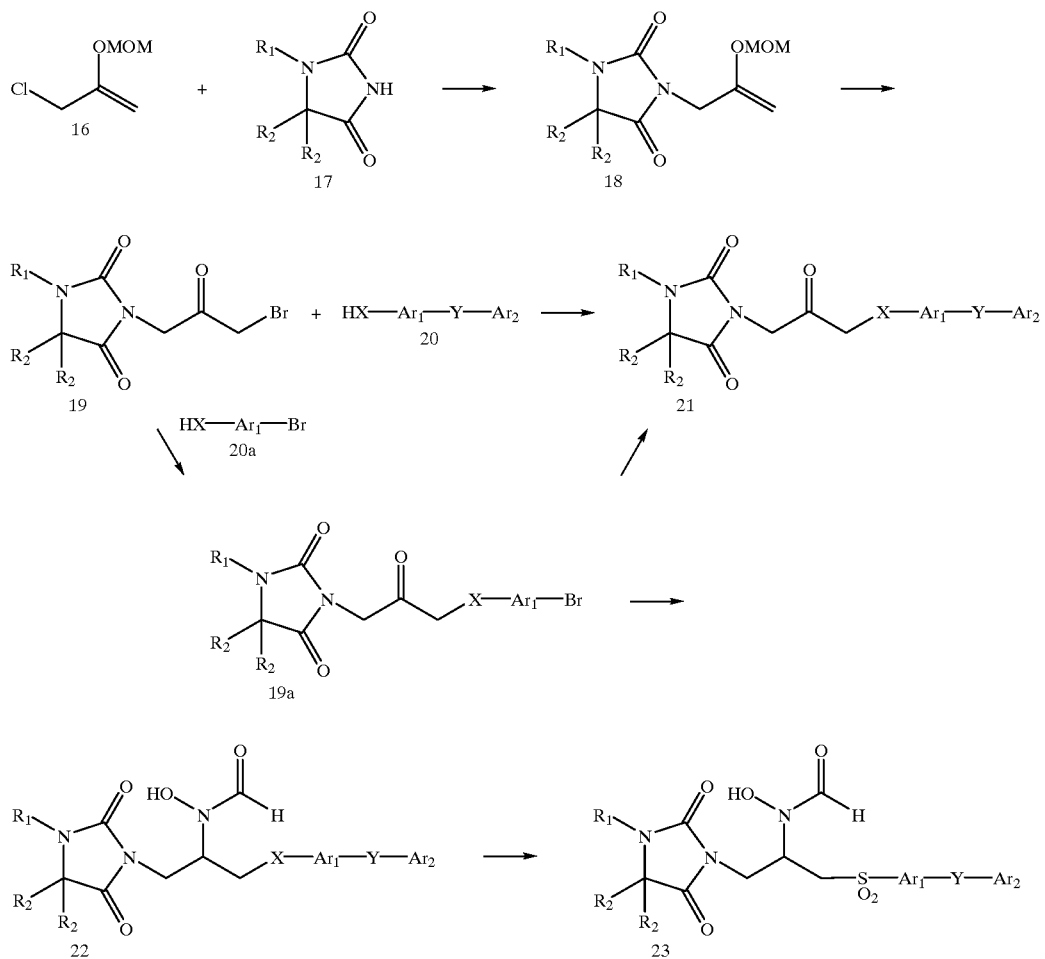

Scheme 5

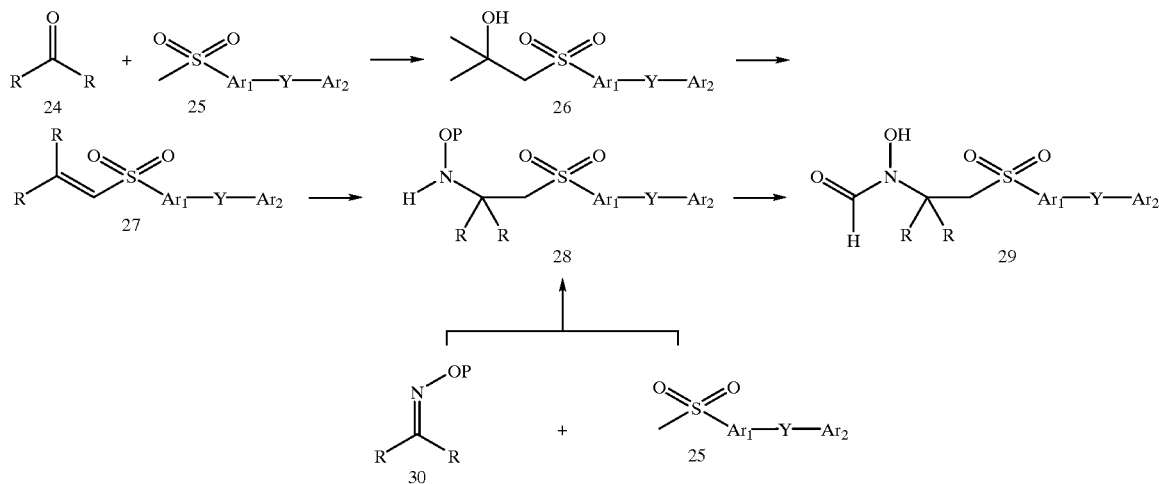

As shown in scheme 6, deprotonation of an aryl alkyl sulfone (32, X=alkyl) or an arylsulfonamide (32, X=NHalkyl) with a base such as n-BuLi followed by reaction with an epoxide 31 provides the alcohol 33. Treatment of the alcohol 33 with bisBoc-hydroxylamine under Mitsunobu coditions affords the protected hydroxylamine 34, which after deprotection under acidic conditions, for Example reaction with TFA, gives the hydroxylamine 35. Formylation with a formylating agent such as formicacetic anhydride provides compound 36.

Scheme 6

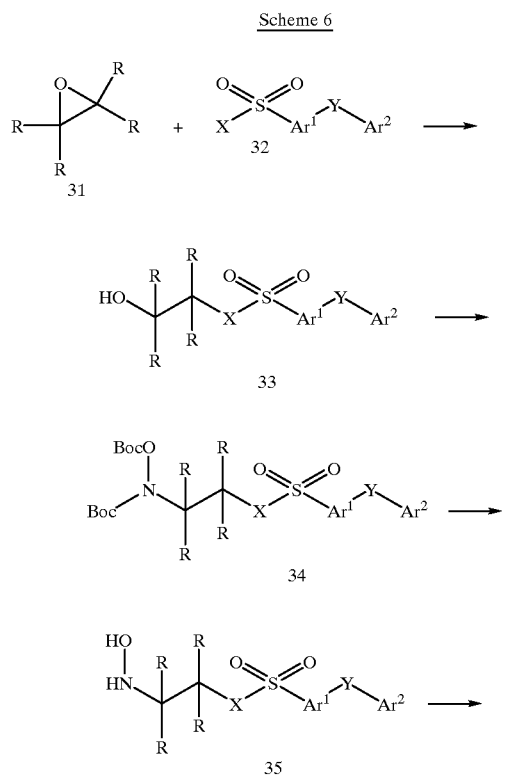

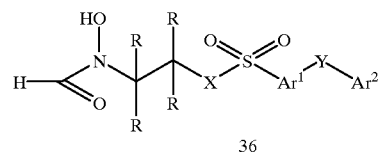

As shown in Scheme 7, deprotonation of an aryl alkyl sulfone (32, X=alkyl) or an arylsulfonamide (32, X=NHalkyl) with a base such as n-BuLi followed by reaction with benzyl glycidol epoxide 37 provides the alcohol 38. Reaction with bisBoc-hydroxylamine as described previously for the conversion of 33 to 34 affords 39. Deprotection of the benzyl ether under hydrogenation conditions in the presence of 10% Pd on carbon catalyst affords the alcohol 40. The alcohol was then reacted with nucleophiles capable of participating in a Mitsunobu reaction (for Example Nu=hydantoin) to provide 41. Deprotection and formylation as described in scheme 6 provides 42.

Scheme 7

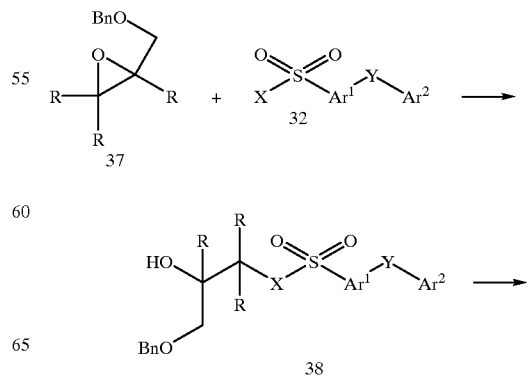

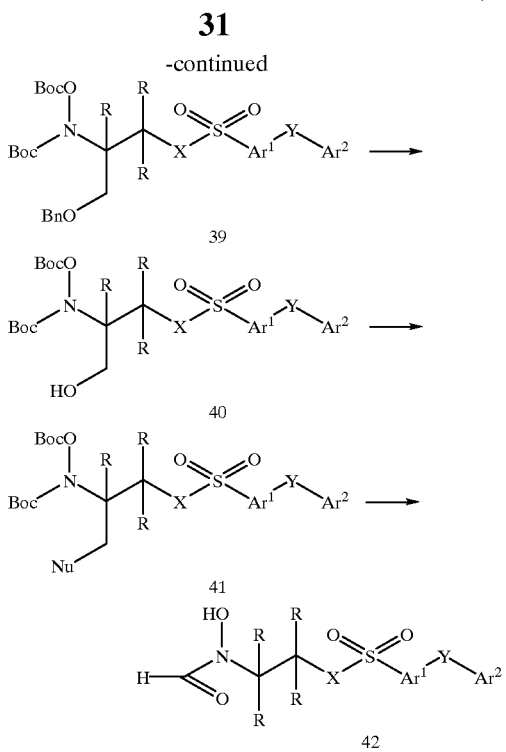

The foregoing may be better understood by reference to the following Examples which illustrate the methods by which the compounds of the invention may be prepared and are not intended to limit the scope of the invention as defined in the appended claims.

EXAMPLE 1

(±)-N-(1-(((4'-cyano-(1,1'-biphenyl)-4-yl)oxy) methyl)-2-phenoxyethyl)-N-hydroxyformamide

EXAMPLE 1A (±)-3-phenoxypropan-(1,2)oxirane

A suspension of sodium hydride (0.47 g, 11.7 mmol) in THF (20 mL) was treated sequentially with a solution of phenol (1.00 g, 10.6 mmol) in THF (20 mL) and epibromohydrin (2.73 mL, 31.8 mmol), refluxed for 2 hours, cooled to room temperature, treated with 20% aqueous potassium hydrogen sulfate, then partitioned between ethyl acetate and brine. The organic layer was washed sequentially with saturated sodium bicarbonate and brine, dried ($Na_2SO_4$), filtered, and concentrated to provide 1.65 g of a golden oil which was purified on silica gel with 10% ethyl acetate/hexanes (500 mL) and 20% ethyl acetate/hexanes to provide 1.19 g (75%) of the desired product.

MS ($DCI/NH_3$) m/e 168 $(M+NH_4)^+$ and 185 $(M+NH_4+NH_3)^+$.

EXAMPLE 1B (±)-1-(4-(4'-carbonitrilephenyl)phenoxy)-3-phenoxy-2-propanol

A suspension of sodium hydride (0.18 g, 4.39 mmol) in THF (4 mL) was treated sequentially with a solution of 4'-hydroxy-4-biphenylcarbonitrile (0.78 g, 3.99 mmol) in THF (4 mL), Example 1A (0.60 g, 3.99 mmol) in THF (2 mL), and DMF (6 mL), refluxed for 1 hour, cooled to room temperature, treated with 20% aqueous potassium hydrogen sulfate, and partitioned between ethyl acetate and brine. The organic layer was washed sequentially with saturated sodium bicarbonate, 15% sodium hydroxide, and brine, dried ($Na_2SO_4$), filtered, and concentrated to provide 1.04 g of a yellow oil which was purified on silica gel with 25–30% ethyl acetate/hexanes to provide 0.42 g (22%) of the desired product.

MS ($DCI/NH_3$) m/e 363 $(M+NH_4)^+$ and 380 $(M+NH_4+NH_3)^+$.

EXAMPLE 1C (±)-N,O-bis(t-butyloxycarbonyl)-1-(4-(4'-carbonitrilephenyl)phenoxy)-3-phenoxy-prop-2-yl-N-hydroxylamine A solution of Example 1B (0.41 g, 1.19 mmol), triphenylphosphine (0.40 g, 1.54 mmol), and di-Boc-hydroxylamine (0.33 g, 1.42 mmol) in THF (5 mL) at room temperature was treated dropwise with diethylazodicarboxylate (0.24 mL, 1.54 mmol), stirred for 1 hour, and concentrated. The resulting oil was redissolved in dichloromethane (30 mL) and concentrated under vacuum (2 cycles) to remove any excess THF, then purified on silica gel with 15% ethyl acetate/hexanes to provide 0.50 g (75%) of the desired product as a colorless foam.

MS ($DCI/NH_3$) m/e 578 $(M+NH_4)^+$.

EXAMPLE 1D (±)-1-(4-(4'-carbonitrilephenyl)phenoxy)-3-phenoxy-prop-2-yl-N-hydroxylamine A solution of Example 1C (0.45 g; 0.80 mmol) in dichloromethane (3 mL) at room temperature was treated with trifluoroacetic acid (6 mL), stirred for 15 minutes, poured into saturated sodium bicarbonate and extracted with ethyl acetate. The combined extracts were washed with brine, dried ($Na_2SO_4$), filtered, and concentrated to provide 0.70 g of a brown oil which was purified on silica gel with 50% ethyl acetate/hexanes to provide 0.23 g (81%) of the desired product as a light yellow foam.

EXAMPLE 1E (±)-N-1-((((4'-cyano-(1,1'-biphenyl)-4yl)oxy) methyl)-2-phenoxyethyl)-N-hydroxyformamide A solution of Example 1D (0.15 g, 0.41 mmol) in dichloromethane (2 mL) was cooled to −10° C., treated with a solution of formicacetyl anhydride (38 mg, 0.43 mmol) in dichloromethane (1 mL), stirred for 15 minutes, diluted with ether, and washed sequentially with saturated sodium bicarbonate, 10% aqueous hydrochloric acid, saturated sodium bicarbonate, and brine, dried ($Na_2SO_4$), filtered, and concentrated to provide 0.17 g of a brown, glassy oil which was purified on silica gel with 97.5% (40% ethyl acetate/hexanes)/2.5% methanol to provide 67 mg (42%) of light brown foam which was recrystallized from ethyl acetate/hexanes/acetone to provide the desired product as light pink, clumpy crystals.

mp 133–135° C.;

$^1H$ NMR (300 MHz, $CDCl_3$) δ 8.15 (br s; 1H), 8.07 (s; 1H), 7.69 (AB;1H; J=9 Hz), 7.62 (AB; 1H; J=9 Hz), 7.54 (d; 1H; J=9 Hz), 7.32 (dd; 1H; J=6.5,8.0 Hz), 6.97–7.06 (m; 3H), 6.92 (d; 2H; J=7.5 Hz), 4.24–4.47 (m; 5H);

MS ($DCI/NH_3$) m/e 345 $(M+NH_4—HCONHOH)^+$;

Anal. calcd for $C_{23}H_{20}N_2O_4$: C, 71.12; H, 5.19; N, 7.21. Found: C, 71.04; H, 5.16; N, 7.01.

EXAMPLE 2

(±)-N-(1-(((4'-cyano-(1,1'-biphenyl)-4-yl)oxy)
methyl)-2-(phenylthio)ethyl)-N-hydroxyformamide

EXAMPLE 2A (±)-3-(4-(4'-carbonitrilephenyl)phenoxy)propan-(1,
2)oxirane

The desired product was prepared following the procedure from Example 1A substituting 4'-hydroxy-4-biphenylcarbonitrile (10.0 g, 51.2 mmol) for phenol. Purification by trituration with ether provided 9.13 g (71%) of the desired product as a chalky solid.

mp 115–116° C.;

MS (DCI/NH$_3$) m/e 269 (M+NH$_4$)$^+$ and 286 (M+NH$_4$+NH$_3$)$^+$.

EXAMPLE 2B (±)-1-(4-(4'-carbonitrilephenyl)phenoxy)-3-thiophenoxy-2-propanol A solution of Example 2A (0.90 g), triethylamine (1.75 mL), and benzenethiol (1.10 mL) in absolute ethanol (14 mL) was heated at reflux for 1 hour, cooled to room temperature, and partitioned between ethyl acetate and 10% sodium hydroxide. The organic layer was washed sequentially with 10% hydrochloric acid, saturated sodium bicarbonate, and brine, dried (Na$_2$SO$_4$), filtered, and concentrated to provide 1.27 g of a thick golden oil which was purified by recrystallization from ethyl acetate/hexanes/methanol to provide the desired product as colorless, clumpy crystals.

mp 105–106° C.;

MS (DCI/NH$_3$) m/e 379 (M+NH$_4$)$^+$.

EXAMPLE 2C (±)-1-(4-(4'-carbonitrilephenyl)phenoxy)-3-thiophenoxy-2-propanone A suspension of the Dess-Martin periodinane in dichloromethane (25 mL) was treated with Example 2B (2.02 g) in dichloromethane (15 mL), stirred at room temperature for 0.5 hours and partitioned between ethyl acetate and saturated sodium bicarbonate. The organic layer was washed sequentially with saturated aqueous sodium thiosulfate, saturated sodium bicarbonate, and brine, dried (Na$_2$SO$_4$), filtered, and concentrated to provide 2.27 g of a clumpy, orange solid which was purified on silica gel with 30% ethyl acetate/hexanes to provide 1.90 g of the desired product as a chalky, light yellow solid.

MS (DCI/NH$_3$) m/e 377 (M+NH$_4$)$^+$.

EXAMPLE 2D (±)-1-4-(4'-carbonitrilephenyl)phenoxy)-3-thiophenoxy-2-propanone Oxime A solution of Example 2C (2.02 g) in methanol (20 mL) and THF (10 mL) was treated sequentially with 10 drops of pyridine then hydroxylaminehydrochloride (0.78 g), heated to reflux for 1 hour, cooled to room temperature, and partitioned between ethyl acetate and saturated sodium bicarbonate. The organic layer was washed sequentially with water and brine, dried (Na$_2$SO$_4$), filtered, and concentrated to provide 1.90 g of the desired product as a chalky yellow solid which was used without further purification.

MS (DCI/NH$_3$) m/e 375 (M+H)$^+$ and 392 (M+NH$_4$)$^+$.

EXAMPLE 2E (±)-N-(4-(4-carbonitrilephenyl)phenoxy)-3-thiophenoxyprop-2-yl)hydroxylamine A solution of Example 2D (1.90 g) in THF (10 mL) was treated sequentially with absolute ethanol (20 mL) and boranepyridine (1.5 mL), then treated with 6N aqueous hydrochloric acid dropwise, stirred for 1 hour at ambient temperature, poured into excess saturated sodium bicarbonate, and extracted with ethyl acetate. The combined organic extracts were washed with brine, dried (Na$_2$SO$_4$), filtered, and concentrated to provide 2.25 g of an orange oil which was purified on silica gel with 30% ethyl acetate/hexanes to provide 1.26 g of the desired product as a light gold oil.

MS (DCI/NH$_3$) m/e 377 (M+H)$^+$ and 394 (M+NH$_4$)$^+$.

EXAMPLE 2F (±)-N-(1-(((4'-cyano-(1,1'-biphenyl)-4-yl)oxy)
methyl)-2-(phenylthio)ethyl)-N-hydroxyformamide A solution of Example 2E (1.24 g) in THF (10 mL) was cooled to -23° C., treated with a solution of formicacetylanhydride (280 μL) in THF (2 mL), stirred for 15 minutes, diluted with ether. The organic layer was washed sequentially with saturated sodium bicarbonate, 10% aqueous hydrochloric acid, saturated sodium bicarbonate, and brine, dried (Na$_2$SO$_4$), filtered, and concentrated to provide 1.27 g of a glassy orange oil which was purified on silica gel with 97.5% (40% ethyl acetate/hexanes)/2.5% methanol to provide 300 mg of the desired product as a light orange foam.

$^1$H NMR (300 MHz, CDCl$_3$) δ 7.95 (br s; 1H), 7.90 (s; 1H), 7.70 (AB; 1H; J=7.5 Hz), 7.62 (AB; 1H; J=7.5 Hz), 7.51 (d; 1H; J=9 Hz), 7.20–7.43 (m; 5H), 6.95 (d; 2H; J=9 Hz), 4.33 (dd; 1H; J=8.5,10.5 Hz), 4.17 (dd; 1H; J=4.5,10.5 Hz), 4.0 (m; 1H), 3.36 (dd; 1H; J=8.5,14 Hz), 3.28 (dd; 1H; J=6,14 Hz);

MS (DCI/NH$_3$) m/e 422 (M+NH$_4$)$^+$.

Anal. calcd for C$_{23}$H$_{20}$N$_2$O$_3$S: C, 68.30; H, 4.98; N, 6.73. Found: C, 68.19; H, 4.86; N, 6.73.

EXAMPLE 3

(±)-N-(1-(((4'-cyano-(1,1'-biphenyl)-4yl)oxy)
methyl)-2-(2,3-dihydro-1,3-dioxo-1H-isoindol-2-yl)
ethyl)-N-hydroxyformamide

EXAMPLE 3A (±)-3-(4-(4'-carbonitrilephenyl)phenoxy)-3-iodo-2-propanol

A solution of iodine (1.54 g, 6.0 mmol) in dichloromethane (20 mL) was treated with triphenylphosphine (1.58 g, 6.0 mmol), stirred for 5 minutes, treated with 3-(4'-carbonitrilephenyl)phenoxy)propan-(1,2) oxirane (1.0 g, 4.0 mmol) in a single portion, stirred at ambient temperature for 30 minutes, treated with water, and partitioned between ethyl acetate and brine. The organic layer was dried (Na$_2$SO$_4$), filtered, and concentrated to provide 3 g of crude product which was purified on silica gel with 30% ethyl acetate/hexanes to provide 1.38 g (91%) of the desired product.

MS (DCI/NH$_3$) m/e 397 (M+NH$_4$)$^+$ and 414 (M+NH$_4$+NH$_3$)$^+$.

EXAMPLE 3B 3-(4-(4'-carbonitrilephenyl)phenoxy)-1-iodopropan-2-one

The desired product was prepared as in Example 2C substituting Example 3A (1.0 g, 2.63 mmol) for 3-(4-(4'-carbonitrilephenyl)phenoxy)-1-thiophenoxypropan-2-ol. Purification on silica gel with 20% ethyl acetate/hexanes provided 0.65 g (66%) of the desired product.

MS (DCI/NH$_3$) m/e 395 (M+NH$_4$)$^+$ and 412 (M+NH$_4$+NH$_3$)$^+$.

EXAMPLE 3C 1-(4-(4'-carbonitrilephenyl)phenoxy)-3-phthaloylpropan-2-one

A solution of Example 3B (1.38 g; 3.66 mmol) in DMF (20 mL) was treated with potassium phthalimide (1.02 g; 5.50 mmol), stirred at ambient temperature for 10 minutes, treated with water, and partitioned between ethyl acetate and brine. The organic layer was dried (Na$_2$SO$_4$), filtered, and concentrated to provide 1.1 g of crude product which was purified on silica gel with ethyl acetate to provide 0.98 g (67%) of the desired product.

MS (DCI/NH$_3$) m/e 414 (M+NH$_4$)$^+$.

EXAMPLE 3D (±)-N-(1-(((4'-cyano-(1,1'-biphenyl)-4yl)oxy)methyl)-2-(2,3-dihydro-1,3-dioxo-1H-isoindol-2-yl)ethyl)-N-hydroxyformamide The desired product was prepared according to Example 2D substituting Example 3C (0.56 g, 1.41 mmol) for 1-(4-(4'-carbonitrilephenyl)phenoxy)-3-thiophenoxypropan-2-one to provide the corresponding oxime which was reduced according to Example 2E substituting 1-(4-(4'-carbonitrilephenyl)phenoxy)-3-phthaloylpropan-2-one oxime for 1-(4-(4'-carbonitrilephenyl)phenoxy)-3-thiophenoxypropan-2-one oxime. The resulting hydroxylamine was formylated according to Example 2F substituting 1-(4-(4'-carbonitrilephenyl)phenoxy)-3-phthaloyl-2-propylhydroxylamine for 1-(4-(4'-carbonitrilephenyl)phenoxy)-3-thiophenoxy-2-propylhydroxylamine. Purification on silica gel with 60% ethyl acetate/hexanes provided 0.185 g (30%) of the desired product.

mp 199–202° C.;

$^1$H NMR (300 MHz, CDCl$_3$) δ 10.06 (s; 0.5H), 9.67 (s; 0.5H), 8.32 (s; 0.5H), 7.99 (s; 0.5H), 7.88 (m; 8H), 7.72 (m; 2H), 7.02 (m; 3H), 4.96 (m; 0.5H), 4.52 (m; 0.5H), 4.25 (m; 2H), 3.78–4.00 (m; 2H);

MS (DCI/NH$_3$) m/e 459 (M+NH$_4$)$^+$;

Anal. calcd for C$_{25}$H$_{19}$N$_3$O$_5$: C, 67.96; H, 4.304; N, 9.51. Found: C, 67.43; H, 4.34; N, 9.04.

EXAMPLE 4

(±)-N-(1-(((4'-cyano-(1,1'-biphenyl)-4-yl)oxy)methyl)-2-(3,4,4-trimethyl-2,5-dioxoimidazolidiny-1-yl)ethyl)-N-hydroxyformamide

EXAMPLE 4A (±)-1-(4-(4'-carbonitrilephenyl)phenoxy)-3-((5,5-dimethyl)hydantoin-3-yl)-2-propanol A solution of 5,5-dimethylhydantoin (0.26 g, 1.99 mmol) in THF (20 mL) was treated with potassium tert-butoxide (1.99 mL, 1.99 mmol), stirred for 5 minutes, treated with 3-(4'-carbonitrilephenyl)phenoxy)-(1,2) oxirane (0.50 g, 1.99 mmol) in a single portion, stirred at 70° C. for 6 hours, treated with excess saturated ammonium chloride, and partitioned between ethyl acetate and brine. The organic layer was dried (Na$_2$SO$_4$), filtered, and concentrated to provide a yellow solid which was purified on silica gel with ethyl acetate to provide 0.70 g (93%) of the desired product.

MS (DCI/NH$_3$) m/e 397 (M+NH$_4$)$^+$.

EXAMPLE 4B (±)-1-(4-(4'-carbonitrilephenyl)phenoxy)-3-(3-(5,5-dimethyl)hydantoin)-2-(t-butyldimethylsilyloxy)propane A solution of Example 4A (0.40 g, 1.06 mmol) in dichloromethane (20 mL) was treated with tert-butyldimethylsilyl chloride (0.24 g, 1.60 mmol) and imidazole (0.1 g, 1.6 mmol), stirred at ambient temperature for 30 minutes, treated with water, and partitioned between ethyl acetate and brine. The organic layer was dried (Na$_2$SO$_4$), filtered, and concentrated to provide a solid which was purified on silica gel with 50% ethyl acetate/hexanes to provide 0.50 g (95%) of the desired product.

MS (DCI/NH$_3$) m/e 511 (M+NH$_4$)$^+$.

EXAMPLE 4C (±)-1-(4'-cyano-(1,1'-biphenyl)-4yl)oxy)-3-(3,4,4-trimethyl-2,5-dioxo-1-imidazolidin-1-yl)-2-t-butlydimethylsilyloxypropane A solution of Example 4B (0.60 g, 1.20 mmol) in THF (20 mL) was treated with sodium hydride (0.035 g, 1.40 mmol) then iodomethane (0.26 g, 1.8 mmol) in a single portion, stirred at 70° C. for 30 minutes, treated with saturated aqueous ammonium chloride and partitioned between ethyl acetate and brine. The organic layer was dried (Na$_2$SO$_4$), filtered, and concentrated to provide the desired product as white crystals.

EXAMPLE 4D (±)-1-(4'-cyano-(1,1'-biphenyl)-4-yl)oxy)-3-(3,4,4-trimethyl-2,5-dioxo-1-imidazolidin-1-yl)-2-propanol A solution of Example 4C in THF (30 mL) was treated with tetrabutylammonium fluoride (1M in THF, 2.0 mL, 2.0 mmol), stirred at ambient temperature for 30 minutes, treated with water and partioned between ethyl acetate and brine. The organic layer was dried (Na$_2$SO$_4$), filtered, and concentrated to provide the crude product which was purified on silica gel with ethyl acetate to provide 0.47 g (100%) of the desired product. MS (DCI/NH$_3$) m/e 411 (M+NH$_4$)$^+$.

EXAMPLE 4E 1-(4'-cyano(1,1'-biphenyl)-4-yl)oxy)-3-(3,4,4trimethyl-2,5-dioxoimidazolidin-1-yl)-2-propanone Example 4D (0.59 g, 1.50 mmol) was processed according to the procedure in Example 2C. Purification of the crude product on silica gel with 50% ethyl acetate/hexanes provided 0.58 g (98%) of the desired product.

MS (DCI/NH$_3$) m/e 409 (M+NH$_4$)$^+$.

EXAMPLE 4F (±)-(1-(4'-cyano-(1,1'-biphenyl)-4-yl)oxy)-3-(3,4,4-trimethyl-2,5-dioxoimidazolidin-1-yl)-pro-2-yl)hydroxylamine Example 4E (0.57 g, 1.46 mmol ) was processed according to the procedures in Examples 2D and 2E. Purification of the crude product on silica gel with 60% ethyl acetate/hexanes provided 0.31 g (52%) of the desired product.

MS (DCI/NH$_3$) m/e 409 (M+H)$^+$.

EXAMPLE 4G (±)-N-(1-(((4'-cyano-(1,1'-biphenyl)-4-yl)oxy)methyl)-2-(3,4,4-trimethyl-2,5-dioxoimidazolidin-1-yl)ethyl)-N-hydroxyformamide Example 4F was processed according to the procedure in Example 2F. Purification of the crude product on silica gel with 60% ethyl acetate/hexanes provided 0.19 g (60%) of the desired product.

mp 65–67° C.;

MS (DCI/NH$_3$) m/e 437 (M+H)$^+$ and 454 (M+NH$_4$)$^+$.

$^1$H NMR (300 MHz, CDCl$_3$) δ 9.90 (s; 0.5H), 9.58 (s; 0.5H), 8.32 (s; 0.5H), 7.92 (s; 0.511), 7.85 (m; 4H), 7.72 (d; 2H; J=5.6 Hz), 7.02 (dd; 2H; J=5.5, 2.5 Hz), 4.86 (m; 0.5H), 4.42 (m; 0.5H), 4.08–4.02 (m; 211), 3.82–3.70 (m; 1H), 3.55–4.05 (m; 1H), 2.8 (s; 1.5H), 2.78 (s; 1.5H), 1.5 (s; 3H), 1.48 (s; 3H);

Anal. calcd for C$_{23}$H$_2$4N$_4$O$_5$: C, 63.23; H, 5.50; N, 12.83. Found: C, 62.96; H, 5.55; N, 12.45.

EXAMPLE 5

(±)-N-(1-(((4'-cyano-(1,1'-biphenyl)-4-yl)oxy)methyl)-3-(3,4,4-trimethyl-2,5-dioxoimidazolidiny-1-yl)propyl)-N-hydroxyformamide

EXAMPLE 5A 1-(prop-2-enyl)-4,4dimethyl-2,5-dioxoimidazolidine

A solution of 3-buten-1-ol (1 g,13.9 mmol), triphenylphosphine (4.73 g, 18 mmol) and 5,5-dimethylhydantoin (2.1 g, 16.7 mmol) in THF (50 mL) was treated dropwise with diethylazodicarboxylate (3.13 g, 18.0 mmol), stirred at ambient temperature for 1 hour, treated with water, and partitioned between ethyl acetate and brine. The organic layer was dried (Na$_2$SO$_4$), filtered, and concentrated to provide crude product which was purified on silica gel with 50% ethyl acetate/hexanes to provide 2.5 g (100%) of the desired product.

EXAMPLE 5B 1-(prop-2-enyl)-3,4,4-trimethyl-2,5-dioxoimidazolidine

A solution of Example 5A (2.3 g, 12.6 mmol) in THF (50 mL) was treated with sodium hydride (0.45 g, 18.9 mmol) then iodomethane (2.7 g, 18.9 mmol) in a single portion, refluxed for 2 hours, cooled to room temperature, treated with water, and partitioned between ethyl acetate and brine. The organic layer was dried (Na$_2$SO$_4$), filtered, and concentrated to provide 3.5 g of a yellow solid which was purified on silica gel with 50% ethyl acetate/hexanes to provide 2.4 g (98%) of the desired product.

MS (DCI/NH$_3$) m/e 214 (M+NH$_4$)$^+$.

EXAMPLE 5C (±)-1-((1',2'-oxiranyl)propyl)-3,4,4-trimethyl-2,5-dioxoimidazolidine A solution of Example 5B (3.0 g, 15.3 mmol) in dichloromethane (50 mL) was treated with m-chloroperbenzoic acid(4.4 g), stirred at ambient temperature for 2 hours, treated with saturated aqueous sodium carbonate, and partitioned between ethyl acetate and brine. The organic layer was dried (Na$_2$SO$_4$), filtered, and concentrated to a solid which was purified on silica gel with 70% ethyl acetate/hexanes to provide 1.5 g (46%) of the desired product.

MS (DCI/NH$_3$) m/e 213 (M+1)$^+$ and 230 (M+NH$_4$)$^+$.

EXAMPLE 5D (±)-(2-hydroxy-3-iodo-propyl)-3,4,4-trimethyl-2,5-dioxoimidazolidine A solution of iodine (0.29 g, 1.88 mmol) in dichloromethane (20 mL) was treated with triphenylphosphine (0.3 g, 1.88 mmol), stirred for 5 minutes, treated with Example 5C (0.2 g, 0.94 mmol) in a single portion, stirred at ambient temperature for 30 minutes, treated with water, and partitioned between ethyl acetate and brine. The organic layer was dried (Na$_2$SO$_4$), filtered, and concentrated to provide a yellow solid which was purified on silica gel with 75% ethyl acetate/hexanes to provide 0.26 g (80%) of the desired product.

MS (DCI/NH$_3$) m/e 342 (M+H)$^+$ and 358 (M+NH$_4$)$^+$.

EXAMPLE 5E 1-(3-iodo-propan-2-only)-3,4,4-trimethyl-2,5-dioxoimidazolidine

Example 5D was processed according to the procedure in Example 2C. Purification the crude product on silica gel with 60% ethyl acetate/hexanes provided 0.3 g (96%) of the desired product.

MS (DCI/NH$_3$) m/e 339 (M+H)$^+$ and 356 (M+NH$_4$)$^+$.

EXAMPLE 5F (±)-1-(3-((4'-cyano-(1,1'-biphenyl)-4-yl)oxy)-propan-2-on-1-yl)-3,4,4-trimethyl-2,5-dioxoimidazolidine A solution of 4'-hydroxy-4-biphenylcarbonitrile (0.38 g, 1.9 mmol) in THF (50 mL) was treated with potassium carbonate (0.5 g) then Example 5E (0.44 g, 1.30 mmol), refluxed for 7 hours, cooled, treated with 10% HCl, and partitioned between ethyl acetate and brine. The organic layer was dried (Na$_2$SO$_4$), filtered, and concentrated to provide a yellow solid which was purified on silica gel with 75% ethyl acetate/hexanes to provide 0.52 g (99%) of the desired product.

MS (DCI/NH$_3$) m/e 423 (M+NH$_4$)$^+$.

EXAMPLE 5G (±)-1-(3-((4'-cyano-(1,1'-biphenyl)-4-yl)oxy)-propan-2-oximino-1-yl)-3,4,4-trimethyl-2,5-dioxoimidazolidine Example 5F was processed according to the procedure in Example 2D. The crude product was purified on silica gel with 75% ethyl acetate/hexanes to provide 0.68 g (1.60 mmol; 100%) of the desired product.

MS (DCI/NH$_3$) m/e 439 (M+NH$_4$)$^+$.

EXAMPLE 5H (±)-N-(1-(((4'-cyano-(1,1'-biphenyl)-4-yl)oxy)methyl)-3-(3,4,4-trimethyl-2,5-dioxo-1-imidazolidinyl)propyl)-N-hydroxyformamide Example 5G was processed according to the procedures in Examples 2E and 2F. Purification of the crude product on silica gel with 75% ethyl acetate/hexanes provided 0.408 g (56%) of the desired product.

mp 68–70° C.;

$^1$H NMR (300 MHz, CDCl$_3$) δ 9.99 (s; 0.5H), 9.46 (s; 0.5H), 8.35 (s; 0.5H), 7.92 (s; 0.51H), 7.92 (d; 2H; J=5.6 Hz), 7.85 (d; 2H; J=5.6 Hz), 7.70 (d; 2H; J=5.6 Hz), 7.05 (d; 2H; J=5.6 Hz), 4.52 (m; 0.5H), 4.18–3.95 (m; 3.5H), 3.46 (m; 2H), 2.82 (s; 1.5H), 2.79 (s; 1.5H), 2.02–1.72 (m; 1H), 1.32 (s; 6H);

MS (DCI/NH$_3$) m/e 468 (M+NH$_4$)$^+$;

Anal. calcd for C$_{24}$H$_{26}$N$_4$O$_5$: C, 63.93; H, 5.77; N, 12.43. Found: C, 63.38; H, 5.99; N, 11.97.

EXAMPLE 6

(±)-N-(1-(((3'-(cyanomethyl)-(1,1'-biphenyl)-4-yl)oxy)methyl)pentyl)-N-hydroxyformamide

EXAMPLE 6A 4-((t-butyldimethyl)silyloxy)phenyl Boronic Acid

A solution of (4-bromophenoxy)trimethylsilane (69 g, 20.9 mmol) in THF (60 mL) was treated with n-butyllithium at −78° C., stirred for 15 minutes, treated with triisopropyl borate, stirred at −78° C. for 10 minutes, warmed to ambient temperature, stirred for 30 minutes, treated with water, and partitioned between ethyl acetate and brine. The organic layer was dried (MgSO$_4$), filtered, and concentrated to provide 4.79 g (91%) of the desired product.

EXAMPLE 6B

4'-hydroxy-3-biphenylcarbonitrilemethane

A mixture of Example 6A (4.8 g, 19.0 mmol), 3-bromophenyl acetonitrile (3.1 g, 16.0 mmol), cesium carbonate (7.8 g, 24.0 mmol) and tetrakis(triphenylphosphine)-palladium(0) (0.55 g, 0.48 mmol) was treated via syringe with DMF (30 mL) under positive nitrogen pressure, stirred at 100° C. for 10 h, treated with water, and partitioned between ethyl acetate and brine. The organic layer was dried (MgSO$_4$), filtered, and concentrated to provide a brown oil which was purified on silica gel with 50% ethyl acetate/hexanes to provide 3.3 g (82%) of the desired product.

MS (DCI/NH$_3$) m/e 227 (M+NH$_4$)$^+$.

EXAMPLE 6C

Ethyl 2-(4-(3'-carbonitrilemethylphenyl)phenoxy)acetate

A solution of Example 6B (0.5 g, 2.4 mmol) in THF (20 mL) was treated with potassium carbonate (0.5 g) and ethyl bromoacetate (0.6 g, 3.6 mmol), refluxed for 3 hours, cooled, treated with 10% HCl, and partitioned between ethyl acetate and brine. The organic layer was dried (Na$_2$SO$_4$), filtered, and concentrated to provide a yellow solid which was purified on silica gel with 50% ethyl acetate/hexanes to provide 0.48 g (68%) of the desired product.

$^1$H NMR (300 MHz, CDCl$_3$) δ 7.52 (m; 4H), 7.40 (m; 1H), 7.36 (m; 1H), 7.0 (m; 2H), 4.65 (s; 2H), 4.30 (q; 2H; J=4.8 Hz), 3.80 (s; 2H), 1.32 (t; 3H; J=4.8 Hz).

EXAMPLE 6D 2-(4-(3'-Carbonitrilemethylphenyl)phenoxy)acetic Acid

A solution of Example 6C (0.47 g, 1.6 mmol ) in 1,4dioxane (20 mL) and water (10 mL) was treated with lithium hydroxide (0.5 g), stirred at ambient temperature for 30 minutes, treated with 10% HCl, and partitioned between ethyl acetate and brine. The organic layer was dried (Na$_2$SO$_4$), filtered, and concentrated to provide a yellow solid which was purified on silica gel with 50% ethyl acetate/hexanes to provide 0.37 g (83%) of the desired product.

$^1$H NMR (300 MHz, CDCl$_3$) δ 7.60 (m; 4H), 7.46 (m; 1H), 7.32 (m; 1H), 7.02 (m; 2H), 4.72 (s; 2H), 4.08 (s; 2H).

EXAMPLE 6E

N,O-dimethyl-2-(4-(3'-carbonitrilemethylphenyl)phenoxy)acetyl Hydroxylamine

A solution of Example 6D (0.35 g, 1.3 mmol), triethylamine (0.5 mL) and bis(2-oxo-3-oxazolidinyl)-phosphinic chloride (0.78 g, 2.6 mmol) in dichloromethane (20 mL) was treated with N,O-dimethyl-hydroxylamine hydrochloride (0.25 g, 2.6 mmol), stirred at ambient temperature for 2 hours, treated with water, and partitioned between ethyl acetate and brine. The organic layer was dried (Na$_2$SO$_4$), filtered, and concentrated to provide a yellow solid which was purified on silica gel with 50% ethyl acetate/hexanes to provide 0.28 g (69%) of the desired product.

$^1$H NMR (300 MHz, CDCl$_3$) δ 7.59 (m; 4H), 7.46 (m; 1H), 7.32 (m; 1H), 7.02 (m; 2H), 4.96 (s; 2H), 4.08 (s; 2H), 3.78 (s; 3H), 3.15 (s; 3H).

EXAMPLE 6F 1-(4-(3'-carbonitrilemethylphenyl)phenoxy)-2-hexanone

A solution of Example 6E (0.27 g, 0.85 mmol) in THF (10 mL) was treated with n-butylmagnsium bromide (1 mL, 2.0 mmol) at −78° C., stirred at −78° C. for 1 h, treated with water, and partitioned between ethyl acetate and brine. The organic layer was dried (Na$_2$SO$_4$), filtered, and concentrated to provide a yellow solid which was purified on silica gel with 25% ethyl acetate/hexanes to provide 0.15 g (59%) of the desired product.

$^1$H NMR (300 MHz, CDCl$_3$) δ 7.52 (m; 4H), 7.42 (m; 1H), 7.28 (m; 1H), 6.98 (m; 2H), 4.60 (s; 2H), 3.82 (s; 2H), 2.62 (t; 2H; J=5.5 Hz), 1.64 (m; 2H); 1.38 (m, 2H), 0.92 (t; 3H; J=4.8 Hz).

EXAMPLE 6G (±)-N-(1-(((3'-(cyanomethyl)-(1,1'-biphenyl)-4yl)oxy)methyl)pentyl)-N-hydroxyformamide Example 6F (0.15 g, 0.50 mmol) was processed according to the procedures described in Examples 2D–F (inclusive). Purification of the crude final product on silica gel with 40% ethyl acetate/hexanes provided 0.07 g (41%) of the desired product.

mp 99–101° C.;

MS (DCI/NH$_3$) m/e 352 (M+NH$_4$)$^+$.

$^1$H NMR (300 MHz, CDCl$_3$) δ 8.58 (brs; 0.5H), 8.04 (brs; 0.5H), 8.0 (s; 1H), 7.48 (m; 4H), 7.42 (m; 1H), 7.26 (m; 1H), 6.98 (m; 2H), 4.05 (t; 1H; J=5.6 Hz), 3.8–4.0 (m; 2H), 3.80(s; 2H), 1.92 (m; 1H0, 1.60 (m; 2H), 1.38 (m; 3H), 0.98 (t; 3H; J=4.8 Hz).

Anal. calcd for C$_{21}$H$_{24}$N$_2$O$_3$: C, 71.50; H, 6.81; N, 7.94. Found: C, 71.44; H, 6.90; N, 7.80.

EXAMPLE 7

(±)-N-(1-(((4'-cyan(1,1'-biphenyl)-4yl)oxy)methyl)-3-methylbutyl)-N-hydroxyformamide 4'-hydroxy-4-biphenylcarbonitrile (1.0 g, 5.12 mmol) was processed according to the procedures described in Examples 6C–G (inclusive), but substituting isobutylmagnesium bromide for the n-butylmagnesium bromide used in Example 6F. Purification of the crude final product on silica gel with 30% ethyl acetate/hexanes provided 0.036 g of the desired product.

mp 112–113° C.;

MS (DCI/NH$_3$) m/e 356 (M+NH$_4$)$^+$.

$^1$H NMR (300 MHz, CDCl$_3$) δ 7.95 (s; 1H), 7.70 (d; 2H; J=5.6 Hz), 7.62 (d; 2H; J=5.8), 7.52 (d; 2H; J=5.8 Hz), 6.98 (d; 2H; J=5.8 Hz), 4.25 (m; 1H), 3.92–4.05 (m; 2H), 1.95 (m; 1H), 1.75 (m; 1H), 1.35(m; 1H), 1.00 (d; 3H; J=4.8 Hz), 0.98 (d; 3H; J=4.8 Hz).

Anal. calcd for C$_{20}$H$_{22}$N$_2$O$_3$: C, 70.92; H, 6.50; N, 8.27. Found: C, 70.91; H, 6.68; N, 8.13.

EXAMPLE 8

(±)-N-(1-(((4'-cyano-(1,1'-biphenyl)-4-yl)oxy) methyl)-2-methylbutyl)-N-hydroxyformamide The desired product was prepared following the sequence of steps described in Example 7 but substituting sec-butylmagnesium chloride for isobutylmagnesium bromide. Purification of the crude final product on silica gel with 30% ethyl acetate/hexanes provided 0.10 g of the desired product.

mp 96–98° C.;

MS (DCI/NH$_3$) m/e 356 (M+NH$_4$)$^+$.

$^1$H NMR (300 MHz, CDCl$_3$) δ 7.95 (s; 1H), 7.70 (d; 2H; J=5.6 Hz), 7.62 (d; 2H; J=5.8), 7.52 (d; 2H; J=5.8 Hz), 6.98 (d; 2H; J=5.8 Hz), 4.32 (m; 1H), 4.15 (m; 2H), 3.65 (m; 1H), 1.98 (m; 1H), 1.62 (m; 1H), 1.02 (m; 3H), 0.98 (m; 3H;).

Anal. calcd for 0.8 H$_2$O+C$_{20}$H$_{22}$N$_2$O$_3$: C, 68.03; H, 6.69; N, 7.90. Found: C, 68.60 ; H, 6.58; N, 7.23.

EXAMPLE 9

(±)-N-(1-(((4'-cyano-(1,1'-biphenyl)-4-yl)oxy) methyl)pentyl)-N-hydroxyformamide The desired product was prepared following the sequence of steps described in Example 7 but substituting n-butylmagnesium bromide for isobutylmagnesium bromide. Purification of the crude final product on silica gel with 30% ethyl acetate/hexanes provided 0.210 g of the desired product.

mp 105–108° C.;

MS (DCI/NH$_3$) m/e 356 (M+NH$_4$)$^+$.

$^1$H NMR (300 MHz, CDCl$_3$) δ 7.95 (s; 1H), 7.70 (d; 2H; J=5.6 Hz), 7.62 (d; 2H; J=5.8), 7.52 (d; 2H; J=5.8 Hz), 6.98 (d; 2H; J=5.8 Hz), 4.25 (m; 1H), 3.99–3.82 (m; 2H), 1.92 (m; 1H), 1.60 (m; 2H), 1.40 (m; 3H), 0.98 (t; 3H; J=4.3 Hz).

Anal. calcd for 0.5C$_6$H$_6$+C$_{20}$H$_{22}$N$_2$O$_3$: C, 73.13; H, 6.62; N, 7.42. Found: C, 73.18; H, 6.65; N, 7.39.

EXAMPLE 10

(±)-N-(1-(((4'-cyano-(1,1'-biphenyl)-4-yl)oxy) methyl)-2-(4-methylphenyl)ethyl)-N-hydroxyformamide The desired product was prepared following the sequence of steps described in Example 7 but substituting 4-methylbenzylmagnesium bromide for isobutylmagnesium bromide. Purification of the crude final product on silica gel with 30% ethyl acetate/hexanes provided 0.24 g of the desired product.

mp 173–175° C.;

MS (DCI/NH$_3$) m/e 404 (M+NH$_4$)$^+$.

$^1$H NMR (300 MHz, CDCl$_3$) δ 7.70 (d; 2H; J=5.6 Hz), 7.68 (s; 1H), 7.62 (d; 2H; J=5.8), 7.52 (d; 2H; J=5.8 Hz), 7.12 (s; 4H), 6.98 (d; 2H; J=5.8 Hz), 4.35 (m; 1H), 4.12–3.98 (m; 2H), 3.15 (m; 1H), 2.94 (m; 1H), 1.35 (s; 3H).

Anal. calcd for C$_{24}$H$_{22}$N$_2$O$_3$: C, 74.52; H, 5.69; N, 7.24. Found: C, 73.95; H, 5.79; N, 7.06.

EXAMPLE 11

(±)-N-(2-((4'cyano-(1,1'-biphenyl)-4-yl)oxy)-1-(4-fluorophenyl)ethyl)-N-hydroxyformamide The desired product was prepared following the sequence of steps described in Example 7, but substituting 4-fluorophenylmagnesium bromide for isobutylmagnesium bromide. Purification of the crude final product on silica gel with 30% ethyl acetate/hexanes provided 0.285 g of the desired product.

mp 194–196° C.;

MS (DCI/NH$_3$) m/e 394 (M+NH$_4$)$^+$;

$^1$H NMR (300 MHz, CDCl$_3$) δ 9.70 (brs; 1H), 8.42 (s; 0.5H), 8.28 (s; 0.5H), 7.86 (m; 4H), 7.72 (d; 2H; J=5.6 Hz), 7.55 (m; 2H), 7.25 (m; 2H), 7.12 (d; 2H; J=5.8 Hz), 5.72 (brs; 0.5H), 5.35 (brs; 0.5H), 4.60 (m; 1H), 4.36 (m; 1H);

Anal. calcd for C$_{22}$H$_{17}$N$_2$O$_3$F: C, 70.14; H, 4.45; N, 7.44. Found: C, 70.19 ; H, 4.25; N, 7.30.

EXAMPLE 12

(±)-N-(1-(((4'-cyano-(1,1'-biphenyl-4-yl)oxy) methyl)-2-(4-fluorophenyl)ethyl)-N-hydroxyformamide The desired product was prepared following the sequence of steps described in Example 7 but substituting 4-fluorobenzylmagnesium bromide for isobutylmagnesium bromide. Purification of the crude final product on silica gel with 30% ethyl acetate/hexanes provided 0.22 g of the desired product.

MS (DCI/NH$_3$) m/e 408 (M+NH$_4$)$^+$;

$^1$H NMR (300 MHz, CDCl$_3$) δ 8.35 (brs; 1H), 7.65 (m; 5H), 7.52 (d; 2H; J=5.6 Hz), 7.20 (m; 2H), 6.98 (m; 4H), 4.35 (m; 1H), 4.15–3.98 (m; 2H), 3.18 (dd; 1H; J=6.0, 9.0 Hz), 2.95 (dd; 1H; J=3.0, 9.0 Hz);

Anal. calcd for C$_{23}$H$_{19}$N$_2$O$_3$F: C, 70.69; H, 4.87; N, 7.17. Found: C, 70.38; H, 4.96; N, 6.98.

EXAMPLE 13

(±)-N-(1-(((4'-cyano-(1,1'-biphenyl)-4-yl)oxy) methyl)ethyl)-N-hydroxyformamide

EXAMPLE 13A (4-(4'-carbonitrilephenyl)phenoxy)propan-2-one

A solution of 4-(4'-carbonitrilephenyl)phenol (4.86 g, 24.9 mmol) in DMF (100 mL) was treated with potassium carbonate (13.8 g, 99.6 mmol), heated at 50° C. for 10 minutes, treated in a single portion with chloroacetone (2.48 mL, 30 mmol), stirred for 4 hours at ambient temperature, and partitioned between 3:1 ether:hexanes and saturated aqueous sodium carbonate. The organic layer was dried (MgSO$_4$), filtered, and concentrated under vacuum to ⅓ of its original volume to cause precipitation of product from solution. The solution was treated with more ether and stored at −20° C. for 17 hours. The desired product (2.01 g, 32%) was collected by filtration and dried under vacuum.

MS (DCI/NH$_3$) m/e 251 (M)$^+$, 269 (M+NH$_4$)$^+$ and 286 (M+NH$_4$+NH$_3$)$^+$.

EXAMPLE 13B (±)-N-(1-(((4'-cyano-(1,1'-biphenyl)-4-yl)oxy)methyl)ethyl)-N-hydroxyformamide The desired product was obtained following the procedures in Examples 2D–F (inclusive) but substituting Example 13A (2.00 g, 7.96 mmol) for Example 2C. Purification of the crude final product on silica gel with 5% methanol/dichloromethane provided 325 mg of the desired product.

mp 141–144° C.;

$^1$H NMR (300 MHz, d$_6$-DMSO) δ 9.88 and 9.45 (br s; 1H), 8.02 and 8.33 (s; 1H), 7.90 (AB; 2H; J=7.5 Hz), 7.84 (AB; 2H; J=7.5 Hz), 7.61 (d; 2H; J=9 Hz), 7.06 (d; 2H; J=9 Hz), 4.67 (m; 0.32H), 3.92–4.25 (m; 2.68H), 1.23 and 1.18 (d; 3H; J=6 Hz);

MS (DCI/NH$_3$) m/e 314 (M+NH$_4$)$^+$;

Anal. calcd for C$_{17}$H$_{16}$N$_2$O$_3$: C, 68.90; H, 5.44; N, 9.45. Found: C, 68.61; H, 5.55; N, 9.21.

EXAMPLE 14

N-(2-((4'-cyano-(1,1'-biphenyl)-4-yl)oxy)ethyl)-N-hydroxyacetamide

EXAMPLE 14A 2-(4-(4'-carbonitrilephenyl)phenoxy)-bromoethane

A solution of 4-(4'-carbonitrilephenyl)phenol (3.00 g, 24.8 mmol) in DMF (20 mL) was treated with potassium carbonate (8.24 g, 99.4 mmol) and 1,2-dibromoethane (6.42 mL, 124 mmol), heated at 50° C. for 19 hours, and partitioned between 3:1 ether:hexanes and water. The organic layer was separated and the aqueous layer was extracted with 3:1 ether:hexanes. The combined organic layers were dried (MgSO$_4$), filtered, and concentrated. Purification of the crude product on silica gel with 50% dichloromethane/hexanes) provided a white solid which was recrystallized from ether/pentane to provide 1.25 g (17%) of the desired product as colorless needles.

MS (DCI/NH$_3$) m/e 301/303 (M)$^+$, 319/321 (M+NH$_4$)$^+$ and 336/338 (M+NH$_4$+NH$_3$)$^+$.

EXAMPLE 14B

N,O-bis(t-butyloxycarbonyl)-2-((4(4'-carbonitrilephenyl)phenoxy)ethyl-N-hydroxylamine A solution of N,O-bis(t-butyloxycarbonyl)-N-hydroxylamine (443 mg, 1.9 mmol) in DMF (15 mL) was treated with a 60% oil dispersion of sodium hydride (76 mg, 1.9 mmol), stirred at ambient temperature for 15 minutes, treated with Example 13A (0.54 g, 1.79 mmol), stirred for 4 hours at ambient temperature and partitioned between 1:1 ether:hexanes and saturated aqueous ammonium chloride. The organic layer was separated, and the aqueous layer was extracted with 1:1 ether:hexanes. The combined organic layers were dried (MgSO$_4$), filtered, and concentrated. Purification on silica gel with 10% ethyl acetate/hexanes provided 0.65 g (80%) of the desired product as colorless viscous oil.

MS (DCI/NH$_3$) m/e 472 (M+NH$_4$)$^+$.

EXAMPLE 14C 2-((4-(4'-carbonitrilephenyl)phenoxy)ethyl-N-hydroxylamine Hydrochloride Example 14B (0.64 g, 1.41 mmol) was treated with 4N hydrochloric acid in dioxane (10 mL) and stirred at ambient temperature for 2.5 hours, during which time a colorless precipitate formed. The precipitate was collected by filtration, washed with dioxane, and dried to afford the desired product as a colorless solid (0.22 g, 56%).

EXAMPLE 14D

N,O-bis(acetyl)-2-((4-(4'-carbonitrilephenyl)phenoxy)ethyl-N-hydroxylamine

A solution of Example 14C (27 mg, 0.093 mmol) in THF at 0° C. was treated with triethylamine (32 µL, 0.23 mmol), stirred for 1 hour at 0° C., treated dropwise with acetyl chloride (16 µL), stirred for 1 hour at 0° C. and 18 hours at ambient temperature, and partitioned between 1N aqueous hydrochloric acid and ether. The organic layer was separated, and the aqueous layer was extracted with ethyl acetate. The combined organic layers were dried (MgSO$_4$), filtered, and concentrated. Purification of the residue on silica gel with 2% acetone/dichloromethane provided 29 mg (83%) of the desired product.

MS (DCI/NH$_3$) m/e (M+NH$_4$)$^+$.

EXAMPLE 14D

N-(2-((4'-cyano-(1,1'-biphenyl)-4-yl)oxy)ethyl)-N-hydroxyacetamide

A solution of Example 14D (29 mg, 0.077 mmol) in THF (5 mL) and ethanol (2 mL) was cooled to 0° C., treated with aqueous lithium hydroxide (0.31 mL of 1.0 N lithium hydroxide), stirred at 0° C. for 10 minutes and at ambient temperature for 1.5 hours, and partitioned between water and ethyl acetate. The organic layer was separated and the aqueous layer was extracted with ether. The combined organic layers were washed with 1N aqueous hydrochloric acid, dried (MgSO$_4$), filtered, and concentrated to a semi-solid which was purified by trituration with ethyl acetate to provide 19.7 mg (86%) of the desired product as a colorless solid.

mp 174–175° C.;

$^1$H NMR (300 MHz, d$_6$-DMSO) δ 9.90 (br s; 1H), 7.88 (AB; 2H; J=7.5 Hz), 7.84 (AB; 2H; J=7.5 Hz), 7.71 (d; 2H; J=8.5 Hz), 7.07 (d; 2H; J=8.5 Hz), 4.20 (t; 2H; J=7.5,7.5 Hz), 3.89 (t; 2H; J=7.5,7.5 Hz), 2.02 (s; 3H);

MS (DCI/NH$_3$) m/e 297 (M+H)$^+$ and 314 (M+NH$_4$)$^+$;

Anal. calcd for C$_{17}$H$_{16}$N$_2$O$_3$(0.25H$_2$O): C, 67.87; H, 5.52; N, 9.31. Found: C, 67.65; H, 5.55; N, 9.12.

EXAMPLE 15

N-(2-((4'cyano-(1,1'-biphenyl)-4-yl)oxy)ethyl)-N-hydroxyformamide

A solution of Example 14C (78 mg, 0.27 mmol) in THF (2.0 mL) was treated with triethylamine (75 µL, 0.54 mmol) then dropwise with formicacetyl anhydride (41 mg, 0.30 mmol) in THF (0.5 mL), stirred for 2 hours at ambient temperature, and partitioned between ethyl acetate and 1N aqueous hydrochloric acid. The organic layer was separated and the aqueous layer was extracted with ethyl acetate. The combined organic layers were dried (MgSO$_4$), filtered, and concentrated. Purification by chromatography on silica gel with 0.2% acetic acid/ethyl acetate and subsequent recrystallization from cold methanol provided 14.7 mg (19%) of the desired product.

mp 142–145° C.;

$^1$H NMR (300 MHz, d$_6$-DMSO) δ 10.17 and 9.74 (br s; 1H), 8.34 and 7.98 (br s; 1H), 7.88 (AB; 2H; J=7.5 Hz), 7.84

(AB; 2H; J=7.5 Hz), 7.73 (d; 2H; J=8.5 Hz), 7.07 (d; 2H; J=8.5 Hz), 4.14–4.26 (m; 2H), 3.77–3.88 (m; 2H);

MS (DCI/NH$_3$) m/e 300 (M+NH$_4$)$^+$;

Anal. calcd for $C_{16}H_{14}N_2O_3(0.125H_2O)$: C, 67.54; H, 5.05; N, 9.84. Found: C, 67.59; H, 5.32; N, 9.53.

EXAMPLE 16

N-(1-(4-((2E-phenylethenyl)phenoxy)methyl)-2-(3, 4,4-trimethyl-2,5-dioxo-1-imidazolidinyl)ethyl)-N-hydroxyformamide

EXAMPLE 16A 3-(3,4,4-trimethyl-2,5-dioxoimidazolidin-1-yl)-2-methoxymethyloxy-prop-1-ene A mixture of 1,5,5 trimethylhydantoin (7.0 g, 49.2 mmol), powdered potassium carbonate (8.16 g, 59 mmol) and 2-methoxymethyloxy-allyl chloride (7.65 g, 56 mmol) in dry DMF (100 mL) was heated to 100° C. with stirring for 1.5 h. The reaction mixture was cooled to room temperature, filtered, and the filtrate was concentrated, then partitioned between ethyl acetate and water. The organic extract was washed twice with water, brine, dried and concentrated, then purified via silica gel chromatography eluting with 50% ethyl acetate: hexane to give 10.58 g (89%) of the desired product.

MS (DCI/NH$_3$) m/e 243 (M+H)$^+$ and 260 (M+NH$_4$)$^+$.

EXAMPLE 16B 1-bromo-3-(3,4,4-trimethyl-2,5-dioxoimidazolidin-1-yl)propan-2-one A 0° C. solution of Example 16A (10.58 g, 43.7 mmol) in acetone (200 mL) was treated sequentially with a solution of potassium carbonate (0.58 g, 4.2 mmol) in water (60 mL) and N-bromosuccinimide (8.56 g, 48 mmol)and the resulting mixture was stirred with the ice bath in place. An additional 2 portions of 1.5 g of N-bromosuccinimide were added after 1 and 2 hours, respectively. The ice bath was then removed and the reaction was allowed to stir for an additional 10 min, then was concentrated and extracted twice with ethyl acetate. The combined extracts were washed with aq. 0.5 M NaHSO$_3$, 1M NaHCO$_3$, water, brine, dried, filtered, and concentrated. The residue was purified via silica gel chromatography eluting with 50% ethyl acetate: hexane to give 7.39 g (61%) of the desired product.

MS (DCI/NH$_3$) m/e 277/279 (M+H)$^+$ and 294/296 (M+NH$_4$)$^+$.

EXAMPLE 16C 1-(4'-bromophenyloxy)-3-(3,4,4-trimethyl-2,5-dioxoimidazolidin-1-yl)-2-propanone To a suspension of 4-bromophenol (3.99 g, 23.0 mmol) and cesium carbonate (7.45 g, 22.9 mmol) in DMF (150 mL) was added a solution of Example 16B (3 g, 11.5 mmol) in DMF (5 mL), dropwise over 30 minutes. The suspension was stirred at room temperature for 16 hours, diluted with ethyl acetate (500 mL), and the organic phase was washed with water, brine, and dried (MgSO$_3$, filtered, and concentrated. Flash chromatography on silica gel (hexane/ethyl acetate 1:1) gave 2.55 g of the desired product as a white solid.

EXAMPLE 16D

To a warm (100° C.) solution of 16C (0.5 g, 1.35 mmol) and tributyl(phenylethynyl)tin (0.64 g, 1.62 mmol) in toluene (25 mL) was added a catalytic amount of Pd(PPh$_3$)$_4$. The reaction was brought to reflux and stirred for 7 hours. The resulting black solution was diluted with ethyl acetate (125 mL) and the organic phase was washed with 1M NaOH and brine, dried over magnesium sulfate, filtered, and concentrated. Flash chromatography on silica gel (gradient elution; hexane/ethyl acetate 4:1 to 1:1) gave 0.24 g of the desired compound after trituration with diethyl ether.

EXAMPLE 16E

N-(1-(4-((2E-phenylethenyl)phenoxy)methyl)-2-(3, 4,4-trimethyl-2,5-dioxo-1-imidazolidinyl)ethyl)-N-hydroxyformamide The desired product was prepared in the same manner as Example 2D,E,F substituting 16D for 2C.

$^1$H NMR (300 MHz, d$_6$-DMSO) δ 9.90 (s, 0.5H), 9.58 (s, 0.5H), 8.31 (s, 0.5H), 7.9 (s, 0.5H), 7.57–7.54 (m, 6H), 7.38–7.33 (m, 2H), 7.26–7.08 (m, 6H), 6.94–6.90 (m, 2H), 4.80 4.60 (m, 0.5H), 4.55–4.40 (m, 0.5H), 4.164.04 (m, 4H), 3.76–3.73 (m, 2H), 3.61–3.57 (2, 2H), 2.79 (s, 6H), 1.28 (s, 12H);

MS (ESI) m/e M−H (436), M+H (438);

Anal. Calcd for: $C_{24}H_{27}N_3O_5.H_2O$: C, 63.28; H, 6.41; N, 9.22. Found: C, 63.06; H, 5.97; N, 8.94.

EXAMPLE 17

N-(1-((4-(2-furanyl)phenoxy)methyl)-2-(3,4,4-trimethyl-2,5-dioxo-1-imidazolidinyl)ethyl)-N-hydroxyformamide The desired product was prepared as in Example 16 substituting 2-(tributylstannyl) furan for tributyl (phenylethynyl)tin in Example 16D.

$^1$H NMR (300 MHz, d$_6$-DMSO) δ 9.86 (s, 0.5H), 9.53 (s, 0.5H), 8.30 (s, 0.5H), 7.91 (s, 0.5H), 7.67–7.61 (m, 6H), 6.96–6.94 (m, 4H), 6.79–6.74 (d, 2H, J=3.4 Hz), 6.55–6.54 (m, 2H), 4.80–4.60 (m, 0.5H), 4.45–4.30 (m, 0.5H), 4.17–3.98 (m, 6H), 3.76–3.70 (m, 2H), 3.62–3.56 (m, 2H), 2.79 (s, 6H), 1.28 (s, 12H);

MS (ESI) m/e M+H (402), M−H (400), M+NH$_4$ (419);

Anal. Calcd for: $C_{20}H_{23}N_3O_6$: C, 59.84; H, 5.77; N, 10.46. Found: C, 59.83; H, 5.90; N, 10.12.

EXAMPLE 18

N-(1-(((4'-butoxy(1,1'-biphenyl)-4-yl)oxy)methyl)-2-(3,4,4-trimethyl-2,5-dioxo-1-imidazolidinyl)ethyl)-N-hydroxyformamide

EXAMPLE 18A 1-(4'-butyloxy-(1,1'-biphenyl)-4-yl)oxy)-3-(3,4,4-trimethyl-2,5-dioxoimidazolidin-1-yl)-2-propanone To a warm (75° C.) solution of Example 16C (0.1 g, 0.27 mmol) and 4-butoxyphenylboronic acid (0.08 g, 0.41 mmol) in DME (2mL) was added a 1M Na$_2$CO$_3$ solution (0.4mL) followed by a catalytic amount of PdCl$_2$(dppf). The reaction was stirred at 100° for 2 hours, diluted with ethyl acetate (25 mL), washed sequentially with saturated ammonium chloride, water, and brine, dried over magnesium sulfate, filtered, and concentrated. Flash chromatography on silica gel (20% ethyl acetate in dichloromethane) gave 0. 105 g of the desired product as a white solid.

EXAMPLE 18B

N-(1-(((4'-butoxy(1,1'-biphenyl)-4-yl)oxy)methyl)-2-(3,4,4-trimethyl-2,5-dioxo-1-imidazolidinyl)ethyl)-N-hydroxyformamide The desired product was prepared as in Example 2D,E,F substituting Example 18A for Example 2C.

$^1$H NMR (300 MHz, d$_6$-DMSO) δ 9.87 (s, 0.5H), 9.55 (s, 0.5H), 8.31 (s, 0.5H), 7.91 (s, 0.5H), 7.55–7.50 (m, 8H), 6.98–6.95 (m, 8H), 4.80–4.60 (m, 0.5H), 4.50–4.35 (m, 0.5H), 4.16–4.06 (m, 4H), 4.01–3.96 (t, 4H, J=7.0, 5.9 Hz), 3.76–3.70 (m, 2H), 3.62–3.59 (m, 2H), 2.80 (s, 6H), 1.72–1.65 (m, 4H), 1.48–1.40 (m, 4H), 1.29 (s, 12H), 0.96–0.91 (t, 6H, J=7.1, 7.5 Hz);

MS (ESI) m/e M+H (484), M+NH$_4$ (506);

Anal. Calcd for: C$_{26}$H$_{33}$N$_3$O$_6$: C, 64.57; H, 6.87; N, 8.68. Found: C, 64.70; H, 7.04; N, 8.50.

EXAMPLE 19

N-(1-(((4'-fluoro(1,1'-biphenyl)-4-yl)oxy)methyl)-2-(3,4,4-trimethyl-2,5-dioxo-1-imidazolidinyl)ethyl)-N-hydroxyformamide

EXAMPLE 19A 3-(3,4,4-trimethyl-2,5-dioxo-1-imidazolidinyl)-propan-(1,2)oxirane The desired product was prepared following the procedures described for Example 5A and 5C, substituting allyl alcohol for 3-buten-1-ol.

EXAMPLE 19B

N-(1-(((4'-fluoro(1,1'-biphenyl)-4yl)oxy)methyl)-2-(3,4,4-trimethyl-2,5-dioxo-1-imidazolidinyl)methyl)-N-hydroxyformamide The desired product was prepared according to the sequence of reactions described in Examples 5D through 5H, substituting Example 19A for 5C in Example 5D and 4-(4'-fluorophenyl)-phenol for 4'-hydroxy-4-biphenyl carbonitrile in Example 5F.

$^1$H NMR (300 MHz, d$_6$-DMSO) δ 9.86 (S, 0.5H), 9.54 (S, 0.5H), 8.31 (S, 0.5H), 7.91 (S, 0.5H), 7.67–7.57 (M, 6H), 7.27–7.22 (M, 3H), 7.01–6.97 (M, 3H), 4.96–4.70 (M, 0.5H), 4.50–4.40 (M, 0.5H), 4.18–4.08 (M, 3H), 3.77–3.73 (M, 21), 2.79 (S, 6H), 1.28 (S, 12H).

MS (ESI) m/e 430 (M+H), 428 (M–H);

Anal. Calcd for: C$_{22}$H$_{24}$N$_3$O$_5$F.0.5H$_2$O: C, 60.26; H, 5.74; N, 9.58. Found: C, 60.48; H, 5.66; N, 8.72.

EXAMPLE 20

N-(1-((3,4,4-trimethyl-2,5-dioxo-1-imidazolidinyl)methyl)-2-((4'-(trifluoromethyl)(1,1'-biphenyl)-4-yl)oxy)ethyl)-N-hydroxyformamide The desired product was prepared according to the sequence of reactions described in Examples 5D through 5H, substituting 19A for 5C in Example 5D and substituting 4-(4'-trifluoromethylphenyl)phenol for 4'-hydroxy-4-biphenyl carbonitrile in Example 5F.

$^1$H NMR (300 MHz, d$_6$-DMSO) δ 9.80 (S, 0.5H), 9.58 (S, 0.5H), 8.32 (S, 0.5H), 7.92 (S, 0.5H), 7.87–7.84 (D, 4H, J=8.1 Hz), 7.79–7.76 (D, 4H, J=8.8 Hz), 7.72–7.69 (d, 4H, J=8.4 Hz), 7.06–7.02 (m, 4H), 4.80–4.60 (m, 0.5H), 4.45–4.40 (m, 0.5H), 4.20–4.12 (m, 4H), 3.78–3.74 (m, 2H), 3.63–3.62 (m, 2H), 2.08 (s, 6H), 1.30 (s, 12H);

MS (ESI) m/e M–H (478), M+H (480);

Anal. Calcd for: C$_{23}$H$_{24}$N$_3$O$_5$F$_3$.0.5H$_2$O: C, 56.55; H, 5.15; N, 8.60. Found: C, 56.52; H, 5.07; N, 8.43.

EXAMPLE 21

N-(1-(((4'-methoxy(1,1'-biphenyl)-4-yl)oxy)methyl)-2-(3,4,4-trimethyl-2,5-dioxo-1-imidazolidinyl)ethyl)-N-hydroxyformamide The desired product was prepared according to the sequence of reactions described in Examples 5D through 5H, substituting 19A for 5C in Example 5D and substituting 4-(4'-methoxyphenyl)phenol for 4'-hydroxy-4-biphenyl carbonitrile in Example 5F.

$^1$H NMR (300 MHz, d$_6$-DMSO) δ 9.89 (s, 0.5H), 9.57 (s, 0.5H), 8.31 (s, 0.5H), 7.91 (s, 0.51H), 7.56–7.53 (d, 8H, J=8.8 Hz), 7.01–6.94 (m, 8H), 4.80–4.60 (m, 0.5H), 4.44–4.35 (m, 0.5H), 4.17–3.95 (m, 4H), 3.74–3.71 (m, 2H), 3.63–3.58 (m, 2H), 2.79 (s, 6H), 1.28 (s, 12H);

MS (ESI) m/e M+H (442);

Anal. Calcd for: C$_{23}$H$_{26}$N$_3$O$_6$.0.25H$_2$O: C, 62.08; H, 6.00; N, 9.44. Found: C, 62.25; H, 6.30; N, 8.94.

EXAMPLE 22

N-(1-(((4'-methyl(1,1'-biphenyl)-4-yl)oxy)methyl)-2-(3,4,4-trimethyl-2,5-dioxo-1-imidazolidinyl)ethyl)-N-hydroxyformamide The desired product was prepared according to the sequence of reaction described in Examples 5D through 5H, substituting 19A for 5C in Example 5D and substituting 4-(4'-methylphenyl)phenol for 4'-hydroxy-4-biphenyl carbonitrile in Example 5F.

$^1$H NMR (300 MHz, d$_6$-DMSO) δ 9.89 (s, 0.5H), 9.57 (s, 0.5H), 8.31 (s, 0.5H), 7.92 (s, 0.5H), 7.59–7.56 (d, 4H, J=8.8 Hz), 7.52–7.49 (d, 4H, J=8.1 Hz), 7.24–7.22 (d, 4H, J=7.7 Hz), 7.00–6.97 (m, 4H), 4.80–4.60 (m, 0.5H), 4.40–4.35 (m, 0.5H), 4.40–4.1 (m, 4H), 3.80–3.55 (m, 2H), 3.60–3.50 (m, 2H), 2.79 (s, 6H), 2.32 (s, 6H), 1.28 (s, 12H);

MS (ESI) m/e 424 (M–H), 426 (M+H);

Anal. Calcd for: C$_{23}$H$_{27}$N$_3$O$_5$.0.25H$_2$O: C, 64.24; H, 6.44; N, 9.77. Found: C, 64.30; H, 1915 6.55; N, 9.36.

EXAMPLE 23

N-(1-(((4'-butoxy(1,1'-biphenyl)-4-yl)oxy)methyl)-2-(4,4-dimethy-2,5-dioxo-1-imidazolidinyl)ethyl)-N-hydroxyformamide

EXAMPLE 23A 1-bromo-3-(4,4-dimethyl-2,5-dioxoimidazolidin-1-yl)propan-2-one

The desired product was prepared following the procedure desribed in Examples 16A and 16 B, substituting 5,5 dimethylhydantoin for 1,5,5 trimethylhydantoin in Example 16A.

EXAMPLE 23B

N-(1-(((4'-butoxy(1,1'-biphenyl)-4-yl)oxy)methyl)-2-(4,4-dimethy-2,5-dioxo-1-imidazolidinyl)ethyl)-N-hydroxyformamide The desired product was prepared according to the procedures of Example 16C and 16E, substituting Example 23A for 16B and 4-(4'-Butyloxyphenyl)phenol for 4-bromophenol in Example 16C.

$^1$H NMR (300 MHz, d$_6$-DMSO) δ 9.86 (s, 0.5H), 9.55 (s, 0.5H), 8.36 (s, 0.5H), 8.34 (s, 0.5H), 8.32 (s, 0.5H), 7.94 (s, 0.5H), 7.55–7.51 (m, 8H), 6.99–6.96 (m, 8H), 4.85–4.80 (m, 1935 0.5H), 4.40–4.36 (m, 0.5H), 4.204.06 (mm, 2H), 4.01–3.97 (m, 4H), 3.78–3.71 (m, 2H), 3.60–3.51 (m, 2H), 1.73–1.66 (m, 6H), 1.48–1.38 (m, 4H), 1.25 (s, 12H), 0.96–0.86 (m, 6H);

MS (ESI) m/e M–H (468);

Anal. Calcd for: C$_{25}$H$_{30}$N$_3$O$_6$: C, 63.95; H, 6.65; N, 8.94. Found: C, 63.89; H, 6.91; N, 8.63.

EXAMPLE 24

N-(1-((4,4-dimethy-2,5-dioxo-1-imidazolidinyl)methyl)-2-((4'-ethoxy(1,1'-biphenyl)-4-yl)oxy)ethyl)-N-hydroxyformamide The desired product was prepared according to the procedures of Example 23B, substituting 4-(4'-ethoxyphenyl)phenol for 4-(4'-Butyloxyphenyl)phenol.

$^1$H NMR (300 MHz, d$_6$-DMSO) δ 9.84 (s, 0.5H), 9.52 (s, 0.5H), 8.37 (s, 0.5H), 8.32 (s, 2H), 7.92 (s, 0.5H), 7.55–7.52 (m, 8H), 6.98–6.95 (d, 4H, J=8.8 Hz), 4.90–4.80 (m, 0.5H), 4.45–4.30 (m, 0.5H), 4.19–3.98 (m, 8H), 3.74–3.67 (m, 2H), 3.59–3.53 (m, 2H), 1.36–1.25 (m, 18H);

MS (ESI) m/e M–H (440), M+H (442);

Anal. Calcd for: C$_{23}$H$_{27}$N$_3$O$_6$.0.5H$_2$O: C, 61.32; H, 6.26; N, 9.32. Found: C, 61.12; H, 6.35; N, 9.32.

EXAMPLE 25

N-(1-((4-(1,3-benzodioxol-5-yl)phenoxy)methyl)-2-(4,4-dimethy-2,5-dioxo-1-imidazolidinyl)ethyl)-N-hydroxyformamide The desired product was prepared according to the procedures of Example 23B, substituting 4-(3',4'-methylenedioxyphenyl)-phenol for 4-(4'-butyloxyphenyl)phenol.

$^1$H NMR (300 MHz, d$_6$-DMSO) δ 9.84 (s, 0.5H), 9.52 (s, 0.5H), 8.37–8.31 (m, 3H), 7.91 (s, 0.5H), 7.55–7.52 (d, 4H, J=8.5 Hz), 7.19 (s, 2H), 7.09–7.06 (m, 2H), 6.97–6.93 (d, 6H, J=10.2 Hz), 6.03 (s, 4H), 4.70–4.60 (m, 0.5H), 4.45–4.30 (m, 0.5H), 4.16–3.96 (s, 6H), 3.73–3.57 (m, 5H), 1.27 (s, 12H);

MS (ESI) m/e M+H (442), M–H (440);

Anal. Calcd for: C$_{22}$H$_{23}$N$_3$O$_7$.0.50H$_2$O: C, 58.66; H, 5.37; N, 9.32. Found: C, 58.70; H, 5.80; N, 8.79.

EXAMPLE 26

N-(1-(((4'-butoxy(1,1'-biphenyl)-4-yl)oxy)methyl)-2-(3-methy-2,5-dioxo-1-imidazolidinyl)ethyl)-N-hydroxyformamide

EXAMPLE 26A 1-bromo-3-(3-methyl-2,5-dioxoimidazolidin-1-yl)propan-2-one

The desired product was prepared following the procedure desribed in Examples 16A and 16 B, substituting 1-methylhydantoin for 1,5,5 trimethylhydantoin in Example 16A.

EXAMPLE 26B

N-(1-(((4'-butoxy(1,1'-biphenyl-4-yl)oxy)methyl)-2-(3-methy-2,5-dioxo-1-imidazolidinyl)ethyl)-N-hydroxyformamide The desired product was prepared according to the procedures of Example 16C and 16E, substituting Example 26A for 16B and 4-(4'-butyloxyphenyl)phenol for 4-bromophenol in Example 16C.

$^1$H NMR (300 MHz, d$_6$-DMSO) δ 9.97 (s, 0.5H), 9.60 (s, 0.5H), 8.34 (s, 0.5H), 7.97 (s, 0.5H), 7.55–7.50 (m, 8H), 6.99–6.91 (m, 8H), 4.86–4.82 (m, 0.5H), 4.334.31 (m, 0.5H), 4.18–4.12 (m, 2H), 3.99–3.94 (m, 4H), 2.85 (s, 6H), 1.82–1.68 (m, 4H), 1.50–1.38 (m, 6H), 0.96–0.91 (m, 6H);

MS (ESI) m/e M–H (454);

Anal. Calcd for: C$_{24}$H$_{29}$N$_3$O$_6$.0.25C$_4$H$_5$O: C, 63.51; H, 6.44; N, 8.88. Found: C, 63.59; H, 6.46; N, 8.68.

EXAMPLE 27

N-(1-((4-(3-thienyl)phenoxy)ethyl)-2-(3,4,4-trimethyl-2,5-dioxo-1-imidazolidinyl)ethyl)-N-hydroxyformamide The desired product was prepared according to the procedures of Example 16C and 16E, substituting 4-(4'-(3-thienyl)phenyl)phenol for 4-bromophenol in Example 16C.

$^1$H NMR (300 MHz, d$_6$-DMSO) δ 9.90 (s, 0.5H), 9.57 (s, 0.5H), 8.31 (s, 0.5H), 7.91 (s, 0.5H), 7.75–7.74 (m, 2H), 7.67–7.60 (m, 6H), 7.52–7.49 (m, 2H), 6.96–6.92 (m, 4H), 4.80–4.6 (m, 0.5H), 4.50–4.4 (m, 0.5H), 4.19–3.98 (m, 6H), 3.81–3.70 (m, 2H), 3.61–3.56 (m, 2H), 2.79 (s, 6H), 1.29 (s, 12H);

Anal. Calcd for: C$_{20}$H$_{23}$N$_3$O$_5$S: C, 57.54; H, 5.55; N, 10.06. Found: C, 57.72; H, 5.84; N, 9.76.

EXAMPLE 28

N-(1-((((1,1'-biphenyl)-4-yl)oxy)ethyl)-2-(3,4,4-trimethyl-2,5-dioxo-1-imidazolidinyl)ethyl)-N-hydroxyformamide The desired product was prepared according to the procedures of Example 16C and 16E, substituting 4-phenylphenol for 4-bromophenol in Example 16C.

$^1$H NMR (300 MHz, d$_6$-DMSO) δ 9.90 (S. 0.5H), 9.57 (S, 0.5H), 8.30 (S, 0.5H), 7.92 (S, 0.5H), 7.62–7.60 (D, 8H, J=8.1 Hz), 7.45–7.40 (t, 4H, J=5.8, 7.8 Hz), 7.33–7.28 (t, 2H, J=7.1, 6.9 Hz), 7.02–6.97 (m, 4H), 4.80–4.60 (m, 0.5H), 4.45–4.40 (m, 0.5H), 4.18–4.01 (m, 4H), 3.77–3.70 (m, 2H), 3.63–3.6 (m, 2H), 2.80 (s, 6H), 1.28 (s, 12H);

MS (ESI) m/e M–H (410), M+H (412);

Anal. Calcd for: C$_{22}$H$_{25}$N$_3$O$_5$.0.25H$_2$O: C, 63.25; H, 6.17; N, 10.10. Found: C, 63.94; H, 6.41; N, 9.60.

EXAMPLE 29

N-(1-(((3'-chloro-4'-fluoro(1,1'-biphenyl)-4-yl)oxy)methyl)-2-(3,4,4-trimethyl-2,5-dioxo-1-imidazolidinyl)ethyl)-N-hydroxyformamide The desired product was prepared according to the procedures of Example 16C and 16E, substituting 4-(4'-fluoro-3'-chloro-phenyl)phenol for 4-bromophenol in Example 16C.

$^1$H NMR (300 MHz, d$_6$-DMSO) δ 9.90 (s, 0.5H), 9.57 (s, 0.511), 8.31 (s, 0.5H), 7.92 (s, 0.5H), 7.84–7.82 (m, 2H), 7.65–7.61 (m, 6H), 7.49–7.43 (t, 2H, J=9.2,8.8 Hz), 7.02–6.96 (m, 4H), 4.80–4.60 (m, 0.5H), 4.43–4.40 (m, 0.5H), 4.21–4.06 (m, 4H), 3.82–3.70 (m, 2H), 3.62–3.59 (m, 2H), 2.79 (s, 6H), 1.28 (s, 12H);

MS (ESI) m/e M–H (462), M+H (464);

Anal. Calcd for: C$_{22}$H$_{23}$N$_3$O$_5$ClF.0.25H$_2$O: C, 56.41; H, 5.05; N, 8.97. Found: C, 56.78; H, 5.24; N, 8.55.

EXAMPLE 30

N-(1-(((2'-methyl(1,1'-biphenyl)-4yl)oxy)methyl)-2-(3,4,4-trimethy-2,5-dioxo-1-imidazolidinyl)ethyl)-N-hydroxyformamide The desired product was prepared according to the procedures of Example 16C and 16E, substituting 4-(3'-methyl-phenyl)phenol for 4-bromophenol in Example 16C.

$^1$H NMR (300 MHz, d$_6$-DMSO) δ 9.90 (s, 0.5H), 9.57 (s, 0.5H), 8.32 (s, 0.5H), 7.93 (s, 0.5H), 7.28–7.14 (mm, 12), 6.99–6.64 (m, 4H), 4.90–4.80 (m, 0.5H), 4.42–4.40 (m, 0.5H), 4.22–4.04 (m, 6H), 3.82–3.74 (m, 2H), 3.62–3.58 (m, 2H), 2.80 (s, 6H), 2.20 (s, 6H), 1.29 (s, 12H);

MS (ESI) m/e M+H (426), M−H (424);

Anal. Calcd for: C$_{23}$H$_{27}$N$_3$O$_5$.0.25H$_2$O: C, 64.24; H, 6.44; N, 9.77. Found: C, 64.50; H, 6.69; N, 9.31.

EXAMPLE 31

N-(1-(((4'-cyanol(1,1'-biphenyl)-4-yl)oxy)methyl)-2-(2,5-dioxo-1-imidazolidinyl)ethyl)-N-hydroxyformamide

EXAMPLE 31A 3-(4-(4'-carbonitrilephenyl)phenoxy)-1-bromopropan-2-one

The desired product was prepared according to the procedure described in Examples 16A and 16B, substituting 4-(4'-cyanophenyl)-phenol for 1,5,5-trimethyl hydantoin in Example 16A.

EXAMPLE 31B

N-(1-(((4'-cyanol(1,1'-biphenyl)-4-yl)oxy)methyl)-2-(2,5-dioxo-1-imidazolidinyl)ethyl)-N-hydroxyformamide The desired product was prepared according to the procedures of Example 16C and 16E, substituting Example 31A for 16B and hydantoin for 4-bromophenol in Example 16C.

$^1$H NMR (300 MHz, DMSO-d$_6$) δ 3.6–3.8 (m, 2H), 3.92 (d, 2H, J=8.4 Hz), 4.10–4.25 (m, 2H), 4.3–4.4 (m, 0.5H), 4.8–4.9 (m, 0.5H), 7.07.1 (m, 2H), 7.74 (d, 2H, J=9.0 Hz), 7.84 (d, 2H, J=8.4 Hz), 7.89 (d, 2H, J=8.4 Hz), 7.98 (s, 0.5H), 8.1–8.2 (m, 1H), 8.35 (s, 0.5H), 9.57 (br s, 0.5H), 9.53 (br s, 0.5H);

MS (ESI+) 395 (M+H);

Anal. Calcd for C$_{20}$H$_{18}$N$_4$O$_5$.0.2H$_2$O.0.4EtOAc: C, 59.88; H, 5.03; N, 12.93. Found: C, 59.80; H, 4.81; N, 12.74.

EXAMPLE 32

N-(1-(((4'-cyanol(1,1'-biphenyl)-4-yl)oxy)methyl)-2-(1,1-dioxido-3-oxo-1,2-benzisothiazol-2(3H)-yl)ethyl)-N-hydroxyformamide The desired product was prepared according to the procedures of Example 16C and 16E, substituting Example 31A for Example 16B and saccharin for 4-bromophenol in Example 16C.

$^1$H NMR (300 MHz, DMSO-d$_6$) δ 3.9–4.2 (m, 2H), 4.2–4.3 (m, 2H), 4.454.55 (m, 0.5H), 5.0–5.1 (m, 0.5H), 7.0–7.1 (m, 2H), 7.74 (d, 2H, J=8.4 Hz), 7.85 (d, 2H, J=8.7 Hz), 7.88 (d, 2H, J=8.4 Hz), 8.0–8.2 (m, 3.5H), 8.3–8.4 (m, 1.5H), 9.78 (s, 0.5H), 10.14 (s, 0.5H).

MS (ESI−) 476 (M−H);

Anal. Calcd for C$_{24}$H$_{19}$N$_3$O$_6$S.1.1H$_2$O: C, 57.97; H, 4.30; N, 8.45. Found: C, 58.01; H, 3.96; N, 8.16.

EXAMPLE 33

N-(1-((4,4-dimethy-2,5-dioxo-1-imidazolidinyl)methyl)-2-((4'-(trifluoromethoxy)(1,1'-biphenyl)-4-yl)oxy)ethyl)-N-hydroxyformamide The desired product was prepared according to the procedures of Example 23B, substituting 4-(4'-trifluoromethoxy phenyl)-phenol for 4(4'-butyloxyphenyl)-phenol.

$^1$H NMR (300 MHz, DMSO-d$_6$) δ 1.27 (s, 6H), 3.5–3.8 (m, 2H), 4.0–4.3 (m, 2H), 4.4–4.5 (m, 0.5H), 4.8–4.9 (m, 0.5H), 7.0–7.2 (m, 2H), 7.42 (d, 2H, J=7.8 Hz), 7.64 (d, 2H, J=8.4 Hz), 7.75 (d, 2H, J=8.7 Hz), 7.93 (s, 0.5H), 8.33 (s, 0.5H), 8.35 (s, 0.5H), 8.40 (s, 0.5H), 9.56 (s, 0.5H), 9.87 (s, 0.511);

MS (ESI+) 482 (M+H);

Anal. Calcd for C$_{22}$H$_{21}$N$_3$O$_6$F$_3$: C, 54.88; H, 4.60; N, 8.72. Found: C, 55.22; H, 4.87; N, 8.36.

EXAMPLE 34

N-(1-((4-(4-phenyl-1-piperidinyl)phenoxy)methyl)-2-(3,4,4-trimethyl-2,5-dioxo-1-imidazolidinyl)ethyl)-N-hydroxyformamide The desired product was prepared according to the procedures of Example 16C and 16E, substituting the 4-phenyl-N-phenyl piperidine (prepared as in Warner-Lambert patent WO 97/19068), for 4-bromophenol in Example 16C.

$^1$H NMR (300 MHz, DMSO-d$_6$) δ 1.27 (s, 3H), 1.28 (s, 3H), 1.7–1.9 (m, 4H), 2.55–2.75 (m, 3H), 2.78 (s, 1.5H), 2.79 (s, 1.5H), 3.5–3.8 (m, 4H), 3.9–4.1 (m, 2H), 4.3–4.4 (m, 0.5H), 4.7–4.8 (m, 0.5H), 6.81 (d, 2H, J=8.7 Hz), 6.93 (d, 2H, J=9.0 Hz), 7.15–7.25 (m, 1H), 7.25–7.35 (m, 4H), 7.89 (s, 0.5H), 8.30 (s, 0.5H), 9.54 (s, 0.5H), 9.86 (s, 0.5H);

MS (ESI+) 495 (M+H);

Anal. Calcd for C$_{27}$H$_{34}$N$_4$O$_5$: C, 65.56; H, 6.92; N, 11.32. Found: C, 65.35; H, 7.24; N, 10.93.

EXAMPLE 35

N-(1-((4,4-dimethy-2,5-dioxo-1-imidazolidinyl)methyl)-2-((4'-(trifluoromethyl)(1,1'-biphenyl)-4-yl)oxy)ethyl)-N-hydroxyformamide The desired product was prepared according to the procedures of Example 23B, substituting 4-(4'-trifluoromethylphenyl)phenol for 4-(4'-butyloxyphenyl) phenol.

$^1$H NMR (300 MHz, DMSO-d$_6$) δ 1.28 (s, 6H), 3.5–3.8 (m, 2H), 4.1–4.3 (m, 2H), 4.4–4.5 (m, 0.5H), 4.8–4.9 (m, 0.5H), 7.0–7.2 (m, 2H), 7.72 (d, 2H, J=8.4 Hz), 7.78 (d, 2H, J=8.4 Hz), 7.86 (d, 2H, J=8.4 Hz), 7.93 (s, 0.5H), 8.33 (s, 0.5H), 8.35 (s, 0.5H), 8.40 (s, 0.5H), 9.56 (s, 0.5H), 9.87 (s, 0.5H);

MS (ESI+) 466 (M+H);

Anal. Calcd for C$_{22}$H$_{22}$N$_3$O$_5$F$_3$.0.6H$_2$O: C, 55.49; 1, 4.91; N, 8.82. Found: C, 55.55; H, 4.66; N, 8.77.

EXAMPLE 36

N-(1-(((3'-cyano(1,1'-biphenyl)-4-yl)oxy)methyl)-2-(methyl((4-methylphenyl)sulfonyl)amino)ethyl)-N-hydroxyformamide The desired product was prepared according to the procedures of Example 16C and 16E, substituting Example 31A for Example 16B and N-methyl-(p-tolyl)sulfonamide for 4-bromophenol in Example 16C.

$^1$H NMR (300 MHz, DMSO-d$_6$) δ 2.41 (s, 3H), 2.70 (s, 1.5H), 2.73 (s, 1.5H), 3.05–3.35 (m, 2H), 4.0–4.2 (m, 2H), 4.3–4.4 (m, 0.5H), 4.8–4.9 (m, 0.5H), 7.06 (d, 2H, J=8.7 Hz), 7.46 (d, 2H, J=8.1 Hz), 7.65–7.8 (m, 4H), 7.85 (d, 2H, J=8.7 Hz), 7.89 (d, 2H, J=8.7 Hz), 8.04 (s, 0.5H), 8.40 (s, 0.5H), 9.71 (s, 0.5H), 10.0 (s, 0.5H);

MS (ESI+) 480 (M+H);

Anal. Calcd for $C_{25}H_{25}N_3O_5S$: C, 62.61; H, 5.25; N, 8.76. Found: C, 62.52; H, 5.27; N, 7.98.

EXAMPLE 37

N-(1-(((4'-cyano(1,1'-biphenyl)-4-yl)oxy)methyl)-2-(4,4-dimethy-2,5-dioxo-3-(3-pyridinylmethyl)-1-imidazolidinyl)ethyl)-N-hydroxyformamide

EXAMPLE 37A 3-(3-pyridinylmethyl))-2,5-dioxo-4,4-dimethylimidazolidine

The desired product was prepared following the procedures described in Examples 68A, 68B and 69B, substituting 3-picolyl chloride for methyl iodide in Example 68B.

EXAMPLE 37B

N-(1-(((4'-cyano(1,1'-biphenyl)-4-yl)oxy)methyl)-2-(4,4-dimethy-2,5-dioxo-3-(3-pyridinylmethyl)-1-imidazolidinyl)ethyl)-N-hydroxyformamide The desired product was prepared according to the procedures of Example 16C and 16E, substituting Example 31A for Example 16B and Example 37A for 4-bromophenol in Example 16C.

$^1$H NMR (300 MHz, DMSO-$d_6$) δ 1.25 (s, 6H), 3.6–3.7 (m, 1H), 3.8–3.9 (m, 1H), 4.1–4.3 (m, 2H), 4.4–4.5 (m, 0.5H), 4.56 (s, 2H), 4.85–4.95 (m, 0.5H), 7.0–7.1 (m, 2H), 7.35 (dd, 1H, J=8.1,4.8 Hz), 7.7–7.8 (m, 3H), 7.86 (d, 2H, J=8.4 Hz), 7.90 (d, 2H, J=8.4 Hz), 7.96 (s, 0.5H), 8.34 (s, 0.5H), 8.45–8.50 (narrow m, 1H), 8.60 (s, 1H), 9.64 (s, 0.5H), 9.97 (s, 0.5H);

MS (ESI(+)) 514 (M+H);

Anal. Calcd for $C_{28}H_{27}N_5O_5 \cdot 1.7H_2O$: C, 61.80; H, 5.63; N, 12.87. Found: C, 61.77; H, 5.08; N, 12.48.

EXAMPLE 38

N-(2-((4'-cyano(1,1'-biphenyl)-4-yl)oxy)-1-methylpropyl)-N-hydroxyformamide

The desired product was prepared according to the procedures of Example 16C and 16E, substituting 3-bromo-2-butanone for Example 16B and 4-(4'-cyanophenyl)phenol for 4-bromophenol in Example 16C.

$^1$H NMR (300 MHz, DMSO-$d_6$) δ 1.1–1.3 (m, 6H), 3.8–4.0 (m, 11H), 4.3–4.7 (m, 11H), 7.0–7.1 (m, 2H), 7.8–7.7 (m, 2H), 7.8–7.9 (m, 4H), 8.02 (s, 0.5H), 8.28 (s, 0.25H), 8.33 (s, 0.25H), 9.43 (s, 0.25H), 9.60 (s, 0.25H), 9.85 (s, 0.25H), 9.95 (s, 0.25H). MS (ESI+) 311 (M+H). Anal. Calcd for $C_{18}H_{18}N_2O_3 \cdot 0.2H_2O$: C, 68.86; H, 5.91; N, 8.92. Found: C, 68.73; H, 5.79; N, 8.58.

EXAMPLE 39

N-(1-(((3'-cyano(1,1'-biphenyl)-4-yl)oxy)methyl)-2-(3,4,4-trimethyl-2,5-dioxo-1-imidazolidinyl)ethyl)-N-hydroxyformamide

EXAMPLE 39A

3'-cyano-4-hydroxy Biphenyl

A 250 mL flask was charged with 2.21 g (2.7 mmol) (1,1'-bis(diphenylphosphino) ferrocene) dichloropalladium (II)·dichloromethane, 6.26 g (2.73 mmol) 3-iodobenzonitrile, 6.0 g (3.95 mmol) 4-methoxyphenylboronic acid, and 12.45 g (8.20 mmol) cesium fluoride, followed by the addition of 180 mL 1,2-dimethoxyethane. The flask was flushed with $N_2$ and the suspension heated to reflux which was maintained for 3 hours. The reaction mixture was cooled to room temperature, filtered through a pad of 300 g flash silica gel, and the pad was washed with 1 L ethyl acetate. The ethyl acetate was concentrated and the residue purified by flash chromatography on silica gel eluting with 10% hexanes/90% ethyl acetate to give 3.3 g of the desired product (58% yield). This material was dissolved in 50 mL anhydrous dichloromethane and the solution cooled in a dry ice-acetone bath and a solution of boron tribromide (40 mL, 4 mmol) was added dropwise under inert atmosphere. The reaction was then stirred at room temperature overnight. The solution was cooled in an ice bath and 5 mL of $H_2O$ was added dropwise, followed by the addition of 20 mL 1N HCl. The mixture was stirred for 1 hour and the resulting suspension was filtered and the filtrate transferred to a separatory funnel and the organic layer separated off and set aside. The filtered solid was washed with $H_2O$ and ethyl acetate and filtered and the filtrate transferred to the separatory funnel and the organic layer combined with the previous organic layer, dried over $Na_2SO_4$, filtered and the filtrate concentrated to provide 3.05 g of the desired product (99% yield).

EXAMPLE 39B

N-(1-(((3'-cyano(1,1'-biphenyl)-4-yl)oxy)methyl)-2-(3,4,4-trimethyl-2,5-dioxo-1-imidazolidinyl)ethyl)-N-hydroxyformamide The desired product was prepared according to the procedures of Example 16C and 16E, substituting 3'cyano-4-hydroxy biphenyl for 4-bromophenol in Example 16C.

mp: 130–132° C.;

$^1$H NMR (DMSO-$d6$) δ 9.86 (s, ½H), 9.48–9.63 (c, ½H), 8.33 (s, ½H), 8.09 (s, 1H), 7.97 (d, 1H, J=4.5 Hz), 7.93 (s, ½H), 7.75 (d, 1H, J=4.5 Hz), 7.70 (d, 2H, J=6.0 Hz), 7.63 (t, 1H, J=4.5 Hz), 7.00–7.07 (c, 2H), 4.83–4.90 (c, ½H), 4.60–4.67 (c, ½H);

ESI(+): 409 (M-27), 437 (M+H), 454 (M+NH$_4$), 459 (M+Na);

Anal. Calcd for: $C_{23}H_{24}N_4O5 \cdot 0.25C_4H_8O_2$: C, 62.87; H, 5.71; N, 12.21. Found: C, 62.68; H, 5.55; N, 12.27.

EXAMPLE 40

N-(1-(((4'-(methlthio)(1,1'-biphenyl)-4-yl)oxy)methyl)-2-(3,4-trimethyl-2,5-dioxo-1-imidazolidinyl)ethyl)-N-hydroxyformamide The desired product was prepared according to the procedures of Example 16C and 16E, substituting 4'-thiomethyl-4-hydroxy biphenyl for 4-bromophenol in Example 16C.

mp 172–174.

1H NMR (DMSO-δ6) δ 9.48–9.96 (BS, 1H), 8.34 (S, ½H), 7.94 (S, ½H), 7.54–7.63 (C, 4H), 7.29–7.34 (C, 2H), 6.97–7.03 (C, 2H), 4.82 4.92 (C, ½H), 4.39–4.47 (C, ½H), 4.07–4.25 (C, 2H), 3.73–3.85 (C, 1H), 3.59–3.68 (C, 1H), 2.80 (S, 1.5H), 2.79 (S, 1.5H)

MS (ESI(–)) 456 ((M–H)), 913 ((2M–H)) Calcd: 458.175 Found: 458.1747;

Anal. Calcd for: $C_{23}H_{27}N_3O_5S$ C, 60.37; H, 5.95; N, 9.19; S, 7.01 Found: C, 60.29; H, 5.82; N, 9.08; S, 6.98.

EXAMPLE 41

N-(1-(4-((4-(trifluoromethyl)phenoxy)phenoxy)methyl)-2-(3,4,4-trimethyl-2,5-dioxo-1-imidazolidinyl)ethyl)-N-hydroxyformamide The desired product was prepared according to the procedures of Example 16C and 16E, substituting 4-(4'-trifluoromethylphenoxy)phenol for 4-bromophenol in Example 16C.

mp 121–123

1H NMR (DMSO-d6) δ 9.46–9.97 (C, 1H), 8.33 (S, ½H), 7.94 (S, ½H), 7.71 (S, 1H), 7.69 (S, 1H), 7.04–7.14 (C, 4H), 6.97–7.03 (C, 2H), 4.81–4.91 (C, ½H), 4.39–4.47 (C, ½H), 4.14–4.22 (C, 1H), 4.04–4.13 (C, 1H), 2.81 (S, 1.5H), 2.80 (S, 1.5H), 1.30 (S, 1.5H);

MS (ESI(–)) 494 (M–H), 530 (M+Cl), 989 (2M–H), 1011 (2M+Na$_2$H) Calcd: 496.169, Found: 496.1696;

Anal. Calcd for: $C_{23}H_{24}N_3O_6$ Theory: C, 55.75; H, 4.88; N, 8.48; F, 11.50. Found: C, 55.68; H, 4.92; N, 8.40; F, 11.24.

EXAMPLE 42

N-(1-(((4'-(trifluoromethoxy)(1,1'-biphenyl)-4-yl)oxy)methyl)-2-(3,4,4-trimethy-2,5-dioxo-1-imidazolidinyl)ethyl)-2-N-hydroxyformamide The desired product was prepared according to the procedures of Example 16C and 16E, substituting 4'-trifluoromethoxy-4-hydroxy biphenyl for 4-bromophenol in Example 16C.

mp 129.3–130° C.;

$^1$H NMR, 400 Mz (DMSO-d6): δ 9.46–9.84 (c,1H), 8.26 (s,½H), 7.87 (s,½H), 7.67 (s,1H), 7.65 (s,1H), 7.57 (s,1H), 7.55 (s,1H), 7.34 (s,1H), 7.32 (s,1H), 6.94–6.97 (c,2H), 4.78–4.82 (c,½H), 4.34–4.38 (c,½H), 4.02–4.17 (c,2H), 3.67–3.77 (c,1H), 3.53–3.60 (c,1H), 2.73 (s,1.5H), 2.72 (s,1.5H), 1.22 (s,3H), 1.21 (s,3H);

MS (ESI(–)): 494 (M–H), 530 (M+Cl), 989 (2M–H), 1011 (2M+Na–2H) Calcd.: 496.1695 Found: 496.1680;

Anal. Calcd. for $C_{23}H_{24}F_3N_3O_6$ Theory: C,55.75; H, 4.88; N, 8.48; F, 11.50. Found: C, 55.69; H, 4.94; N, 8.23; F, 11.71.

EXAMPLE 43

N-(1-(((4'-(methylsulfonyl)(1,1'-biphenyl)-4-yl)oxy)methyl)-2-(3,4,4-trimethy-2,5-dioxo-1-imidazolidinyl)ethyl)-N-hydroxyformamide The desired product was prepared according to the procedures of Example 48A, 48B and 48C, substituting Example 16B for Example 23A for 4bromophenol in Example 48A.

mp 174–175° C.;

$^1$H NMR, 400 MHz (DMSO-d6): δ 9.47–9.98 (c, 1H), 8.35 (s, ½H), 7.92–8.00 (c, 4.5H), 7.77 (s, 1H), 7.75 (s, 1H), 7.07–7.10 (c, 2H), 4.85–4.94 (c, ½H), 4.42–4.50 (½H), 4.13–4.30 (c, 2H), 3.76–3.86 (c, 1H), 3.63–3.69 (c, 1H), 3.39 (s, 3H), 2.83 (s, 1.5H), 2.82 (s, 1.5H), 1.32 (s, 3H), 1.31 (s,3H);

MS (ESI(–)): 488(M–H), 977(2M–H), 999(2M+Na–2H) (ESI(+)): 490 (M+H), 507 (M+NH$_4$), 512 (M+Na);

Anal. calcd. for $C_{23}H_{28}.5N_3O_7S$: Theory: C, 54.91; H, 5.71; N, 8.35;S, 6.37 Found: C, 54.85; H, 5.76; N, 8.00; S, 6.31.

EXAMPLE 44

N-(1-(((3'-(cyanomethyl-4'-methoxyl(1,1'-biphenyl)-4-yl)oxy)methyl)-2-(3,4,4-trimethy-2,5-dioxo-1-imidazolidinyl)ethyl)-N-hydroxyformamide The desired product was prepared according to the procedures of Example 16C and 16E, substituting 4-(3'-cyanomethyl-4'-methoxyphenyl)phenol for 4-bromophenol in Example 16C.

$^1$H NMR (300 MHz, DMSO-d6) δ; 1.275, 1.290 (6H), 2.788, 2.800 (3H), 3.566–3.641 (m, 1H), 3.708–3.821 (m, 1H), 4.047–4.214 (m, 2H), 4.3994.416 (m, 0.5H), 4.846 (m, 0.5H), 6.973–7.013 (2H), 7.110–7.140 (1H), 7.543–7.608 (m, 4H), 7.291 (s, 0.5H), 8.319 (s, 0.5H), 9.576 (s, 0.5H), 9.904 (s, 0.5H);

MS (ESI) m/e 481 (M+H)$^+$, 498 (M+NH$_4$)$^+$, 479 (M–H)$^-$,

Anal. calcd for $C_{25}H_{28}N_4O_6$.0.5MeOH: C, 61.68; H, 6.08; N, 11.28. Found: C, 62.07; H, 6.21; N, 10.91.

EXAMPLE 45

N-(1-(((3'-(cyanomethyl)(1,1'-biphenyl)-4-yl)oxy)methyl)-3-(4,4-dimethyl-2,5-dioxo-1-imidazolidinyl)propyl)-N-hydroxyformamide The desired product was prepared according to the procedures of Example 5, omitting the methylation step in Example 5B and substituting 4-(3'-cyanomethylphenyl)phenol for 4'-hydroxy-4-biphenylcarbonitrile in Example 5F.

$^1$H NMR (300 MHz, DMSO-d6) δ 1.27 (s, 6H), 1.70–2.00 (m, 2H), 3.37–3.47 (m, 2H), 3.96–4.08 (s+m, 5H), 7.00–7.03 (d, 2H, 8.4 Hz), 7.28–7.31 (d, 1H, 8.7 Hz), 7.426–7.477 (t, 1H, 7.5 Hz), 7.56–7.61 (m, 4H), 7.915 (s, 0.73H), 8.28–8.34 (1.27H), 9.55 (s, 0.75H), 9.96 (s, 0.25H);

MS (ESI) m/e 451 (M+H)$^+$, 468 (M+NH$_4$)$^+$, 449 (M–H)$^-$;

Anal. calcd for $C_{25}H_{28}N_4O_6$MeOH: C, 62.22; H, 6.26; N, 11.61. Found: C, 62.25; H, 5.95; N, 11.57.

EXAMPLE 46

N-(1-(((4'-butoxy(1,1'-biphenyl)-4-yl)sulfonyl)methyl)-2-(4,4-dimethy-2,5-dioxo-1-imidazolidinyl)ethyl)-N-hydroxyformamide

EXAMPLE 46A 1-(4-bromophenylthio)-3-(4,4-dimethyl-2,5-dioxoimidazolidin-1-yl)-2-propanone A solution of 4-bromothiophenol (2.15 g, 11.4 mmol) in DMF (50 mL) at room temperature was treated with cesium carbonate (5.57 g, 17.1 mmol) for 20 minutes, treated in a single portion with Example 23A (2.5 g, 9.5 mmol), stirred for 1 hour, diluted with water, and extracted with ethyl acetate. The combined extracts were washed with water and brine, dried (Na$_2$SO$_4$), filtered, concentrated, and purified on silica gel with 20 to 35 to 50% ethyl acetate/hexane to provide 3.17 g (90%) of the desired product as a white solid.

MS (APCI) m/e 371, 373 (M+H)$^+$, 388, 390 (M+NH$_4$)$^+$, 369, 371 (M–H), 405, 407 (M+Cl)$^-$.

EXAMPLE 46B 1-((4'-butoxy(1,1'-biphenyl)-4-yl)thio)-3-(4,4-dimethyl-2,5-dioxoimidazolidin-1-yl)-2-propanone A solution of Example 46A (700 mg, 1.89 mmol) in DME (20 mL) at room temperature was treated with 4-n- butoxybenzeneboronic acid (549 mg, 2.83 mmol), tetrakis-(triphenylphosphine)-palladium (218 mg, 0.189 mmol) and 1M sodium carbonate (3.54 mL, 3.54 mmol), the reaction vessel was sealed and heated at 90° C. for 6 hours, diluted with ethyl acetate, washed with sequentially saturated ammonium chloride solution, water and brine, dried ($Na_2SO_4$), filtered, concentrated and purified on silica gel with 30 to 50% ethyl acetate/dichloromethane to provide 650 mg (78%) of the desired product as a yellow solid.

MS (APCI) m/e 441 (M+H)+, 458 (M+$NH_4$)+, 439 (M−H), 475 (M+Cl)−.

EXAMPLE 46C

N-(1-(((4'-butoxy(1,1'-biphenyl)-4-yl)thio)methyl)-2-(4,4-dimethy-2,5-dioxo-1-imidazolidinyl)ethyl)-N-hydroxyformamide The desired product was prepared by substituting Example 46B into the procedures described in Example 2D, 2E, 2F.

$^1$H NMR (300 MHz, DMSO-d6) δ; 0.919–0.967 (t, 3H, J=7.2 Hz), 1.225–1.237(s+s, 6H), 1.389–1.512(m, 2H), 1.666–1.760(m, 2H), 3.110–3.192(m, 2H), 3.528–3.735 (m, 2H), 3.987–4.030(t, 2H, J=6.3 Hz), 4.030(m, 0.5H), 4.750 (m, 0.5H),6.991–7.020 (d, 2H, J=9 Hz), 7.383–7.417 (dd, 2H, J=1.8, 8.4 Hz), 7.561–7.601 (4H), (1.5H), 9.56 (s, 7.767(s, 0.5H), 8.299(s, 1H), 8.337(s, 0.5H), 9.457(br s, 0.5H), 9.695(br s, 0.5H);

MS (ESI) m/e 484 (M−H)−;

High resolution MS(FAB) Calc. m/z for m·+485.1984, observed m/z 485.1980.

EXAMPLE 46D

N-(1-(((4'-butoxy(1,1'-biphenyl)-4-yl)sulfonyl)methyl)-2-(4,4-dimethy-2,5-dioxo-1-imidazolidinyl) ethyl)-N-hydroxyformamide A solution of Example 46C (127 mg, 0.262 mmol) in methanol (2 mL) and pH 7 buffer (1 mL) at 0° C. was treated with oxone(402 mg, 0.655 mmol) for 30 minutes, warmed to ambient temperature for 1 hour, neutralized with saturated sodium bicarbonate, and extracted with dichloromethane. The combined extracts were washed with brine, dried ($Na_2SO_4$), filtered, and concentrated. The crude mixture was purified on silica gel with 50% ethyl acetate/hexane then 10% methanol/dichloromethane to provide 82 mg (60%) of the desired product as an white solid.

$^1$H NMR (300 MHz, DMSO-d6) δ; 0.92–0.97 (t, 3H, 7.5 Hz), 1.20, 1.22 (s+s, 6H), 1.42–1.52 (m, 2H), 1.68–1.77 (m, 2H), 3.41–3.72 (m, 3.5H), 4.02–4.06 (t, 2H, 6.6 Hz), 4.52 (m, 0.5H), 4.89 (m, 0.5H), 7.05–7.08 (d, 2H, 8.4 Hz), 7.70–7.74 (2H),7.91 (s, 3.5H), 8.10 (s, 0.5H), 8.32–8.35 (d, 1H, 9.6 Hz), 9.48 (s, 0.5H), 9.62 (s, 0.5H);

MS (ESI) m/e 518 (M+H)+, 535 (M+$NH_4$)+, 516 (M−H)−, 552 (M+Cl)−;

Anal. calcd for $C_{25}H_{28}N_4O_6 \cdot 0.25H_2O$: C, 57.51; H, 6.08; N, 8.04. Found: C, 57.78; H, 6.18; N, 7.84.

EXAMPLE 47

N-(1-(((4'-cyano(1,1'-biphenyl)-4-yl)oxy)methyl)-3-(4,4-dimethyl-2,5-dioxo-1-imidazolidinyl)propyl)-N-hydroxyformamide

EXAMPLE 47A 1-bromo-4-(3,4,4-trimethyl-2,5-dioxoimidazolidin-1-yl)butan-2-one To a suspension of $CuBr_2$ (1.91 g, 8.5 mmol) and lithium bromide (1.48 g, 17 mmol) in THF (10 mL) was added a solution of 1.06 g (5.3 mmol)of 1-((1',2'-oxiranyl)propyl-4,4-dimethyl-2,5-dioxoimidazolidine(prepared from Example 5A following the procedure of Example 5C) in 15 mL of THF. The reaction mixture was stirred for 2 hours at room temperature, then partitioned between ethyl acetate and pH 7 buffer. The organic extract was washed with brine, dried and concentrated. The residue was filtered through a plug of silica eluting with ethyl acetate, and the filtrate was concentrated toi give a white solid, which was dissolved in acetone (25 mL), cooled to 0° C., then treated with 2.5 mL of 8M Jones reagent and stirred at room temperature for 3 hours. The reaction was quenched with 2 mL isopropanol, then partitioned between ethyl acetate and water. The organic extract was washed with brine, dried, filtered, and concentrated. The residue was filtered through a plug of silica gel eluting with ethyl acetate, and the filtrate was concentrated to give the desired product.

EXAMPLE 47B

N-(1-(((4'-cyano(1,1'-biphenyl)-4-yl)oxy)methyl)-3-(4,4-dimethyl-2,5-dioxo-1-imidazolidinyl)propyl)-N-hydroxyformamide The desired product was prepared according to the procedures of Example 16C and 16E, substituting 47A for Example 16B and 4'-hydroxy-4-biphenylcarbonitrile for 4-bromophenol in Example 16C.

mp 202–204° C.;

$^1$H NMR (300 MHz, DMSO-d6) δ; 1.272 (6H), 1.70–2.00 (m, 2H), 3.38–3.46 (t, 2H, J=6 Hz), 3.92–4.18 (m, 2.5H), 4.46–4.57 (m, 0.5H), 7.03–7.06 (d, 2H, J=8.7 Hz), 7.695–7.724 (d, 2H, J=8.7 Hz), 7.82–7.92 (m, 6.5H), 8.26–8.35 (1.5H), 9.75(s), 9.96 (s,1H);

MS (ESI) m/e 437 (M+H)+, 454 (M+$NH_4$)+, 459 (M−H)−;

Anal. calcd for $C_{25}H_{28}N_4O_6 \cdot 0.25H_2O$: C, 62.64; H, 5.60; N, 12.70. Found: C, 62.55; H, 5.47; N, 12.65.

EXAMPLE 48

N-(1-(((4'-(methylsulfonyl)(1,1'-biphenyl)-4-y)oxy)methyl)-2-(4,4-dimethyl-2,5-dioxo-1-imidazolidinyl)ethyl)-N-hydroxyformamide

EXAMPLE 48A 1-(4'-(thiomethyl)(1,1'-biphenyl)-4-yl)oxy)-3-(4,4-dimethyl-2,5-dioxoimidazolidin-1-yl)-2-propanone A solution of 4'-hydroxy-4biphenylmethylsulfide (1.18 g, 5.47 mmol) in DMF (25 mL) at ambient temperature was treated with cesium carbonate (2.23 g, 6.84 mmol) for 20 minutes, treated in a single portion with Example 23A (1.2 g, 4.56 mmol), stirred for 2 hours at ambient temperature and diluted with water, and extracted with ethyl acetate. The combined extracts were washed with water and brine, dried ($Na_2SO_4$), filtered, concentrated and purified on silica gel with 50 to 80% ethyl acetate/hexane to provide 1.0 g (55%) of the desired product as a white solid.

MS (APCI) m/e 399 (M+H)+, 416 (M+$NH_4$)+, 397 (M−H)−, 433 (M+Cl)−.

EXAMPLE 48B

N-(1-(((4'-(thiomethyl)(1,1'-biphenyl)-4-yl)oxy)methyl)-2-(4,4-dimethyl-2,5-dioxo-1-imidazolidinyl)ethyl)-N-hydroxyformamide The desired product was prepared by substituting Example 48A in the procedures described in Example 2D, 2E, 2F.

MS (ESI) m/e 444 (M+H)$^+$, 461 (M+NH$_4$)$^+$, 466 (M+Na)$^+$, 442 (M−H)$^-$.

EXAMPLE 48C

N-(1-(((4'-(methylsulfonyl)(1,1'-biphenyl)-4yl)oxy)methyl)-2-(4,4-dimethyl-2,5-dioxo-1-imidazolidinyl)ethyl)-N-hydroxyformamide A solution of Example 48B (440 mg, 0.993 mmol) in methanol (100 mL) and water (50 mL) at 0° C. was treated with oxone (1.27 g, 2.06 mmol) and sodium bicarbonate (174 mg, 2.06 mmol) for 1 hour, warmed to ambient temperature for 1.5 hour, diluted with water, and extracted with dichloromethane. The combined extracts were washed with brine, dried (Na$_2$SO$_4$), filtered and concentrated. The crude mixture was purified on silica gel with 80% ethyl acetate/hexane then 10% methanol/dichloromethane then recrystallized from dichloromethane/hexane to provide 375 mg (79%) of the desired product as an off-white solid.

$^1$H NMR (300 MHz, DMSO-d6) δ; 1.26–1.27 (s+s, 6H), 3.24 (s, 3H), 3.53–3.80 (m, 2H), 4.08–4.24 (m, 2H), 4.37–4.48 (m, 0.5H), 4.80–4.92 (m, 0.5H), 7.04–7.08 (dd, 2H, J=3, 8.4 Hz), 7.72–7.75 (d, 2H, J=8.7 Hz), 7.89–8.00 (4.5H), 8.33–8.40 (1.5H), 9.56 (s, 0.5H), 9.88 (s, 0.5H);

MS (ESI) m/e 476 (M+H)$^+$, 493(M+NH$_4$)$^+$, 474 (M−H)$^-$, 510 (M+Cl)$^-$.

EXAMPLE 49

N-(1-(((3'-cyano(1,1'-biphenyl)-4-yl)oxy)methyl-2-(2,5-dioxo-1-pyrrolidinyl)ethyl)-N-hydroxyformamide

EXAMPLE 49A 1-(4'-cyano-(1,1'-biphenyl)-4-yl)oxy)-3-(2,5-dioxopyrrolidin-1-yl)-2-propanone The desired product was prepared as in Example 3C, substituting potassium succinimide (0.10 g, 0.95 mmol) for potassium phthalimide. Purification by trituration with ethyl acetate provided 0.19 g (68%) of the desired product as a white solid.

MS (APCI) m/e 383 (M+Cl)$^+$.

EXAMPLE 49B (1-(4'-cyano-(1,1'-biphenyl)-4-yl)oxy)-3-(2,5-dioxopyrrolidin-1-yl)-prop-2-yl)hydroxylamine The desired product was prepared from Example 49A using the procedure described in Example 2D and 2E.

EXAMPLE 49C

N-(1-(((3'-cyano(1,1'-biphenyl)-4-yl)oxy)methyl)-2-(2,5-dioxo-1-pyrrolidinyl)ethyl)-N-hydroxyformamide The desired product was prepared from 49B using the procedure described in Example 2F.

mp 128° C.;

$^1$H NMR (300 MHz, d6-DMSO) δ 10.01 (s, 0.5H), 9.63 (s, 0.5H), 8.34 (s, 0.5H), 7.98 (s, 0.5H), 7.90–7.82 (m, 4H), 7.73 (d, 2H, J=8.8 Hz), 7.06–6.89 (m, 2H), 4.90–4.78 (m, 0.5H), 4.37–4.24 (m, 0.5H), 4.22–4.04 (m, 2H), 3.74–3.60 (m, 2H), 2.65–2.61 (m, 4H);

MS (ESI) m/e 394 (M+H)$^+$, 411 (M+NH$_4$)$^+$, 392 (M−1)$^+$;

Anal. Calcd for: C$_{21}$H$_{19}$N$_3$O$_5$H$_2$O: C, 61.30; H, 5.14; N, 10.21. Found: C, 61.20; H, 5.03; N, 10.03.

EXAMPLE 50

N-(1-(((4'-cyano(1,1'-biphenyl)-4-yl)oxy)methyl)-2-(4,4-dimethyl-2,6-dioxo-1-piperidinyl)ethyl)N-hydroxyformamide The desired product was prepared as in Example 49, substituting potassium-3,3-dimethylglutarimide (0.16 g, 1.1 mmol) for potassium succinimide. mp 121° C.;

$^1$NMR (d6-DMSO) δ 9.88–9.78 (s, 0.5H), 9.60–9.52 (s, 0.5H), 8.31 (s, 0.5H), 7.95 (s, 0.5H), 7.90–7.82 (m, 4H), 7.73 (d, 2H, J=8.9 Hz), 7.02 (d, 2H, J=8.8 Hz), 4.88–4.77 (s, 1H), 4.30–3.78 (m, 4H), 2.56 (s, 4H), 0.98 (s, 6H);

MS (ESI) 436 (M+H)$^+$, 458 (M+Na)$^+$, 434 (M−H)$^+$.

EXAMPLES 51 AND 52

N-(1S-(((4'-cyano(1,1'-biphenyl)-4-yl)oxy)methyl)-2-(2,5-dioxo-1-pyrrolidinyl)ethyl)-N-hydroxyformamide N-(1R-(((4'-cyano(1,1'-biphenyl)-4-yl)oxy)methyl)-2-(2,5-dioxo-1-pyrrolidinyl)ethyl)-N-hydroxyformamide

EXAMPLE 51 A AND 52A

A solution of Example 49B (0.2 g, 0.55 mmol), D-Mannose diacetonide (0.13 g, 0.50 mmol), and acetic acid (0.03 mL, 0.50 mmol) in chlorororm (5 mL) were heated at reflux for 16 h, cooled, and partitioned between dichloromethane and saturated sodium bicarbonate. The organic layer was washed sequentially with water and brine, dried (MgSO$_4$), filtered, and concentrated. Purification by HPLC provided the two enantiomers 51A (31%) and 52A (16%).

EXAMPLE 51B

A solution of 51A in MeOH (1 mL) and HCl (conc) (0.5 mL) was stirred at ambient temperature for 15 min, treated with saturated sodium bicarbonate, and partitioned between ethyl acetate and water. The organic layer was dried (MgSO$_4$), filtered, and concentrated to provide 0.014 g (79%) of the corresponding hydroxyl amine, which was then formylated as in Example 2F.

EXAMPLE 52B

The desired product was prepared according to Example 51B substituting Example 52A for Example 51A.

EXAMPLE 53

N-(1-(((4'-cyano(1,1'-biphenyl)-4-yl)oxy)methyl)-2-(3-ethyl-3-methyl-2,5-dioxo-1-pyrrolidinyl)ethyl)-N-hydroxyformamide The desired product was prepared as in Example 49, substituting potassium-3-methyl-3-ethyl succinimide (0.22 g, 1.53 mmol) for potassium succinimide.

$^{11}$H NMR (d6-DMSO) δ 9.99–9.94 (br, 0.5H), 9.64–9.58 (br, 0.5H), 8.31 (d, 0.5H, J=1.8 Hz), 7.93 (d, 0.5H, J=2.9 Hz), 7.87 (q, 4H, J=4.1 Hz), 7.74 (d, 2H, J=8.9 Hz), 7.04 (dd, 2H, J=8.8, 2.6 Hz), 4.93–4.81 (m, 0.5H), 4.44–4.33 (m, 0.5H), 4.24–4.05 (m, 2H), 3.85–3.71 (m, 1H), 3.62–3.53 (m, 1H), 2.69–2.38 (m, 2H), 1.64–1.46 (m, 2H), 1.18 (d, 3H, J=4.4 Hz), 0.85–0.75 (m, 3H);

MS (ESI) 436 (M+H)⁺, 434 (M−H)⁺, 458 (M+Na)⁺, 453 (M+NH₄)⁺;

Anal. Calcd for: $C_{24}H_{25}N_3O_5$: C, 66.19; H, 5.78; N, 9.64. Found: C, 66.07; H, 5.85; N, 9.37.

EXAMPLE 54

N-(4-(4-(((4-chlorophenoxy)phenyl)sulfonyl)methyl) tetrahydro-2H-pyran-4-yl)-N-hydroxyformamide

EXAMPLE 54A

The desired product was prepared as in Example 2D substituting 5,6-dihydro-2H-pyran-2-one (4.3 g, 43 mmol) for 1-(4-(4'-carbonitrilephenyl)phenoxy)-3-thiophenoxypropan-2-one and O-benzyl hydroxylamine for hydroxylamine to provide the corresponding oxime. Purification on silica gel with 1% methanol/dichloromethane provided 8.5 g (96%) of the desired product as a clear liquid.

MS (ESI) 207 (M+H)⁺

EXAMPLE 54B

N-(4-(4-(((4-chlorophenoxy)phenyl)sulfonyl)methyl) tetrahydro-2H pyran-4-yl)-N-benzyloxy Amine To a solution of phenoxyphenyl-4-chloro-4'-methylsulfone (0.76 g, 2.7 mmol)(preparation desribed in J.Med. Chem. 29, 427–433, 1986) at −78° C. was added n-butyllithium (1.1 mL, 2.7 mmol). After stirring at −78° C. for 15 minures, $BF_3.OEt_2$ was added, followed by Example 54A. After 1 h, the reaction mixture was partitioned between with water and ethyl acetate, dried (MgSO₄), filtered, and concentrated. Recrystallization with ethyl acetate provided 0.41 g (35%)of the desired compound as a white solid. MS (ESI) 488 (M+H)+, 510 (M+Na)⁺.

EXAMPLE 54C

N-(4-(4-(((4-chlorophenoxy)phenyl)sulfonyl)methyl) tetrahydro-2H-pyran-4-yl)-N-benzyloxyformamide A solution of Example 54B (0.05 g, 0.10 mmol) in dichloromethane (2 mL) was treated with formic-p-methoxyphenyl anhydride, stirred at ambient temperature for 16 h, treated with H₂O, and partitioned between ethyl acetate and brine. The organic layer was dried (MgSO₄), filtered, and concentrated. Purification on silica gel with 10% ethyl acetate/dichloromethane provided 0.017 g (32%) of the desired compound as a white solid MS (ESI) 516 (M+H)⁺, 533 (M+NH₄)⁺, 538 (M+Na)⁺.

EXAMPLE 54D

N-(4-(4-(((4-chlorophenoxy)phenyl)sulfonyl)methyl) tetrahydro-2H-pyran-4yl)-N-hydroxyformamide A solution of Example 54C (0.017 g, 0.033 mmol) and Pd black (0.006 g) in dioxane (2 ml) and acetic acid (2 mL) was stirred under H₂ for 20 min, treated with NaHCO₃, partitioned between ethyl acetate and water. The organic layer was dried (MgSO₄), filtered, and concentrated. Purification on silica gel with 2% methanol/dichloromethane provided 0.002 g (14%) of the desired compound.

¹H NMR (d6-DMSO) δ 9.50–9.45 (br, 1H), 8.19 (s, 1H), 7.90–7.86 (m, 2H), 7.53–7.50 (m, 2H), 7.22–7.18 (m, 4H), 3.70–3.58 (m, 4H), 3.55–3.44 (m, 2H), 2.22–2.07 (m, 2H), 2.07–1.91 (m, 2H);

MS (ESI) 424 (M−H)⁺, 426 (M+H)⁺, 448 (M+Na)⁺.

EXAMPLE 55

N-(1-(((4'-cyano(1,1'-biphenyl)-4-yl)oxy)methyl)-2-(((2-methoxycarbonyl)phenyl)-thio)ethyl)-N-hydroxyformamide The desired product was prepared following the procedure from Example 2B,C, D, E, F substituting methyl thiosalicylate (600 mg, 2.39 mmol) for thiophenol in Example 2B. Mixture of two rotamers: ¹H NMR (300 MHz, d₆-DMSO) δ 10.11 (s, 1H), 9.73 (s, 1H), 8.41 (s, 1H), 7.95 (s, 1H), 7.90–7.83 (m, 10 H), 7.75–7.71 (m, 4H), 7.59–7.55 (m, 4H), 7.31–7.26 (m, 2H), 7.09–7.05 (m, 4H), 4.75 (m, 1H), 4.2804.24 (m, 4H0, 4.18 (m, 1H), 3.83 (s, 3H), 3.82 (s, 3H), 3.31–3.18 (m, 4H);

MS (ESI) m/e 463 (M+1)⁺;

Anal. calcd for $C_{25}H_{22}N_2O_5S$: C, 64.92; H, 4.79; N, 6.06. Found: C, 64.69; H, 4.63; N, 5.92.

EXAMPLE 56

N-(1-(((4'-cyano(1,1'-biphenyl)-4-yl)oxy)methyl)-5-((4-1ethyl-2-oxo-2H-1-benzopyran-6-yl)oxy)pentyl)-N-hydroxyformamide

EXAMPLE 56A 6-(4-methyl-2-oxo-2H-1-benzopyran-6-yl)oxy)-hex-1-ene

The desired product was prepared following the procedure from Example 5A substituting 6-hydroxy-4-methylcoumarin (500 mg, 2.84 mmol) for 5,5-dimethylhydantoin and 5-hexen-1-ol for 3-buten-1-ol. Purification on silica gel with 20% ethyl acetate/hexanes provided 560 mg (76%) of the desired product.

¹H NMR (300 MHz, d₆-DMSO) δ 7.34 (dd, 1H), 7.24–7.20 (m, 2H), 6.40 (d, 1H), 5.90–5.77 (m, 1H), 5.04 (dq, 1H), 4.98 (dq, 1H), 4.06 (t, 2H), 2.43 (d, 3H), 2.10 (q, 2H), 1.75 (dt, 2H), 1.53 (dt, 2H).

EXAMPLE 56B

N-(1-(((4'-cyano(1,1'-biphenyl)-4-yl)oxy)methyl)-5-((4-methyl-2-oxo-2H-1-benzopyran-6-yl)oxy) pentyl)-N-hydroxyformamide The desired product was prepared following the procedures from Example 5C, 1B, 2C, 2D,2E and 2F substituting 56A (500 mg, 1.94 mmol) for 5B in Example 56B. Purification on silica gel with 50% ethyl acetate/hexanes provided 400 mg (75%) of the desired product.

Mixture of two rotamers: ¹H NMR (300 MHZ, d₆-DMSO) δ 9.89 (s, 1H), 9.51 (s, 1H), 8.42 (s, 1H), 8.03 (s, 1H),7.86 (m, 8H), 7.73–7.70 (m, 41), 7.34 (d, 2H), 7.24–7.21 (m, 4H), 7.08–7.04 (m, 4H), 6.40 (s, 2H), 4.60 (s, 1H), 4.18–3.99 (m, 9H), 2.43 (s, 6H), 1.86–1.54 (m, 12H);

MS (ESI) m/e 513 (M+1)⁺;

Anal. calcd for $C_{30}H_{28}N_2O_6$: C, 70.30; H, 5.51; N, 5.47. Found: C, 70.52; H, 5.85; N, 5.20.

EXAMPLE 57

N-(1-(((4'-cyano(1,1'-biphenyl)-4-yl)oxy)methyl)-4-((4-methyl-2-oxo-2H-1-benzopyran-6-yl)oxy)butyl)-N-hydroxyformamide The desired product was prepared following the procedure from Example 56 substituting 4-penten-1-ol for 5-hexen-1-ol in Example 56A.

Mixture of two rotamers: $^1$H NMR (300 MHZ, d$_6$-DMSO) δ 9.94 (s, 1H), 9.55 (s, 1H0, 8.44 (s, 1H), 8.06 (s, 1H), 7.86 (m, 8H), 7.73–7.70 (m, 4H), 7.35 (d, 2H), 7.26–7.22 (m, 4H), 7.08–7/05 (m, 4H), 6.40 (s, 2H), 4.65 (m, 1H), 4.17–4.04 (m, 9H), 2.44 (s, 6H), 1.77 (m, 8H);

MS (ESI) m/e 499 (M+1)$^+$;

Anal. calcd for $C_{29}H_{26}N_2O_6 \cdot 0.75H_2O$: C, 68.03; H, 5.41; N, 5.47. Found: C, 68.21; H, 5.25; N, 5.28.

EXAMPLE 58

N-(1-(((4'-cyano(1,1'-biphenyl)-4-yl)oxy)methyl)-4-((4-methyl-2-oxo-2H-1-benzopyran-7-yl)oxy)butyl)-N-hydroxyformamide The desired product was prepared following the procedure from Example 56 substituting 7-hydroxy-4-methylcoumarin (500 mg, 2.8 mmol) for 6-hydroxy-4-methylcoumarin and 4-penten-1-ol for 5-hexen-1-ol in Example 56A.

Mixture of two rotamers: $^1$H NMR (300 MHZ, d$_6$-DMSO) δ 9.95 (s, 1H), 9.55 (s, 1H), 9.44 (s, 1H), 8.05 (s, 1H), 7.907.82 (m, 8H), 7.73–7.67 (m, 6H), 7.08–7.04 (m, 4H), 7.01–6.95 (m, 4H), 6.21 (s, 2H), 4.64 (m, 1H), 4.20–4.01 (m, 9H), 2.40 (s, 6H), 1.80–1.74 (m, 8H);

MS (ESI) m/e 499 (M+1)$^+$;

Anal. calcd for $C_{29}H_{26}N_2O_6$: C, 69.87; H, 5.26; N, 5.62. Found: C, 69.51; H, 5.33; N, 5.40.

EXAMPLE 59

N-(1-(((4'-cyano(1,1'-biphenyl)-4-yl)oxy)methyl)-5-((4-methyl-2-oxo-2H-1-benzopyran-7-yl)oxy)pentyl)-N-hydroxyformamide The desired product was prepared following the procedure from Example 56 substituting 7-hydroxy-4-methylcoumarin (500 mg, 2.8 mmol) for 6-hydroxy-4-methylcoumarin in Example 56A.

Mixture of two rotamers: $^1$H NMR (300 MHZ, d$_6$-DMSO) δ 9.89 (s, 1H0, 9.50 (s, 1H0, 8.42 (s, 1H), 8.03 (s, 1H), 7.90–7.82 (m, 8H), 7.73–7.66 (m, 6H), 7.08–7.03 (m, 4H), 6.98–6.94 (m, 2H0, 6.21 (s, 2H), 4.60 (m, 1H), 4.15–3.98 (m, 9H), 2.40 (s, 6H), 1.84–1.40 (m, 12H);

MS (ESI) m/e 513 (M+1)$^+$;

Anal. calcd for $C_{30}H_{28}N_2O_6$: C, 70.30; H, 5.51; N, 5.47. Found: C, 70.35; H, 5.52; N, 5.17.

EXAMPLE 60

N-(1-(((4'-cyano(1,1'-biphenyl)-4-yl)oxy)methyl)-2-(5,5-dimethy-2,4-dioxo-3-oxazolidinyl)ethyl)N-hydroxyformamide The desired product was prepared as in Example 49, substituting 5,5-dimethyloxazolidinine-2,4-dione (300 mg, 0.8 mmol) for succinimide.

Mixture of two rotamers: $^1$H NMR (300 MHZ, d$_6$-DMSO) δ 10.08 (s, 1H), 9.70 (s, 1H), 8.35 (s, 1H), 7.98 (s, 1H), 7.90–7.83 (m, 8H), 7.74 (d, 4H), 7.06 (d, 4H), 4.90 (m, 1H), 4.47 (m, 1H), 4.24–4.16 (m, 4H), 3.85 (d, 1H), 3.80 (d, 1H), 3.69–3.65 (m, 1H), 3.64–3.61 (m, 1H), 1.49 (s, 6H), 1.48 (s, 6H);

MS (ESI) m/e 441 (M+18)$^+$.

EXAMPLE 61

N-(1-(((4'-cyano(1,1'-biphenyl)-4-yl)sulfonyl)methyl)-2-(3,4,4-methy-2,5-dioxo-1-imidazolidinyl)ethyl-N-hydroxyformamide

EXAMPLE 61A 1-((4'-cyano(1,1'-biphenyl)-4yl)thio)-3-(3,4,4-trimethyl-2,5-dioxoimidazolidin-1-yl)-2-propanone A solution of 4'-thiol-4biphenylcarbonitrile (150 mg, 0.71 mmol) in 6 mL of DMF at −5° C. was treated with potassium carbonate (89 mg, 0.645 mmol) and 1-bromo-3-(3,4,4-trimethyl-2,5-dioxo-1-imidazolidin-1-yl)-2-propanone (179 mg, 0.645 mmol), stirred 1 h at −5° C., quenched with saturated ammonium chloride, extracted with ethyl acetate, washed with brine, dried over $Na_2SO_4$, filtered, and concentrated to a solid. Purification on silica gel with 1:1 ethyl acetate/hexanes provided 200 mg (75%) of the desired product.

$^1$H NMR (300 MHZ, d$_6$-DMSO) δ 7.94–7.87 (m, 4H), 7.72 (d, 2H), 7.43 (d, 2H), 4.55 (s, 2H), 4.27 (s, 2H), 2.80 (s, 3H), 1.32 (s, 6H).

EXAMPLE 61B

N-(1-(((4'-cyano(1,1'-biphenyl)-yl)thio)methyl)-2-(3,4,4-trimethy-2,5-dioxo-1-imidazolidinyl)ethyl-N-hydroxyformamide The desired product was prepared from Example 61A following the procedures from Example 2D, 2E and 2F.

Mixture of two rotamers: $^1$H NMR (300 MHZ, d$_6$-DMSO) δ 9.76 (s, 1H), 9.51 (s, 1H), 8.29 (s, 1H), 7.93–7.87 (m, 8H), 7.75–7.72 (m, 5H), 7.50–7.44 (m, 4H), 4.60 (m, 1H), 4.10 (m, 1H), 3.80–3.60 (m, 4H), 3.25–3.15 (m, 4H), 2.77 (s, 6H), 1.25 (s, 12H).

EXAMPLE 61C

N-(1-(((4'-cyano(1,1'-biphenyl)-4-yl)sulfonyl)methyl)-2-(3,4,4-trimethy-2,5-dioxo-1-imidazolidinyl)ethyl)-N-hydroxyformamide A solution of Example 61B (81 mg, 0.18 mmol) in 4:1 THF/H$_2$O at 0° C. was treated with oxone (140 mg) and NaHCO$_3$ (33 mg), stirred at 0° C. for 30 minutes then 23° C. for 1 hour, quenched with H$_2$O, extracted with ethyl acetate, washed with brine, dried over $Na_2SO_4$, filtered, and concentrated to a white solid. Purification on silica gel with 2% methanol/dichloromethane provided 43 mg (49%) of the desired product.

Mixture of two rotamers: $^1$H NMR (300 MHZ, d$_6$-DMSO) δ 9.71 (s, 1H), 9.54 (s, 11H), 8.09 (s, 1H), 8.07–7.96 (m, 16H), 7.74 (s, 1H), 4.90 (m, 1H), 4.54 (m, 1H), 3.74–3.60 (m, 4H), 3.55–3.44 (m, 4H), 2.74 (s, 3H), 2.74 (s, 3H), 1.24–1.22 (m, 12H);

MS (ESI) m/e 485 (M+1)$^+$;

Anal. calcd for $C_{23}H_{24}N_4O_6S$: C, 57.01; H, 4.99; N, 11.56. Found: C, 56.86; H, 5.21; N, 11.28.

EXAMPLE 62

N-(1-(((4'-cyano(1,1'-biphenyl)-4-yl)oxy)methyl)-2-(3-methyl-2,5-dioxo-1-imidazolidinyl)ethyl)-N-hydroxyformamide The desired product was prepared as in Example 49, substituting 1-methylhydantoin for succinimide.

Mixture of two rotamers: $^1$H NMR (300 MHZ, d$_6$-DMSO) δ 9.97 (s, 1H), 9.61 (s, 1H), 8.35 (s, 1H), 7.98 (s, 1H), 7.90–7.83 (m, 8H), 7.73 (d, 4H), 7.03 (d, 2H), 7.01 (d, 2H), 4.88–4.84 (m, 1H), 4.39–4.35 (m, 1H), 4.22–4.08 (m, 4H), 3.97 (s, 2H), 3.94 (s, 2H), 3.75–3.57 (m, 4H), 2.86 (s, 3H), 2.85 (s, 3H);

MS (ESI) m/e 409 (M+1)$^+$;

Anal. calcd for $C_{21}H_{20}N_4O_5$: C, 61.76; H, 4.94; N, 13.72. Found: C, 61.47; H, 5.00; N, 3.39.

EXAMPLE 63

N-(1-(((4'-cyano(1,1'-biphenyl)-4-yl)sulfonyl)methyl)-2-(4,4-dimethy-2,5-dioxo-1-imidazolidinyl)ethyl)-N-hydroxyformamide The desired product was prepared following the procedure from Example 61 substituting 1-bromo-3-(4,4- dimethyl-2,5-dioxo-1-imidazolidin-1-yl)-2-propanone for 1-bromo-3-(3,4,4-trimethyl-2,5-dioxo-1-imidazolidin-1-yl)-2-propanone in Example 61 A. Mixture of two rotamers: $^1$H NMR (300 MHZ, d$_6$-DMSO) δ 9.66 (s, 1H0, 9.51 (s, 1H), 8.38 (s, 1H), 8.34 (s, 1H), 8.10 (s, 1H), 8.07–7.96 (s, 16H), 7.74 (s, 1H), 4.944.86 (m, 11), 4.58–4.50 (m, 1H), 3.80–3.37 (m, 8H), 1.23–1.20 (m, 12H);

MS (ESI) m/e 488 (M+18)$^+$;

Anal. calcd for $C_{22}H_{22}N_4O_6S$: C, 56.16; H, 4.71; N, 11.91. Found: C, 56.12; H, 5.00; N, 11.59.

EXAMPLE 64

( )-N-(1-(((4'-chloro-(1,1'-biphenyl)-4-yl)oxy)methyl)-2-(3,4,4-trimethyl-2,5-dioxo-1-imidazolidinyl)ethyl)-N-hydroxyformamide

EXAMPLE 64A 1-(4" -chloro-1',1"-biphenyl)-4'-yl)oxy)-3-(3,4,4-trimethyl-2,5-dioxoimidazolidin-1-yl)-propan-2-one A solution of Example 16B (0.81 g, 2.93 mmol), 4-chloro-4'-hydroxybiphenyl (0.50 g, 2.44 mmol), and potassium carbonate (0.35 g, 2.57 mmol) in dry DMF (50 mL) was stirred at ambient temperature for 1.5 hour and partitioned between ethyl acetate and water. The aqueous layer was removed and extracted with ethyl acetate (1×). The combined organic extracts were diluted with an equal volume of hexanes and washed sequentially with water (3×) and brine (2×), dried (Na$_2$SO$_4$), filtered, and concentrated to provide 0.89 g of a waxy clumpy solid which was purified on silica gel with 40% ethyl acetate/dichloromethane to provide 0.46 g (47%) of the desired product as a colorless solid.

mp 165–166° C.;

MS (DCI/NH$_3$) m/e 379 (M+NH$_4$)$^+$.

EXAMPLE 64B ( )-N-(1-(((4'-chloro-(1,1'-biphenyl)-4-yl)oxy)methyl)-2-(3,4,4-trimethyl-2,5-dioxo-1-imidazolidinyl)ethyl)-N-hydroxyformamide Example 64A was sequentially converted to the corresponding oximes, hydroxylamine, and the final compound as described in Examples 2D, 2E, and 2F The crude product was purified on silica gel with 2.5% methanol/dichlormethane to provide the desired product as a colorless solid which was recrystallized from ethyl acetate/hexanes. mp 124–125° C.;

MS (DCI/NH$_3$) m/e 446 (M+H)$^+$ and 463 (M+NH$_4$)$^+$;

$^1$H NMR (300 MHz, CDCl$_3$) δ 9.90 (s; 0.5H), 9.58 (s; 0.5H), 8.32 (s; 0.5H), 7.92 (s; 0.5H), 7.65 (d; 2H; J=9 Hz), 7.61 (d; 2H; J=9 Hz), 7.47 (d; 2H; J=9 Hz), 6.99 (d; 1H; J=9 Hz), 6.97 (d; 1H; J=9 Hz), 4.86 (m; 0.5H), 4.42 (m; 0.5H), 4.08–4.23 (m; 2H), 3.82–3.70 (m; 1H), 3.55–3.65 (m; 1H), 2.80 (s; 1.5H), 2.78 (s; 1.5H), 1.30 (s; 3H), 1.28 (s; 3H);

Anal. calcd for $C_{22}H_{24}N_3O_5Cl$: C, 59.26; H, 5.42; N, 9.42. Found: C, 59.54; H, 5.61; N, 9.13.

EXAMPLE 65

(+)-N-(1-(((3'-cyanomethyl-(1,1'-biphenyl)-4-y)oxy)methyl)-2-(3,5,5-trimethyl-2,4-dioxo-1-imidazolidinyl)propyl)-N-hydroxyformamide

EXAMPLE 65A 1-(3-((3'-cyanomethyl-(1,1'-biphenyl)-4-yl)oxy)-propan-2-on-1-yl)-3,4,4-trimethyl-2,5-dioxoimidazolidine The desired product was prepared as in Example 5F substituting 4'-hydroxy-3-biphenylcarbonitrilemethane (0.95 g, 2.80 mmol) for 4'-hydroxy-4-biphenylcarbonitrile. Purification on silica gel with 100% ethyl acetate provided 0.78 g of the desired product. MS (DCI/NH$_3$) m/e 437 (M+NH$_4$)$^+$.

EXAMPLE 65B (+)-N-(1-(((3'-cyanomethyl-(1,1'-biphenyl)-4-y)oxy)methyl)-2-(3,4,4-trimethyl-2,5-dioxo-1-imidazolidinyl)propyl)-N-hydroxyformamide Example 65A (0.78 g, 1.87 mmol) was processed sequentially according to the precedures in Example 2D, 2E, and 2F without purification of the intermediates. Purification on silica gel with 100% ethyl acetate provided 500 mg (1.08 mmol) of the desired product.

$^1$H NMR (300 MHz, DMSO) δ 9.99 (s, 0.5H), 9.58 (s, 0.5H), 8.36 (s, 0.5H), 7.92 (s, 0.5H), d 7.60 (m, 4H), 7.46 (t, 1H J=8 Hz), 7.30 (d, 1H; J=8 Hz), 7.02 (d, 2H; J=8 Hz), 4.50 (m, 0.5H), 4.18 (m, 0.5H), 4.12 (s, 2H), 4.10 (m, 2H), 3.45 (m, 2H), 2.80 (s, 3H), 1.92 (m, 1H), 1.80 (m, 1H), 1.30 (s, 6H);

MS (DCI/NH$_3$) m/e 482 (M+NH$_4$)$^+$.

EXAMPLE 66

(+)-N-(1-(((4'-cyano-(1,1'-biphenyl)-4-y)oxy)methyl)-2-isopropylthioethyl)-N-hydroxyformamide

EXAMPLE 66A (+)-1-((4'-cyano-(1,1'-biphenyl)-4-y)oxy)-3-isopropylthio-2-propanol A solution of isopropylthiol (0.48 g, 6.4 mmol ) in THF (20 mL ) was treated with K$_2$CO$_3$ (0.5 g, 3.6 mmol ). After 30 minutes, 3-((4'-cyano-(1,1'-biphenyl)-4-y)oxy)-(1,2) oxirane (0.8 g, 3.19 mmol ) was added in a single portion. The resulting solution was stirred at 70° C. for 3 hours, quenched by adding excess aqueous sodium bicarbonate solution and partitioned between ethyl acetate and brine. The organic layer was dried (Na$_2$SO$_4$), filtered, and the product was purified on silica gel with 50% ethyl acetate/hexanes to provide 0.9 g (2.75 mmol, 86% ) of the desired product.

MS (DCI/NH$_3$) m/e 345 (M+NH$_4$)$^+$ and 362 (M+NH$_4$+NH$_3$)$^+$.

EXAMPLE 66B (+)-N-(1-(((4'-cyano-(1,1'-biphenyl)-4-y)oxy)methyl)-2isopropylthioethyl)-N-hydroxyformamide Example 66A was processed according to the procedures in Example 2C,2D, 2E, and 2F providing the desired product as a light orange foam.

$^1$H NMR (300 MHz, DMSO) δ 9.99 (s: 0.5H), 9.60 (s: 0.5H), 8.42 (s: 0.5H), 8.04 (s: 0.5H), d 7.85 (m; 4H), 7.75 (d; 2H J=9 Hz), 7.05 (d; 2H; J=9 Hz), 4.63 (m; 1H), 4.17 (m; 3H), 3.0 (m; 1H), 2.79 (m; 1H), 1.22 (dd; 6H; J=7.50 Hz);

MS (DCI/NH$_3$) m/e 388 (M+NH$_4$)$^+$.

EXAMPLE 67

(+)-N-(1-(((3'-cyanomethyl-(1,1'-biphenyl)-4-y)oxy)methyl)-2-(3,4,4-trimethyl-2,5-dioxo-1-imidazolidinyl)ethyl)-N-hydroxyformamide

EXAMPLE 67A (+)-1-(4-(3'-cyanoemethylphenyl)phenoxy)-3-(3,4,4-trimethyl-2,5-dioxo-1-imidazolidinyl)-2-propanol The desired product was prepared as in Example 4A substituting 4'-hydroxy-3-biphenylcarbonitrilemethane (170 mg, 0.64 mmol) and 3,5,5-trimethylhydantoin (37 mg, 0.96 mmol) for 4'-hydroxy-4-biphenylcarbonitrile and 5,5-dimethylhydantoin. Purification on silica gel with 100% ethyl acetate provided 130 g of the desired product.

MS (DCI/NH$_3$) m/e 415 (M+NH$_4$)$^+$.

EXAMPLE 67B (+)-N-(1-(((3'-cyanomethyl-(1,1'-biphenyl)-4-y)oxy) methyl)-2-(3,4,4-trimethyl-2,5-dioxo-1-imidazolidinyl)ethyl)-N-hydroxyformamide Example 67A was processed according to the procedures in Example 2C,2D, 2E, and 2F providing the desired product.

$^1$H NMR (300 MHz, DMSO) δ 9.86 (s: 0.5H), 9.58 (s: 0.5H), 8.34 (s: 0.5H), 7.92 (s: 0.5H), d 7.60 (m; 4H), 7.46 (t; 1H J=8 Hz), 7.30 (d; 1H; J=8 Hz), 7.02 (d; 2H; J=8 Hz), 4.85 (m; 0.5H), 4.42 (m; 0.5H), 4.10 (m; 2H), 4.12 (s; 2H), 3.68 (m; 1H), 3.62 (m; 1H), 2.80 (s; 3H), 1.30 (s: 6H);

MS (DCI/NH$_3$) m/e 468 (M+NH$_4$)$^+$.

EXAMPLE 68

(+)-N-(1-(((4'-cyano-(1,1'-biphenyl)-4yl)oxy) methyl)-2-(3-ethyl-4,4-dimethyl-2,5-dioxo-1-imidazolidinyl)ethyl)-N-hydroxyformamide

EXAMPLE 68A 4,4-dimethyl-2,5-dioxo-N-(4methoxoybenzyl) imidazolidine

A solution of 4,4-dimethyl-2,5-dioxoimidazolidine (17.0 g, 133 mmol), 4-methoxybenzyl chloride (30.0 g, 192 mmol), and potassium carbonate (27.5 g, 200 mmol) in dry DMF (600 mL) was heated at 80° C. under nitrogen for 3 hours. The mixture was concentrated to ¼ of the original volume and the resulting solution was partitioned between ethyl acetate and water. The aqueous layer was separated and extracted with ethyl acetate. The combined organic extracts were washed sequentially with water and brine, dried (Na$_2$SO$_4$), filtered, and concentrated to provide 32.97 g of a solid. Recrystallization from ethyl acetate and hexanes provided 24.5 g (74%) of the desired product.

mp 109–111° C.;

MS (DCI/NH$_3$) m/e 249 (M+H)$^+$ and 266 (M+NH$_4$)$^+$.

EXAMPLE 68B

3-Ethyl-1-(4'-methoxybenzyl)-2,5-dioxo-4,4-dimethylimidazolidine

A solution of 4,4-dimethyl-2,5-dioxo-N-(4-methoxoybenzyl)imidazolidine (3.5 g, 14.1 mmol) in THF (100 mL) was treated with sodium hydride (0.5 g, 21.2 mmol), stirred for 10 minutes, treated with iodoethane (3.3 g, 21.2 mmol), and stirred at 50° C. for 3 hours The mixture was then treated with HCl solution (10%) and partitioned between ethyl acetate and brine. The organic layer was dried, filtered and concentrated to provide 3.8 g (13.8 mmol, 98%) of the desired product as a white solid.

MS (DCI/NH$_3$) m/e 294 (M+NH$_4$).

EXAMPLE 68C 3-ethyl-2,5-dioxo-4,4-dimethylimidazolidine

A solution of 3-ethyl-1-(4'-methoxybenzyl)-2,5-dioxo-4, 4-dimethylimidazolidine (3.86 g, 14.0 mmol) in methoxy-benzene (100 mL) was treated with alumium trichloride (5.5 g, 42 mmol), stirred at 75° C. for 30 minutes, then poured into HCl solution (10%) and partitioned between ethyl acetate and brine. The organic layer was dried, filtered, and concentrated. Purification by recrystalization with ethyl acetate provided 2.1 g (13.5 mmol, 96%) of the desired prodcut as a white solid.

MS (DCI/NH$_3$) m/e 174 (M+NH$_4$)$^+$.

EXAMPLE 68D 1-((4'-cyano-(1,1'-biphenyl)-4y)oxy)-3-(3-ethyl-5,5-dimethyl-2,4-dioxo-1-imidazolidinyl)-2-propanone A solution of 3-ethyl-2,5-dioxo-4,4-dimethylimidazolidine (0.7 g, 4.5 mmol) in DMF (100 mL) was treated with potassium carbonate (0.6 g, 4.5 mmol) and 1-((4'-cyano-(1,1'-biphenyl)-4-y)oxy)-3-bromo-2-propynone (1.0 g, 3.0 mmol), stirred at 25° C. for 20 hours, then poured into aqueous HCl solution (10%) and partitioned between ethyl acetate and brine. The organic layer was dried, filtered, and concentrated. Purification on silica gel with 50% ethyl acetate provided 0.8 g (1.97 mmol, 66%) of the desired product as white solid.

MS (DCI/NH$_3$) m/e 424 (M+NH$_4$)$^+$.

EXAMPLE 68E (+)-N-(1-(((4'-cyano(1,1'-biphenyl)-4-yl)oxy) methyl)-2-(3-ethyl-4,4-dimethyl-2,5-dioxo-1-imidazolidinyl)ethyl-N-hydroxyformamide Example 68B (0.72 g, 1.77 mmol) was processed sequentially according to the precedures in Example 2D, 2E, and 2F without purification of the intermediates. Purification on silica gel with 60% ethyl acetate/hexanes provided 158 mg (0.35 mmol) of the desired product.

$^1$H NMR (300 MHz, DMSO) δ 9.85 (s, 0.5H), 9.54 (s, 0.5H), 8.32 (s, 0.5H), 7.94 (s, 0.5H), d 7.86 (m, 4H), 7.72 (d, 2H J=9 Hz), 7.08 (d, 2H, J=9 Hz), 4.85 (m, 0.5H), 4.42 (m, 0.5H), 4.18 (m, 2H), 3.78 (m, 1H), 3.62 (m, 1H), 1.32 (s, 6H), 1.12 (m, 3H). MS (DCI/NH$_3$) m/e 468 (M+NH$_4$)$^+$.

EXAMPLE 69

(+)-N-(1-(((4'-cyano-(1,1'-biphenyl)-4-yl)oxy) methyl)-2-(3-benzyl-4,4-dimethyl-2,5-dioxo-1-imidazolidinyl)ethyl)-N-hydroxyformamide

EXAMPLE 69A 3-benzyl-1-(4'-methoxybenzyl)-2,5-dioxo-4,4-dimethylimidazolidine The desired product was prepared as in Example 68B substituting benzyl iodine (3.9 g, 18 mmol) for iodoethane. Purification on silica gel with 50% ethyl acetate provided 4.0 g of the desired product.

MS (DCI/NH$_3$) m/e 356 (M+NH$_4$)$^+$.

EXAMPLE 69B 3-benzyl-2,5-dioxo-4,4-dimethylimidazolidine

A solution of 3-benzyl-1-(4'-methoxybenzyl)-2,5-dioxo-4,4-dimethylimidazolidine (3.9 g, 11.54 mmol) in acetonitrile (100 mL) was treated with a solution of ammonium cerium nitrate (31 g, 57.7 mmol) in 65 mL of water, stirred at 25° C. for 15 minutes, then diluted with ethyl acetate and partitioned between ethyl acetate and brine. The organic layer was dried, filtered, and concentrated. Purification by recrystalization with ethyl acetate/hexane provided 1.58 g (7.25 mmol, 63%) of the desired product as white solid.

MS (DCI/NH$_3$) m/e 236 M+NH$_4$)$^+$.

EXAMPLE 69C 1-((4'-cyano-(1,1'-biphenyl)-4-y)oxy)-3-(3-ethyl-4,4-dimethyl-2,5-dioxo-1-imidazolidinyl)-2-propanone The desired product was prepared as in Example 68D substituting 3-benzyl-2,5-dioxo-4,4-dimethylimidazolidine (0.5 g, 2.28 mmol) for 3-ethyl-2,5-dioxo-4,4-dimethylimidazolidine. Purification on silica gel with 30% ethyl acetate/chloroform provided 634 mg of the desired product.

MS (DCI/NH$_3$) m/e 485 (M+NH$_4$)$^+$.

EXAMPLE 69D (+)-N-(1-(((4'-cyano-(1,1'-biphenyl)-4-yl)oxy)methyl)-2-(3-ethyl-4,4-dimethyl-2,5-dioxo-1-imidazolidinyl)ethyl)N-hydroxyformamide Example 69C (0.62 g, 1.33 mmol) was processed sequentially according to the procedures in Example 2D, 2E, and 2F without purification of the intermediates. Purification on silica gel with 70% ethyl acetate/hexanes provided 230 mg (0.45 mmol) of the desired product.

$^1$H NMR (300 MHz, DMSO) δ 9.95 (s, 0.5H), 9.64 (s, 0.5H), 8.35 (s, 0.5H), 7.94 (s, 0.5H), d 7.86 (m, 4H), 7.75 (d, 2H, J=9 Hz), 7.30 (d, 2H, J=9 Hz), 7.25 (m, 3H), 7.06 (m, 2H), 4.90 (m, 0.5H), 4.52 (s, 2H), 4.50 (m, 0.5H), 4.18 (m, 2H), 3.82 (m, 1H), 3.62 (m, 1H), 1.22 (s, 6H);

MS (DCI/NH$_3$) m/e 530 (M+NH$_4$)$^+$.

EXAMPLE 70

(+)-N-(1-(((4'-cyano-(1,1'-biphenyl)-4-y)oxy)methyl)-2-(3,5,5-trimethyl-2,4-dioxo-1-imidazolidinyl)ethyl)-N-hydroxyformamide

EXAMPLE 70A 1-((4'-cyano-(1,1'-biphenyl)-4-y)oxy)-3-(3,5,5-trimethyl-2,4-dioxo-1-imidazolidinyl)-2-propanol A solution of 5,5-dimethylhydantoin (2.0 g, 15.6 mmol) in DMF (20 mL) was treated with sodium tert-butoxide (1.5 g, 15.6 mmol), stirred for 10 minute, treated with iodomethane (2.2 g, 15.6 mmol), stirred at 40° C. for 3 hours. The resulting solution was treated with sodium tert-butoxide (1.5 g, 15.6 mmol) followed by 3-((4'-cyano-(1,1'-biphenyl)-4-y)oxy)-(1,2) oxirane (1.15 g, 4.58 mmol ), stirred at 100° C. for 20 minutes, treated with HCl solution (10%) and partitioned between ethyl acetate and brine. The organic layer was dried and concentrated to provide 1.35 g (75%) of the desired product as white solid.

MS (DCI/NH$_3$) m/e 411 (M+NH$_4$).

EXAMPLE 70B 1-((4'-cyano-(1,1'-biphenyl)-4-y)oxy)-3-(3,5,5-trimethyl-2,4-dioxo-1-imidazolidinyl)-2-propanone Example 70A (1.35 g g, 3.4 mmol) was processed according to the procedures in Example 2C. Purification on silica gel with 30% ethyl acetate provided 1.2 g (3.1 mmol, 90%) of the desired product.

MS (DCI/NH$_3$) m/e 409 (M+NH$_4$)$^+$.

EXAMPLE 70C (+)-N-(1-(((4'-cyano-(1,1'-biphenyl)-4-y)oxy)methyl)-2-(3,5,5-trimethyl-2,4-dioxo-1-imidazolidinyl)ethyl)-N-hydroxyformamide Example A-264890.0B (1.2 g, 3.07 mmol) was processed sequentially according to the precedures in Example 2D, 2E, and 2F without purification of the intermediates. Purification on silica gel with 30% ethyl acetate/hexanes provided 380 mg (2.29 mmol) of the desired product.

$^1$H NMR (300 MHz, DMSO) δ 9.90 (s, 0.5H), 9.68 (s, 0.5H), 8.38 (s, 0.5H), 7.98 (s, 0.5H), d 7.88 (m, 4H), 7.72 (d, 2H, J=9 Hz), 7.08 (d, 2H, J=9 Hz), 4.92 (m, 0.5H), 4.42 (m, 0.5H), 4.20 (m, 2H), 3.50 (m, 2H), 2.88 (s, 3H), 1.32 (s, 6H);

MS (DCI/NH$_3$) m/e 454 (M+NH$_4$)$^+$.

EXAMPLE 71

N-(1-(((4'-methoxy(1,1'-biphenyl)-4-yl)sulfonyl)methyl)ethyl)-N-hydroxyformamide

EXAMPLE 71A

4'-methoxy-4-thiomethyl Biphenyl

A solution of 4-bromothioanisole (6.15 g, 29.4 mmol) in DMF (60 mL) was treated sequentially with palladium (II) acetate (0.34 g, 1.5 mmol) and tri-o-tolylphosphine (0.94 g, 3.0 mmol) then 4-methoxyphenylboronic acid (5.06 g, 32.3 mmol) and cesium carbonate (19.2 g, 58.8 mmol). The mixture was stirred at 75° C. for 8 hours, then room temperature for 15 hours. The resulting suspension was partitioned between water and ether/hexane, 2:1. The organic layer was dried with Mg$_2$SO$_4$, filtered, and concentrated to provide crude product as a yellow solid. Recrystallization in ether at −20° C. afforded 2.61 g (39%) of the desired product.

MS (ESI+) m/e 231 (M+H).

EXAMPLE 71B

4(4'-methoxyphenyl)-phenyl Methyl Sulfone

A solution of Example 71A (2.61 g, 11.3 mmol) in chloroform (100 mL) was treated with m-chloroperbenzoic acid (6.52 g, 22.7 mmol), stirred at 0° C. for 3 hours and then warmed to 10° C. over 1 hour. The mixture was partitioned between dilute sodium bicarbonate aqueous solution and chloroform, dried (Mg2SO4), filtered, and concentrated to provide crude product as a white solid. Recrystallization from dichloromethane and ether afforded 1.89 g (64%) of the desired product.

MS (ESI+) m/e 263 (M+H) and 280 (M+NH$_4$).

EXAMPLE 71C

N-(1-(((4'-methoxy(1,1'-biphenyl)-4-yl)sulfonyl)methyl)ethyl)-N-benzyloxy Amine

A suspension of Example 71B (0.26 g, 1.0 mmol) in THF (40 mL) cooled to −78° C. under argon atmosphere was treated with n-BuLi (0.40 mL of a 2.5 M solution in hexane, 1.0 mmol) and stirred for 3 hours. The resulting suspension was treated with BF$_3$.Et$_2$O (0.127 mL, 1.0 mmol) then the O-Benzyloxime of acetaldehyde (0.15 g, 1.0 mmol) (Stewart, et. al. J. Med. Chem. 1997, vol. 40, number 13, pages 1955–1968) in THF (10 mL), and stirred 1 hour at −78° C. and 1 hour at 25° C. The mixture was partitioned between ether and pH 7 phosphate buffer. The organic extracts were washed with brine, dried (Mg$_2$SO$_4$), filtered, and concentrated to afford crude product as a white powder which was purified on silica gel with dichloromethane/methanol to provide 0.15 g (36%) of the desired product.

MS (ESI+) m/e 412 (M+H).

EXAMPLE 71D

N-(1-(((4'-methoxy(1,1'-biphenyl)-4-yl)sulfonyl)methyl)ethyl)-N-nenzyloxyformamide A solution of Example 71c (0.11 g, 0.27 mmol) in THF (50 mL) cooled to 0° C. under argon atmosphere was treated with formic acetic anhydride (0.24 g, 2.7 mmol), stirred for 5 minutes at 0° C. then room temperature for 16 hours. Partitioned between 1 N HCl and ethyl acetate. The organic phase was washed with brine, dried (Mg$_2$SO$_4$), filtered, and concentrated to provide crude oil product which was purified on silica gel with dichloromethane/methanol to afford 114 mg (96%) of the desired product.

MS (ESI+) m/e 440 (M+H) and 457 (M+NH$_4$).

EXAMPLE 71E

N-(1-(((4'-methoxy(1,1'-biphenyl)-4-yl)sulfonyl)methyl)ethyl)-N-hydroxyformamide A solution of Example 71D (114 mg, 0.26 mmol) in THF (20 mL) was treated with 10% palladium on carbon (35 mg, catalytic amount) and hydrogen gas at atmospheric pressure and stirred at RT for 18 hours. Filtration of the suspension through a pad of diatomaceou earth (Celite®) and concentration provided the crude product as a white solid which was purified by trituration in ethyl acetate to afford 66 mg (73%) of the desired product.

mp 197–198° C.;

$^1$H NMR (DMSO-d6) δ 1.16 (d, 1.5H, J=6.6 Hz), 1.22 (d, 1.5H, J=6.6 Hz), 3.43–3.70 (m, 2H), 3.82 (s, 3H), 4.28–4.41 (m, 0.5H), 4.62–4.76 (m, 0.5H), 7.08 (d, 2H, J=8.7 Hz), 7.74 (d, 2H, J=8.7 Hz), 7.87–7.96 (m, 4.5H), 8.08 (s, 0.5H), 9.47 (s, 0.5H), 9.89 (s, 0.5H);

MS (ESI+) m/e 350 (M+H), 367 (M+NH$_4$);

Anal. Calcd for: C$_{17}$H$_{19}$NO$_5$S.H2O C, 55.57; H, 5.76; N, 3.81. Found: C, 55.32; H, 5.20; N, 3.67.

EXAMPLE 72

N-(1-(((4'-chloro(1,1'-biphenyl)-4-yl)sulfonyl)methyl)ethyl)-N-hydroxyformamide

The desired product was synthesized according to the procedures described in Example 71 substituting 4-chlorophenylboronic acid for 4-methoxyphenylboronic acid in Example 71A. Purification of the crude final product by recrystallization in ethyl acetate afforded 36 mg of the desired product.

mp 178–180° C.;

1H NMR (DMSO-d6) δ 1.16 (d, 1.5H, J=6.6 Hz), 1.22 (d, 1.5H, J=6.6 Hz), 3.50 (dd, 1H, J=4.8,14.7 Hz), 3.57–3.73 (m, 1H), 4.28–4.41 (m, 0.5H), 4.61–4.77 (m, 0.5H), 7.59 (d, 2H, J=8.4 Hz), 7.81 (d, 2H, J=8.4 Hz), 7.91 (s, 0.5H), 7.92–8.00 (m, 4H), 8.07 (s, 0.5H), 9.45 (s, 0.5H), 9.86 (s, 0.5H);

MS (ESI+) m/e 354 (M+H), 376 (M+Na);

Anal. Calcd for: C$_{36}$H$_{16}$NO$_4$SCl C, 54.31; H, 4.55; N, 3.95. Found: C, 54.46; H, 4.43; N, 3.85.

EXAMPLE 73

N-(1-(((4-(1,3-benzodioxol-5-yl)phenyl)sulfonyl)methyl)ethyl)-N-hydroxyformamide The desired product was synthesized according to the procedures described in Example 71 substituting 3,4-methylenedioxybenzeneboronic acid for 4-methoxyphenylboronic acid in Example 71A. mp 200–201° C.;

1H NMR (DMSO-d6) δ 1.16 (d, 1.5H, J=6.6 Hz), 1.22 (d, 1.5H, J=6.6 Hz), 3.44–3.70 (m, 2H), 4.28–4.40 (m, 0.5H), 4.61–4.76 (m, 0.5H), 6.11 (s, 2H), 7.06 (d, 1H, J=7.8 Hz), 7.29 (d, 1H, J=8.4 Hz), 7.39 (s, 1H), 7.8–7.94 (m, 4.5H), 8.08 (s, 0.5H), 9.48 (s, 0.5H), 9.90 (s, 0.5H);

MS (ESI+) 364 (M+H), 381 (M+NH$_4$);

Anal. Calcd for: C$_{17}$H$_{17}$NO$_6$S C, 56.19; H, 4.71; N, 3.85. Found: C, 55.97; H, 4.62; N, 3.81.

EXAMPLE 74

N-(1-(((4-(4-chlorophenoxy)phenyl)sulfonyl)methyl)ethyl)-N-hydroxyformamide

EXAMPLE 74A 4-chlorophenoxyphenyl Methyl Sulfone

A solution of 4-chlorophenol (5.54 g, 43 mmol) in DMSO (75 mL) was treated sequentially with potassium t-butoxide (5.15 g, 46 mmol) then with a solution of 4-fluorophenyl methyl sulfone (5.00 g, 29 mmol) in DMSO (25 mL), heated at 120° C. for 2 hours, cooled to room temperature, then partitioned between dichloromethane and 1 N sodium hydroxide, dried (Mg$_2$SO$_4$), filtered, and concentrated to give crude product as a white solid. Recrystallization from ethyl acetate and hexane afforded 5.44 g (66%) of the desired product.

MS (ESI+) m/e 300 (M+NH$_4$).

EXAMPLE 74B

N-(1-(((4-(4-chlorophenoxy)phenyl)sulfonyl)methyl)ethyl)-N-hydroxyformamide

The desired product was prepared from Example 74A according to the procedures described in Example 71C–71E. Purification of the crude final compound by recrystallization in ethyl acetate afforded 388 mg of the desired product.

mp 144–145° C.;

1H NMR (DMSO-d6) δ 1.15 (d, 1.5H, J=6.6 Hz), 1.21 (d, 1.5H, J=6.6 Hz), 3.39–3.68 (m, 2H), 4.25–4.37 (m, 0.5H), 4.604.70 (m, 0.5H), 7.16–7.23 (m, 4H), 7.53 (d, 2H, J=8.9 Hz), 7.83–7.92 (m, 2.5H), 8.06 (s, 0.5H), 9.45 (s, 0.5H), 9.87 (s, 0.5H);

MS (ESI+) 370 (M+H), 387 (M+NH$_4$);

Anal. Calcd for: C$_{16}$H$_{16}$NO$_5$SCl C, 51.96; H, 4.36; N, 3.78. Found: C, 52.22; H, 4.37; N, 3.80.

EXAMPLE 75

N-(1-(((4'-methoxy(1,1'-biphenyl)-4-yl)sulfonyl)methy propyl)-N-hydroxyformamide

EXAMPLE 75A 1-(4'-methoxy(1,1'-biphenyl)-4-yl)sulfonyl)-2-butanol

A solution of Example 71B (0.70 g, 2.67 mmol) in THF (200 mL) cooled to −78° C. under argon was treated with n-BuLi (1.17 mL of 2.5 M solution in hexane, 2.93 mmol), stirred 4 hours at −78° C., then treated with propionaldehyde (0.40 mL, 5.34 mmol) dropwise. Allowed reaction mixture to warm to room temperature over 1.5 hours, quenched with saturated aqueous NH$_4$Cl solution (50 mL), partitioned between ether and water, dried (Mg$_2$SO$_4$), filtered, and concentrated to afford 0.90 g of crude product which was purified on silica gel with dichloromethane/methanol to provide 0.78 g (91%) of the desired product.

MS (ESI+) m/e 321 (M+H), 338 (M+NH).

EXAMPLE 75B 1-(4'-methoxy(1,1'-biphenyl)-4-yl)sulfonyl)-1-butene

A solution of Example 75A (0.45 g, 1.401 mmol) in dichloromethane (40 mL) cooled to 0° C. was treated sequentially with triethylamine (0.29 mL, 2.11 mmol) and methanesulfonyl chloride (0.12 mL, 1.55 mmol) dropwise. Stirred at RT for 3 hours then treated with 1,8-diazabicyclo (5.4.0)undec-7-ene (0.21 mL, 1.40 mmol), refluxed for 2 hours, cooled to room temperature, and partitioned between dilute sodium bicarbonate solution and dichloromethane. The organic extract was washed with 1 N HCl, then brine, dried (Mg$_2$SO$_4$), filtered, and concentrated to afford white solid crude product. Recrystallization in ether at −20° C. provided 0.34 g (80%) of the desired product.

MS (ESI+) m/e 303 (M+H), 320 (M+NH$_4$).

EXAMPLE 75C

N-(1-(((4'-methoxy(1,1'-biphenyl)-4-yl)sulfonyl)methyl)propyl)-N-hydroxy Amine

A solution of Example 75B (0.34 g, 1.12 mmol) in THF (40 mL) was treated with hydroxylamine hydrochloride (0.39 g, 5.62 mmol) and potassium carbonate (0.78 g, 5.62 mmol), refluxed for 5 hours, cooled to room temperature, partitioned between ether and water, dried (Mg$_2$SO$_4$), and concentrated to give crude product as a clear, colorless oil. Recrystallization from ethyl acetate and ether provided 0.25 g (67%) of the desired product.

MS (ESI+) m/e 336 (M+H).

EXAMPLE 75D

N-(1-(((4'-methoxy(1,1'-biphenyl)-4-yl)sulfonyl)methyl)propyl)-N-hydroxyformamide A solution of Example 75C (0.24 g, 0.72 mmol) in THF (30mL) cooled to 0° C. was treated with formic acetic anhydride (64 mg, 0.72 mmol), stirred for 2 hours, partitioned between water and dichloromethane, dried (Mg$_2$SO$_4$), filtered, and concentrated to afford 0.25 g of crude product which was recrystallized in ethyl acetate to provide 106 mg (41%) of the desired product.

mp 199–200° C.;

1H NMR (DMSO-d6) δ 0.69–0.80 (m, 3H), 1.40–1.69 (m, 2H), 3.41–3.69 (m, 2H), 3.82 (s, 3H), 3.96–4.07 (m, 0.5H), 4.43–4.54 (m, 0.5H), 7.08 (d, 2H, J=9.0 Hz), 7.71–7.78 (m, 2H), 7.87–7.96 (m, 4.5H), 8.17 (s, 0.5H), 9.49 (s, 0.5H), 9.84 (s, 0.5H);

MS (ESI+) 364 (M+H), 381 (M+NH);

Anal. Calcd for: C$_{18}$H$_{21}$NO$_5$S C, 59.48; H, 5.82; N, 3.85. Found: C, 59.67; H, 5.77; N, 3.80.

EXAMPLE 76

N-(1-(1,1-dimethyl-2-((4'-(trifluoromethyl(1,1'-biphenyl)-4-yl)sulfonyl)ethyl)-N-hydroxyformamide

EXAMPLE 76A 4-(4'-trifluoromethylphenyl)-phenyl Methyl Sulfone

The desired product was prepared according to the procedure given in Example 73A substituting 4-trifluoromethylphenylboronic acid for 3,4-methylenedioxybenzene-boronic acid. Purification by recrystallization in ethyl acetate and ether afforded 3.70 g (72%) of the desired product.

MS (ESI+) m/e 318 (M+NH$_4$).

EXAMPLE 76B 1-(4'-trifluoromethyl(1,1'-biphenyl)-4-yl)sulfonyl)-2-methyl-2-propanol The desired product was prepared according to the procedure described in Example 75A substituting Example 76A for Example 71B and substituting acetone for propionaldehyde. Purification of crude product by recrystallization in ethyl acetate, ether, and pentane provided 1.40 g (73%) of the desired product.

MS (ESI+) m/e 376 (M+NH$_4$).

EXAMPLE 76C

N-(1-(1,1-dimethyl-2-((4'-(trifluoromethyl)(1,1'-biphenyl)-4-yl)sulfonyl)ethyl)-N-hydroxyformamide The desired product was prepared from Example 76B according to the procedures described in Examples 75B, 75C and 75D. Purification of the final product by recrystallization in ethyl acetate and ether provided 17 mg of the desired product.

mp 167–169° C.;

1H NMR (DMSO-d6) δ 1.52 (s, 6H), 3.71 (s, 2H), 7.83–8.03 (m, 8.5H), 8.17 (s, 0.5H), 9.43 (s, 0.5H), 10.0 (s, 0.5H);

MS (ESI+) 402 (M+H), 419 (M+NH$_4$), 424 (M+Na);

Anal. Calcd for: C$_{18}$H$_{18}$NO$_4$F$_3$SC, 53.86; H, 4.52; N, 3.48. Found: C, 53.58; H, 4.48; N, 3.19.

EXAMPLE 77

N-(1-(phenylmethoxy)methyl)-2-((4'-(trifluoromethyl)(1,1'-biphenyl)-4-yl)sulfonyl)ethyl)-N-hydroxyformamide The desired product was synthesized according to the procedures described in Examples 75A–75D substituting Example 76A for Example 71B and substituting benzyloxyacetaldehyde for propionaldehyde in Example 75A. Purification of the crude final product by recrystallization in ethyl acetate afforded 0.53 g of the desired product.

mp 172° C.;

1H NMR (DMSO-d6) δ 3.37–3.61 (m, 3H), 3.61–3.72 (m, 1H), 4.28–4.50 (m, 2.5H), 4.81–4.93 (m, 0.5H), 7.20–7.35 (m, 5H), 7.85–8.06 (m, 8.5H), 8.18 (s, 0.5H), 9.57 (s, 0.5H), 9.96 (s, 0.5H);

MS (ESI+) 494 (M+H), 511 (M+NH$_4$);

Anal. Calcd for: C$_{24}$H$_{22}$NO$_5$F$_3$S C, 58.41; H, 4.49; N, 2.83. Found: C, 58.43; H, 4.54; N, 2.77.

EXAMPLE 78

N-(1-(hydroxymethyl)-2-(((4'-(trifluoromethyl)(1,1'-biphenyl)-4-yl)sulfonyl)ethyl)-N-hydroxyformamide A solution of Example 78 (35 mg, 0.07 mmol) in THF (3 mL) and methanol (5 mL) was treated with palladium on carbon, 10% (30 mg, 0.03 mmol) and hydrogen gas at atmospheric pressure, stirred at room temperature for 16 hours, filtered through diatomaceous earth (Celite®), and concentrated to afford crude product. Purification by recrystallizations in ethyl acetate, ether, and hexane provided 20 mg (70%) of the desired product.

mp 159–161° C.;

1H NMR (DMSO-d6) δ 3.25–3.68 (m, 4H), 3.98–4.10 (m, 0.5H), 4.54–4.66 (m, 0.5H), 4.97–5.09 (m, 1H), 7.81–8.07 (m, 8.5H), 8.14 (s, 0.5H), 9.44 (s, 0.5H), 9.85 (s, 0.5H); MS (ESI+) 404 (M+H), 421 (M+NH$_4$), 426 (M+Na);

Anal. Calcd for: $C_{17}H_{16}NO_5F_3S$ C, 50.61; H, 3.99; N, 3.47. Found: C, 50.57; H, 3.93; N, 3.37.

EXAMPLE 79

N-(1-((4,4-dimethy-2,5-dioxo-1-imidazolidinyl)methyl)-2-((4'-(trifluoromethyl)(1,1'-biphenyl)-4-yl)thio)ethyl)-N-hydroxyformamide

EXAMPLE 79A 1-((4'-trifluoromethyl(1,1'-biphenyl)-4-yl)thio)-3-(4,4-dimethyl-2,5-dioxoimidazolidin-1-yl)-2-propanone The mixture of Example 46A (698 mg, 1.88 mmol), tetrakis(triphenyphosphine) palladium(0) (217 mg, 0.19 mmol), 4-triflorophenylboronic acid (714 mg, 3.76 mmol) and NaOH (1M, 3.76 mL, 3.76 mmol) in DME (20 mL) was refluxed under argon for 4 hours. The mixture was evaporated to a small volume, and partitioned between dichloromethane/brine. The dichloromethane layer was collected, dried (Na$_2$SO$_4$), filtered and evaporated to dryness. Purification of the crude final product on silica gel with 20%–40% ethyl acetate/dichloromethane provided 0.820 g of the desired product. MS (DCI/NH$_3$) m/e 454 (M+NH$_4$)$^+$, 437 (M+H)$^+$.

EXAMPLE 79B

N-(1-((4,4-dimethy-2,5-dioxo-1-imidazolidinyl)methyl)-2-((4'-(trifluoromethyl)(1,1'-biphenyl)-4-yl)thio)ethyl)-N-hydroxyformamide The desired product was obtained following the procedures in Examples 2D–F (inclusive) but substituting Example 79A (0.82 g, 1.88 mmol) for Example 2C. Purification of the crude final product on silica gel with 5% methanol/dichloromethane provided 434 mg of the desired product.

mp 172–174° C.;

$^1$H NMR (300 MHz, d$_6$-DMSO) δ 9.75 and 9.52 (br s, 1H), 8.37 and 8.33 (s, 1H), 8.31 and 7.77 (s, 1H), 7.90 (d, 2H, J=8.4 Hz), 7.81 (d, 2H, J=8.4 Hz), 7.71 (m, 2H), 7.47 (m 2H), 4.60 and 4.09 (m, 1H), 3.52–3.77 (m, 2H), 3.08–3.46 (m, 2H), 1.28 and 1.25 and 1.23 (s, 6H);

MS (DCI/NH$_3$) m/e499 (M+NH$_4$)$^+$, 482 (M+H)$^+$;

Anal. calcd for $C_{22}H_{22}F_3N_3O_4S.0.5$ CH$_3$OH: C, 54.31; H, 4.86; N, 8.44. Found: C, 54.43; H, 4.82; N, 8.08.

EXAMPLE 80

N-(1-((4,4-dimethy-2,5-dioxo-1-imidazolidinyl)methyl)-2-((4'-(trifluoromethyl)(1,1'-biphenyl)-4yl)sulfonyl)ethyl)-N-hydroxyformamide Example 79 was converted to Example 80 following the procedure described in Example 46D.

mp 180–182° C.;

$^1$H NMR (300 MHz, d$_6$-DMSO) d 9.66 and 9.51 (br s, 1H), 8.39 and 8.35 (s, 1H), 8.10 and 7.73 (s, 1H), 7.79–8.02 (m, 6H), 7.89 (d, 2H, J=8.4 Hz), 4.91 and 4.55 (m, 1H), 3.45–3.80 (m, 4H), 1.24 and 1.23 and 1.21 (s, 6H).

MS (DCI/NH$_3$) m/e531 (M+NH$_4$)$^+$, 514 (M+H)+;

Anal. calcd for $C_{22}H_{22}F_3N_3O_6S.0.75$ H$_2$O: C, 50.14; H, 4.49; N, 7.97. Found: C, 50.27; H, 4.49; N, 7.97.

EXAMPLE 81

N-(1-((2,5-dioxo-1-imidazolidinyl)methyl)-2-((4'-(trifluoromethoxy)(1,1'-biphenyl)-4-yl)oxy)ethyl)-N-hydroxyformamide

EXAMPLE 81A 1-bromo-3-(2,5-dioxoimidazolidin-1-yl)propan-2-one

The desired product was prepared following the procedures in Examples 16A and 16B, substituting hydantoin for 1,5,5-trimethylhydantoin.

EXAMPLE 81B

N-(1-((2,5-dioxo-1-imidazolidinyl)methyl)-2-((4'-(trifluoromethoxy)(1,1'-biphenyl)-4-yl)oxy)ethyl)-N-hydroxyformamide The desired product was prepared following the sequence described in described in Examples 16C and 16E, substituting 81A for 16B and 4-(4'-trifluoromethoxy-phenyl)-phenol for 4-bromophenol.

$^1$H NMR (DMSO-δ6) δ 9.92 (s, 0.5H), 9.60 (bs, 0.5H), 8.31 (s, 0.5H), 8.16 (s, 0.5H), 8.14 (s, 0.5H), 7.92 (s, 0.5H), 7.76–7.72 (m, 4H), 7.64–7.62 (d, 4H, J=8.4 Hz), 7.42–7.40 (d, 4H, J=8.6 Hz), 7.02–6.98 (m, 4H), 4.84–4.82 (m, 0.5H), 4.38–4.35 (m, 0.5H), 4.19–4.04 (4H);

Anal. Calcd for: $C_{20}H_{18}N_3O_6F_3$: C, 52.98; H, 4.00; N, 9.13. Found: C, 53.01; H, 4.03; N, 9.13.

EXAMPLE 82

N-(1-(((4'-(trifluoromethyl)(1,1'-biphenyl)-4-yl)sulfonyl)methyl)-2-(3,4,4-trimethyl-2,5-dioxo-1-imidazolidinyl)ethyl)-N-hydroxyformamide The desired product was prepared following the procedures described in Example 46A, 46B, 46C and 46D, substituting Example 16B for 23A in Example 46A and 4-trifluoromethylbenzeneboronic acid for 4butyloxybenzeneboronic acid in Example 46B.

$^1$H NMR (d6-DMSO) δ 9.70 (s, 0.5H), 9.54 (s, 0.5H), 8.10 (s, 0.5H), 8.05–7.97 (m, 6H), 7.89 (d, 2H, J=7.8 Hz), 7.75 (s, 0.5H), 4.97–4.86 (m, 0.5H), 4.60–4.48 (m, 0.5H), 3.80–344 (m, 4H), 2.75 (s, 3H), 1.24 (s, 3H), 1.22 (s, 3H);

MS (ESI) 528 (M+H), 545 (M+NH$_4$), 526 (M−H);

Anal. Calcd for: $C_{23}H_{24}N_3O_6SF_3$ C, 52.36; H, 4.58; N, 7.96. Found: C, 52.05; H, 4.70; N, 7.63.

EXAMPLE 83

N-(1-(((4'-butyl(1,1'-biphenyl)-4-yl)oxy)methyl)-2-(3-methy-2,5-dioxo-1-imidazolidinyl)ethyl)-N-hydroxyformamide The desired product was prepared following the procedures described in Example 16C and 16E, substituting Example 26A for 16B and 4-(4'-butylphenyl)phenol for 4-bromophenol.

$^1$H NMR (d6-DMSO) δ 10.00–9.94 (br, 0.5H), 9.64–9.58 (br, 0.5H), 8.34 (s, 0.5H), 7.98 (s, 0.5H), 7.58 (d, 2H, J=8.8

Hz), 7.52 (d, 2H, J=8.6 Hz), 7.24 (d, 2H, J=8.5 Hz), 7.00–6.92 (m, 2H), 4.92–4.79 (m, 0.5H), 4.41–4.30 (m, 0.5H), 4.20–4.03 (m, 2H), 3.95 (d, 2H, J=7.8 Hz), 3.75–3.57 (m, 2H), 2.86 (s, 1.5H), 2.85 (s, 1.5H), 2.60 (t, 2H, J=7.4 Hz), 1.63–1.51 (m, 2H), 1.39–1.25 (m, 2H), 0.91 (t, 3H, J=7.4 Hz);

MS (ESI) 440 (M+H), 457 (M+NH$_4$), 438 (M−H);

Anal. Calcd for: C$_{24}$H$_{29}$N$_3$O$_5$.0.25 H$_2$O C, 64.92; 1, 6.69; N, 9.46. Found: C, 64.76; H, 6.62; N, 9.29.

EXAMPLE 84

N-(1-((3-methy-2,5-dioxo-1-imidazolidinyl)methyl)-2-((4'-(trifluoromethoxy)(1,1'-biphenyl)-4-yl)oxy)ethyl)-N-hydroxyformamide The desired product was prepared following the procedures described in Example 16C and 16E, substituting Example 26A for 16B and 4-(4'-trifluoromethoxy)phenol for 4-bromophenol.

$^1$H NMR (d6-DMSO) δ 10.02–9.92 (br, 0.5H), 9.64–9.58 (br, 0.5H), 8.35 (s, 0.5H), 7.98 (s, 0.5H), 7.74 (d, 2H, J=8.9 Hz), 7.64 (d, 2H, J=8.8 Hz), 7.41 (d, 2H, J=8.1 Hz), 7.03–6.97 (m, 2H), 4.91–4.82 (m, 0.5H), 4.41–4.31 (m, 0.5H), 4.21–4.07 (m, 2H), 3.96 (d, 2H, J=7.7 Hz), 3.72–3.57 (m, 2H), 2.86 (s, 1.5H), 2.85 (s, 1.5H);

MS (ESI) 468 (M+H), 485 (M+NH$_4$), 466 (M−H);

Anal. Calcd for: C$_{21}$H$_{20}$N$_3$O$_6$F$_3$ C, 53.96; H, 4.31; N, 8.99. Found: C, 53.85; H, 4.40; N, 8.85.

EXAMPLE 85

N-(4-(4-((4'-chloro(1,1'-biphenyl)-4-yl)sulfonyl)methyl)tetrahydro-2H-pyran-4-yl)-N-hydroxyformamide

EXAMPLE 85A

N-(4-(4-((4'-chloro(1,1'-biphenyl)-4-yl)sulfonyl)methyl)tetrahydro-2H-pyran-4-yl)-N-benzyloxy Amine The desired product was prepared following the procedure described in Example 54A, substituting 4'-chloro-4-methylsulfone-biphenyl for phenoxyphenyl-4-chloro-4'-methylsulfone.

EXAMPLE 85B

N-(4-(4-((4'-chloro(1,1'-biphenyl)-4-yl)sulfonyl)methyl)tetrahydro-2H-pyran-4-yl)-N-hydroxy Amine A solution of Example 85A (0.436 g, 0.92 mmol) was treated with (CF$_3$CO$_2$)$_3$B (4.6 mL, 1M solution in THF, 4.6 mmol), then stirred overnight at room temperature. The solution was concentrated, partitioned between ethyl acetate and aq. Na$_2$CO$_3$ and the organic layer was dried (Mg$_2$SO$_4$), filtered, concentrated and purified via column chromatography to give the desired product in 51% yield.

EXAMPLE 85C

N-(4-(4-((4'-chloro(1,1'-biphenyl)-4-yl)sulfonyl)methyl)tetrahydro-2H-pyran-4-yl)-N-hydroxyformamide Example 85B was converted to the desired product using the formylation procedure of Example 2F.

$^1$H NMR (d6-DMSO) δ 9.52–9.48 (br, 1H), 8.23 (s, 1H), 7.97 (s, 4H), 7.81 (d, 2H, J=8.4 Hz), 7.59 (d, 2H, J=8.5 Hz), 3.72 (s, 2H), 3.69–3.46 (m, 4H), 2.35–1.94 (m, 4H);

MS (ESI) 410 (M+H), 427 (M+NH$_4$), 432 (M+Na), 408 (M−H).

EXAMPLE 86

N-(1-(((4-(4-chlorophenoxy)phenyl)sulfonyl)methyl)-2-(4,4-dimethyl-2,5-dioxo-1-imidazolidinyl)ethyl)-N-hydroxyformamide The desired product was prepared following the procedures described in Examples 46A, 46C and 46D, substituting 4-(4'-chlorophenoxy)thiophenolinstead of 4-bromothiophenol.

$^1$H NMR (d6-DMSO) δ 9.67 (s, 0.5H), 9.50 (s, 0.5H), 8.36 (d, 1H, J=13.2 Hz), 8.10 (s, 0.5H), 7.90 (dd, 2H, J=8.8, 3.0 Hz), 7.68 (s, 0.5H), 7.53 (d, 2H, J=8.8 Hz), 7.20 (d, 4H, J=8.8 Hz), 4.89–4.77 (m, 0.5H), 4.52–4.40 (m, 0.5H), 3.68–3.38 (m, 4H), 1.25–1.21 (m, 6H);

MS (ESI) 496 (M+H), 513 (M+NH$_4$), 494 (M−H);

Anal. Calcd for: C$_{21}$H$_{22}$N$_3$O$_7$SCl C, 50.85; H, 4.47; N, 8.47. Found: C, 50.53; H, 4.58; N, 8.25.

EXAMPLE 87

N-(1-(((4-(4-chlorophenoxy)phenyl)sulfonyl)methyl)-2-(3,4,4-trimethyl-2,5-dioxo-1-imidazolidinyl)ethyl)-N-hydroxyformamide The desired product was prepared following the procedures described in Examples 46A, 46C and 46D, substituting 16B for 23A and 4-(4'-chlorophenoxy)thiophenol instead of 4-bromothiophenol.

$^1$H NMR (d6-DMSO) δ 9.78–9.71 (m, 0.5H), 9.58–9.49 (m, 0.5H), 8.09 (s, 0.5H), 7.89 (dd, 2H, J=5.8, 2.9 Hz), 7.68 (s, 0.5H), 7.53 (d, 2H, J=9.2 Hz), 7.20 (d, 4H, J=8.8 Hz), 4.88–4.78 (m, 0.5H), 4.50–4.38 (m, 0.5H), 3.72–3.40 (m, 4H), 2.76 (s, 1.5H), 2.76 (s, 1.5H), 1.26–1.22 (m, 6H);

MS (ESI) 510 (M+H), 527 (M+NH$_4$), 508 (M−H);

Anal. Calcd for: C$_{22}$H$_{24}$N$_3$O$_7$SCl C, 51.81; H, 4.74; N, 8.23. Found: C, 51.61; H, 4.90; N, 7.96.

EXAMPLE 88

N-(1-(((4-butyl(1,1'-biphenyl)-4-yl)sulfonyl)methyl)-2-(3,4,4-trimethyl-2,5-dioxo-1-imidazolidinyl)ethyl)-N-hydroxyformamide The desired product was prepared following the procedures described in Example 46A, 46B, 46C and 46D, substituting Example 16B for 23A in Example 46A and 4-nbutylbenzeneboronic acid for 4butyloxybenzeneboronic acid in Example 46B.

$^1$H NMR (d6-DMSO) δ 9.70 (s, 0.5H), 9.54 (s, 0.5H), 8.10 (s, 0.5H), 7.94 (d, 4H, J=1.0 Hz), 7.73 (s, 0.5H), 7.69 (dd, 2H, J=8.1, 2.0 Hz), 7.35 (d, 2H, J=8.4 Hz), 4.96–4.86 (m, 0.5H), 4.60–4.48 (m, 0.5H), 3.77–3.42 (m, 4H), 2.75 (s, 3H), 2.64 (t, 2H, J=7.4 Hz), 1.64–1.54 (m, 2H), 1.40–1.27 (m, 2H), 1.24 (s, 3H), 1.22 (s, 3H), 0.91 (t, 3H, J=7.5 Hz);

MS (ESI) 516 (M+H), 533 (M+NH$_{14}$), 538 (M+Cl), 514 (M−H);

Anal. Calcd for: C$_{26}$H$_{33}$N$_3$O$_6$S C, 60.56; H, 6.45; N, 8.14. Found: C, 60.32; H, 6.44; N, 8.09.

EXAMPLE 89

N-(1-(((4'-butyl(1,1'-biphenyl)-4-yl)oxy)methyl)-2-(4,4-dimethy-2,5-dioxo-1-imidazolidinyl)ethyl)-N-hydroxyformamide The desired product was prepared according to the procedures of Example 23B substituting 4-(4'-butylphenyl)-phenol for 4-(4'-ethoxyphenyl)-phenol.

1H NMR (DMSO-δ6) δ 0.93 (t, 3H, J=8 Hz), 1.28 (s, 6H), 1.30–1.39 (m, 2H), 1.50–1.65 (m, 2H), 2.60 (t, 2H, J=7 Hz), 3.51–3.64 (m, 1H), 3.67–3.80 (m, 1H), 4.03–4.24 (m, 2H), 4.35–4.48 (m, 0.5H), 4.78–4.92 (m, 0.5H), 6.99 (dd, 2H, J=3,9 Hz), 7.25 (d, 2H, J=9 Hz), 7.53 (d, 2H, J=9 Hz), 7.58 (d, 2H, J=9 Hz), 7.94 (s, 0.5H), 8.34 (d, 1H, J=6 Hz), 8.39 (s, 0.5H), 9.55 (s, 0.5H), 9.87 (s, 0.5H);

MS (ESI–) 452 (M–H);

Anal. Calcd for: $C_{25}H_{31}N_3O_5$ C, 66.20; H, 6.88; N, 9.26. Found: C, 65.99; H, 6.71; N, 9.19.

EXAMPLE 90

N-(1-(((3'-(cyanomethyl)(1,1'-biphenyl)-4-yl)oxy)methyl)-2-(4,4-dimethy-2,5-dioxo-1-imidazolidinyl)ethyl)-N-hydroxyformamide The desired product was prepared according to the procedures of Example 23B, substituting 4-(3'-cyanomethylphenyl)-phenol for 4-(4'-ethoxyphenyl)-phenol.

1H NMR (DMSO-δ6) δ 2.80 (s, 6H), 3.52–3.83 (m, 2H), 4.10 (s, 2H), 4.124.25 (m, 2H), 4.38 (4.46, mH, J=0.5 Hz), 4.80–4.90 (m, 0.5H), 7.03 (dd, 2H, J=3,9 Hz), 7.30 (d, 1H, J=10 Hz), 7.48 (t, 1H, J=10 Hz), 7.57–7.66 (m, 4H), 7.93 (s, 0.5H), 8.34 (d, 1H, J=6 Hz), 8.39 (s, 0.5H), 9.55 (s, 0.5H), 9.88 (s, 0.5H);

MS (ESI–) 435 (M–H);

Anal. Calcd for: $C_{23}H_{24}N_4O_5 \cdot 0.25CH_3CO_2C_2H_5$ C, 62.87; H, 5.71; N, 12.21. Found: C, 62.85; H, 5.80; N, 12.16.

EXAMPLE 91

N-(1-(4-(2-thienyl)phenoxy)methyl)-2-(1-(3,4,4-trimethyl-2,5-dioxo-1-imidazolidinyl)ethyl)-N-hydroxyformamide The desired product was prepared following the procedures of Examples 16C and 16E, substituting 4-(4'-(2-thienyl)phenyl)phenol for 4-bromophenol in Example 16C.

1H NMR (DMSO-δ6) δ 1.29 (s, 6H), 2.80 (s, 3H), 3.54–3.66 (m, 1H), 3.69–3.84 (m, 1H), 4.04–4.22 (m, 2H), 4.33–4.47 (m, 0.5H), 4.77–4.90 (m, 0.5H), 6.96 (dd, 2H, J=3,9 Hz), 7.08–7.13 (m, 1H), 7.38 (d, 1H, J=3 Hz), 7.46 (d, 1H, J=4 Hz), 7.59 (d, 2H, J=9 Hz), 7.92 (s, 0.5H), 8.31 (s, 0.5H), 9.54 (s, 0.5H), 9.86 (s, 0.5H). MS (ESI–) 416 (M–H);

Anal. Calcd for: $C_{20}H_{23}N_3O_5S \cdot 0.25H_2O$ C, 56.92; H1 5.61; N, 9.95. Found: C, 56.65; H, 5.48; N, 9.77.

EXAMPLE 92

N-(1-(((3-nitro(1,1'-biphenyl)-4-yl)oxy)methyl)-2-(3,4,4-trimethyl-2,5-dioxo-1-imidazolidinyl)ethyl)-N-hydroxyformamide The desired product was prepared following the procedures of Examples 16C and 16E, substituting 4-phenyl-2-nitrophenol for 4-bromophenol in Example 16C.

1H NMR (DMSO-δ6) δ 1.28 (s, 6H), 2.80 (s, 3H), 3.54–3.65 (m, 1H), 3.70–3.88 (m, 1H), 4.22–4.39 (m, 2H), 4.40–4.50 (m, 0.5H), 4.80–4.91 (m, 0.5H), 7.34–7.41 (m, 2H), 7.43–7.52 (m, 2H), 7.71 (d, 2H, J=8 Hz), 7.87 (s, 0.5H), 8.0 (d, 1H, J=9 Hz), 8.16 (dd, 1H, J=3,6 Hz), 8.29 (s, 0.5H), 9.55 (s, 0.5H), 9.80 (s, 0.5H);

MS (ESI–) 455 (M–H);

Anal. Calcd for: $C_{22}H_{24}N_4O_7$ C, 57.88; H, 5.29; N, 12.27. Found: C, 57.62; H, 5.44; N, 11.95.

EXAMPLE 93

N-(1-(((4'-methyl(1,1'-biphenyl)-4-yl)oxy)methyl)-2-((3-(methylsulfonyl)amino)phenyl)ethyl)-N-hydroxyformamide

EXAMPLE 93A 3-(methylsulfonyl)amino-1-bromo-benzene

The m-bromo aniline was dissolved in 40 mL of pyridine and cooled to 0° C. followed by addition of methansulfonyl chloride dropwise via syringe. After 10 minutes, the solution was warmed to room temperature and stirred for 4 hours. Upon concentration the residue was partitioned between 350 mL of $H_2O$ and 500 mL of dichloromethane in a separatory funnel. The organics were separated and washed with 100 mL of 3N HCl, 200 mL of sat'd $NaHCO_3$ and dried over $MgSO_4$. Upon filtration and concentration in vacuo an off-white solid was obtained. This product was recrystallized from dichloromethane/hexanes to afford 6.7 g (90%) of the desired product as white needles.

EXAMPLE 93B 3-(methylsulfonyl)amino-1-(prop-2-enyl)-benzene

Using a glass sealed vessel the sulfonamide 93A (3.0 g, 12.1 mmol) was suspended in 10 mL of toluene followed by addition of the allyltributyl tin reagent and bubbled with argon for 5 min. To the above suspension was added 280 mg (2 mol %) of $Pd(PPh_3)_4$ and the vessel sealed and heated at 120° C. for 17 hours. After 15 minutes a homogeneous solution was obtained which turned dark brown after 30 minutes. After cooling, the catalyst was filtered off washing with dichloromethane/MeOH. Concentration of the filtrate followed by purification on silica gel eluting with 10% ethyl acetate/hexanes then 20% ethyl acetate/hexanes afforded the desired product, 0.99 g (38%) as a colorless oil which solidified upon standing.

EXAMPLE 93C

N-(1-(((4'-methyl(1,1'-biphenyl)-4-yl)oxy)methyl)-2-((3-(methylsulfonyl)amino)phenyl)ethyl)-N-hydroxyformamide The desired product was prepared from Example 93B, first by epoxidizing as desribed in Example 5C, then opening the epoxide with 4'-hydroxy-4-biphenylcarbonitrile as in Example 5F, then following the sequence of reactions described in Examples 2C through 2F.

1H NMR (DMSO-66) δ 2.32 (s, 3H), 2.88 (d, 2H, J=6 Hz), 2.96 (s, 1H), 2.98 (s, 3H), 4.03–4.11 (m, 1H), 4.15–4.27 (m, 1,5H), 4.72–4.82 (bs, 0.5H), 6.97–7.10 (m, 4H), 7.05 (s, 1H), 7.20–7.30 (m, 3H), 7.50 (d, 2H, J=9 Hz), 7.57 (d, 2H, J=9 Hz), 7.73 (s, 0.5H), 8.25 (s, 0.5H), 9.18 (s, 0.5H), 10.01 (s, 0.5H);

MS (ESI–) 453 (M–H);

Anal. Calcd for: $C_{24}H_{26}N_2O_5S$ C, 63.4 1; H, 5.76; N, 6.16. Found: C, 63.16; H, 6.12; N, 5.76.

EXAMPLE 94

N-(1-(((3-(diethylamino)carbonyl)phenyl)methy)-2-((4'-methyl(1,1'-biphenyl)-4-yl)oxy)ethyl)-N-hydroxyformamide

EXAMPLE 94A 3-bromo-1-(N,N-diethylcarboxamide)-benzene

Diethylamine (10.0 mL, 97 mmol) was dissolved in 60 mL of dry ethyl ether and cooled to 0° C. Benzoyl chloride (3.67 mL, 28 mmol) was dissolved in 10 mL of dry ethyl ether and was slowly added dropwise via syringe to to the above solution. A white slurry developed upon addition and stirring was continued for 10 minutes at 0° C. then warmed to room temperature for 1 hour. The mixture was poured into a separatory funnel containing 500 mL of ethyl ether and 75 mL of 10% NaOH. The organics were separated and washed a second time with 75 mL of 10% NaOH followed by 75 mL of 10% HCl then 200 mL of water. A final wash with 100 mL of brine followed by drying over $MgSO_4$, filtering and then concentration, afforded the 94A as a colorless liquid, 5.9 g (83%) which was used without further purification.

EXAMPLE 94B

N-(1-(((3-(diethylamino)carbonyl)phenyl)methyl)-2-((4'-methyl(1,1'-biphenyl)-4-yl)oxy)ethyl)-N-hydroxyformamide The desired product was prepared following the procedure described in Examples 93B and 93C, substituting Example 94A for Example 93A.

1H NMR (DMSO-δ6) δ 0.98–1.20 (bd, 6H), 2.32 (s, 3H), 2.93 (d, 2H, J=6 Hz), 3.11–3.48 (bd, 4H), 4.04.13 (m, 1H), 4.16–4.30 (m, 1.5H), 4.74–4.86 (bs, 0.5H), 6.98 (d, 2H, J=9 Hz), 7.13–7.40 (m, 6H), 7.50 (d, 2H, J=8 Hz), 7.56 (d, 2H, J=9 Hz), 7.73 (s, 0.5H), 8.23 (s, 0.5H), 9.63 (s, 0.5H), 10.02 (s, 0.5H). MS (ESI+) 461 (M+H). Anal. Calcd for: C28H32N2O4.1.5H2O C, 68.97; H, 7.23; N, 5.74. Found: C, 68.96; H, 7.09; N, 5.42.

EXAMPLE 95

N-(1-(((4'-cyano(1,1'-biphenyl)-4-yl)oxy)methyl)-2-((4'-cyano (1,1'-biphenyl)-4-yl)oxy)ethyl)-N-hydroxyformamide The desired product was prepared using the procedures of Examples 5F,5G and 5H, substituting Example 3B for Example 5E.

1H NMR (DMSO-δ6) δ 4.18–4.36 (m, 4H), 4.43–4.57 (bs, 0.5H), 4.97–5.03 (bs, 0.5H), 7.10 (d, 4H, J=9 Hz), 7.77 (d, 4H, J=9 Hz), 7.81–7.95 (m, 8H), 8.13 (s, 0.5H), 8.42 (s, 0.5H), 9.75 (s, 0.5H), 10.15 (s, 0.5H);

MS (DCI/NH$_3$) M+H (490), M+18 (507);

Anal. Calcd for: $C_{30}H_{23}N_3O_4.0.25H_2O$ C, 72.93; H, 4.79; N, 8.50. Found: C, 72.80; H, 4.74; N, 8.26.

EXAMPLE 96

N-(1-(((4'-cyano(1,1'-biphenyl)-4-yl)oxy)methyl)-2-(4,4-dimethy-2,5-dioxo-1-imidazolidinyl)ethyl)-N-hydroxyformamide The desired product was prepared according to the procedures of Example 23B, substituting 4-(4'-cyanophenyl)-phenol for 4-(4'-ethoxyphenyl)-phenol.

1H NMR (DMSO-δ6) δ 1.27 (s, 6H), 3.50–3.66 (m, 1H), 3.67–3.82 (m, 1H), 4.08–4.28 (m, 2H), 4.38–4.50 (m, 0.5H), 4.80–4.93 (m, 0.5H), 7.06 (dd, 2H, J=3,9 Hz), 7.73 (d, 2H, J=9 Hz), 7.82–7.93 (m, 4H), 7.94 (s, 0.5H), 8.35 (d, 1H, J=6 Hz), 8.40 (s, 0.5H), 9.56 (s, 0.5H), 9.87 (s, 0.5H);

MS (ESI-) 421 (M-H);

Anal. Calcd for: $C_{22}H_{22}N_4O_5.0.25H_2O$ C, 61.89; H, 5.31; N, 13.12. Found: C, 61.82; H, 5.34; N, 12.82.

EXAMPLE 97

N-(1-((4,4-dimethyl-2,5-dioxo-1-imidazolidinyl)methyl)-2-((4'-(2-methoxyethoxy)(1,1'-biphenyl)-4-yl)oxy)ethyl)-N-hydroxyformamide The desired product was prepared according to the procedures of Example 23B, substituting 4-(4'-(2-methoxyethoxy)-phenyl)-phenol for 4-(4'-ethoxyphenyl)-phenol.

1H NMR (DMSO-δ46) δ 1.26 (s, 6H), 3.33 (s, 3H), 3.50–3.64 (m, 1H), 3.66–3.69 (m, 2H), 3.70–3.81 (m, 1H), 4.03–4.22 (m, 4H), 4.35–4.48 (m, 0.5H), 4.78–4.90 (m, 0.5H), 6.98 (dd, 4H, J=3,9 Hz), 7.55 (dd, 4H, J=3,6 Hz), 7.91 (s, 0.5H), 8.33 (d, 1H, J=7 Hz), 8.40 (s, 0.5H), 9.55 (s, 0.5H), 9.86 (s, 0.5H);

MS (ESI-) 470 (M-1);

Anal. Calcd for: $C_{24}H_{29}N_3O_7$ C, 61.13; H, 6.19; N, 8.91. Found: C, 60.86; H, 6.41; N, 8.65.

EXAMPLE 98

N-(1-((4,4-dimethy-2,5-dioxo-1-imidazolidinyl)methyl)-2-((4'-propoxy(1,1'-biphenyl)-4-yl)oxy)ethyl)-N-hydroxyformamide The desired product was prepared according to the procedures of Example 23B, substituting 4-(4'-propyloxyphenyl)-phenol for 4-(4'-ethoxyphenyl)-phenol.

mp. 158–160° C.

Mass Spec. (ESI): +456 (m+H),+473 (m+18), -454 (m-H), -490 (m+35)

$^1$H NMR (DMSO-d6): δ 0.90 (3H, t, J=6 Hz), 1.17 (2.4H, s), 1.20 (3.6H, s), 1.65 (2H, sextuplet, J=6 Hz), 3.46–3.55 (1H, m), 3.59–3.74 (1H, m), 3.86 (2H, t, J=6 Hz), 3.96–4.06 (11H, m), 4.06–4.14 (1H, m), 4.28–4.38 (0.6H, m), 4.72–4.81 (0.4H, m), 6.88 (4H, d, J=4.8 Hz), 7.42, (2H, d, J=4.8 Hz), 7.44 (2H, d, J=4.8 Hz), 7.83 (0.4H, s), 8.24 (1H, s), 8.28 (0.6H, s), 9.43 (0.6H, s), 9.74 (0.4H, s);

$^{13}$C NMR (DMSO-d6): δ 10.4, 22.0, 24.4, 24.5, 36.0, 36.4, 52.1, 56.1, 57.8, 57.9, 64.7, 65.0, 69.0, 114.8, 115.0, 127.2, 132.0, 132.8, 132.9, 155.0, 155.2, 157.0, 157.1, 157.9, 158.2, 163.1, 177.2, 177.3;

Calc. for $C_{24}H_{29}N_3O_6$: C, 63.28; H. 6.42; N, 9.22. Found: C, 63.25; H, 6.48; N, 9.29.

EXAMPLE 99

N-(1-((4,4-dimethy-2,5-dioxo-1-imidazolidinyl)methyl)-2-((4'-pentyloxy(1,1'-biphenyl)-4-yl)oxy)ethyl)-N-hydroxyformamide The desired product was prepared according to the procedures of Example 23B, substituting4-(4'-pentylyloxyphenyl)-phenol for 4-(4'-ethoxyphenyl)-phenol.

1H NMR (300 MHz, DMSO-δ6) δ 0.90 (t, 3H, J=6.9 Hz), 1.27 (s, 6H), 1.3–1.5 (m, 4H), 1.7–1.8 (m, 2H), 3.5–3.8 (m, 2H), 3.98 (t, 2H, J=6.9 Hz), 4.0–4.2 (m, 2H), 4.35–4.45 (m, 0.5H), 4.8–4.9 (m, 0.5H), 6.9–7.0 (m, 4H), 7.5–7.6 (m, 4H), 7.92 (s, 0.5H), 8.3–8.4 (m, 1.5H), 9.53 (s, 0.5H), 9.84 (s, 0.5H);

MS (ESI) 484 (M+H), 501 (M+NH$_4$);

Anal. calcd for $C_{26}H_{33}N_3O_6$: C, 64.57; H, 6.87; N, 8.68. Found: C, 64.27; H, 6.85; N, 8.60.

EXAMPLE 100

N-(1-(((3'-(cyanomethyl)(1'-biphenyl)-yl)sulfonyl)methyl)-3-(4,4-dimethy-2,5-dioxo-1-imidazolidinyl)propyl)-N-hydroxyformamide The desired product was made according to the procedures of Example 61, substituting Example 23A for Example 16B and 4'-thiol-3-cyanomethyl biphenyl for 4'-thiol-4-biphenylcarbonitrile in Example 61A.

$^1$H NMR (300 MHz, d$_6$-DMSO) δ 9.98 (br, 0.5H), 9.63 (br, 0.5H), 8.31 (s, 0.5H), 8.23 (s, 0.5H), 8.12 (s, 0.5H), 7.99–7.92 (m, 4H), 7.82 (s, 0.5H), 7.74 (m, 2H), 7.57 (t, 1H), 7.46 (d, 111), 4.52 (m, 0.5H), 4.14 (s, 2H), 4.00 (m, 0.5H), 3.69–3.57 (m, 2H), 3 42–3.28 (m, 2H), 2.02–1.88 (m, 1H), 1.78–1.64 (m, 1H), 1.21 (s, 6H);

MS (ESI) m/e 499 (M+H)$^+$;

Anal. calcd for $C_{24}H_{26}N_4O_6S$: C, 57.82; H, 5.26; N, 11.24. Found: C, 57.56; H, 5.41; N, 10.89.

EXAMPLE 101

N-(1-(((4'-(trifluoromethoxy)(1,1'-biphenyl)-4-yl)sulfonyl)methyl)-2-(3,4,4-trimethy-2,5-dioxo-1-imidazolidinyl)ethyl)-N-hydroxyformamide The desired product was prepared following the procedures of Example 46, substituting Example 16B for 23A in Example 46A and 4-trifluoromethoxybenzeneboronic acid for 4-butoxybenzeneboronic acid in Example 46B.

$^1$H NMR (300 MHz, d$_6$-DMSO) δ 9.72 (br, 0.5H), 9.56 (br, 0.5H), 8.10 (s, 0.5H), 7.99 (m, 4H), 7.94–7.88 (m, 2H), 7.74 (s, 0.5H), 7.53 (d, 2H), 4.91 (m, 0.5H), 4.54 (m, 0.5H), 3.75–3.44 (m, 4H), 2.75 (s, 3H), 1.24–1.22 (m, 6H);

MS (ESI) m/e 544 (M+H)$^+$;

Anal. calcd for $C_{23}H_{24}F_3N_3O_7S$: C, 50.83; H, 4.45; N, 7.73. Found: C, 51.17; H, 4.77; N, 7.29.

EXAMPLE 102

N-(1-(((4'-cyano(1,1'-biphenyl-4-yl)sulfonyl)methyl)-2-(3-methy-2,5-dioxo-1-imidazolidinyl)ethyl)-N-hydroxyformamide The desired product was made according to the procedures of Example 61, substituting Example 26A for Example 16B in Example 61A.

$^1$H NMR (300 MHz, d$_6$-DMSO) δ 9.83 (s, 0.5H), 9.58 (s, 0.5H), 8.09 (s, 0.5H), 8.04–8.00 (m, 8H), 7.80 (s, 0.5H), 4.94–4.85 (m, 0.5H), 4.52–4.43 (m, 0.5H), 3.91–3.88 (m, 2H), 3.78–3.44 (m, 4H), 2.80 (s, 1.51), 2.79 (s, 1.5H);

MS (ESI) m/e 457 (M+H)$^+$;

Anal. calcd for $C_{21}H_{20}N_4O_6S$: C, 55.26; H, 4.42; N, 12.27. Found: C, 54.99; H, 4.38; N, 12.07.

EXAMPLE 103

N-(1-(((3'-(cyanomethyl)(1,1'-biphenyl)-4-yl)sulfonyl)methyl)-2-(3,4,4-trimethyl-2,5-dioxo-1-imidazolidinyl)ethyl)-N-hydroxyformamide The desired product was prepared following the procedures of Example 46, substituting Example 16B for 23A in Example 46A and 3-cyanomethylbenzeneboronic acid for 4-butoxybenzeneboronic acid in Example 46B.

The desired product was made in the usual way from the a-bromoketone and 4-bromothiophenol.

$^1$H NMR (300 MHz, d$_6$-DMSO) δ 9.71 (s, 0.5H), 9.56 (s, 0.5H), 8.10 (s, 0.5H), 8.03–7.94 (m, 4H), 7.75 (m, 2.5H), 7.57 (t, 2H), 7.46 (d, 2H), 4.96–4.88 (m, 0.5H), 4.59–4.49 (m, 0.5H), 4.14 (s, 2H), 3.69–3.48 (m, 4H), 2.75 (s, 3H), 1.24 (s, 3H), 1.22 (s, 3H);

MS (ESI) m/e 499 (M+H)$^+$;

Anal. calcd for $C_{24}H_{26}N_4O_6S$: C, 57.82; H, 5.26; N, 11.24. Found: C, 57.73; H, 5.36; N, 10.95.

EXAMPLE 104

N-(1-(((4'-cyano(1,1'-biphenyl)-4-yl)oxyl)methyl)-2-(1,6-dihydro-3-methyl-6-oxo-1-pyridazinyl)ethyl)-N-hydroxyformamide The desired product was prepared following the procedures of Example 3C and 3D, substituting the potassium salt 6-methyl-3(2H)-pyridazinone (generated in situ with potassium carbonate) for potassium phthalimide in Example 3C.

$^1$H NMR (300 MHz, CD$_3$OD) δ 8.31 (s, 0.5H), 7.91 (s, 0.5H), 7.76 (s, 4H), 7.6–7.64 (d, 2H), 7.38 (dd, 1H), 7.08 (d, 2H), 6.94 (dd, 1H), 5.20–5.11 (m, 0.5H), 4.64–4.52 (m, 2H), 4.42–4.32 (m, 2H), 4.27–4.19 (m 0.5H), 2.35 (s, 1.5H), 2.34 (s, 1.5H);

MS (ESI) m/e 405 (M+H)$^+$;

Anal. calcd for $C_{22}H_{20}N_4O_4$: C, 65.34; H, 4.98; N, 13.85. Found: C, 64.85 H, 5.36; N, 13.44.

EXAMPLE 105

(±)-N-(1-(((4'-cyano(1,1'-biphenyl)-4-yl)sulfonyl)methyl)-2-(4,4-dimethyl-2,5-dioxo-1-imidazolidinl)ethyl)-N-hydroxyformamide:

The desired product was made according to the procedures of Example 61, substituting Example 47A for Example 16B in Example 61A.

$^1$H NMR (300 MHz, d$_6$-DMSO) δ 9.98 (s, 0.5H0, 9.62 (s, 0.5H), 8.31 (s, 0.5H), 8.22 (s, 0.5H), 8.12 (s, 0.5H), 8.05–7.96 (m, 8H), 7.82 (s, 0.5H), 4.55–4.46 (m, 0.5H), 4.07–3.97 (m, 0.5H), 3.70–3.56 (m, 2H), 3.32–3.24 (m, 2H), 2.02–1.88 (m, 0.5H), 1.76–1.64 (m, 0.5H), 1.21–1.18 (m, 6H);

MS (ESI) m/e 485 (M+H)$^+$.

EXAMPLE 106

(±)-N-(1-(((4-(4-fluorophenoxy)phenyl)sulfonyl)methyl)-2-(4,4-dimethyl-2,5-dioxo-1-imidazolidinyl)ethyl)-N-hydroxyformamide The desired product was made according to the procedures of Example 61, substituting Example 26A for Example 16B and 4-(4'-fluorophenoxy)-benzene thiol for 4'thiol-4-biphenyl carbonitrile in Example 61A.

$^1$H NMR (300 MHz, d$_6$-DMSO) δ 9.66 (s, 0.5H), 9.50 (s, 0.5H), 8.39 (s, 0.5H), 8.35 (s, 0.5H), 8.10 (s, 0.5H), 7.88 (dd, 2H), 7.68 (s, 0.5H), 7.36–7.30 (m, 2H), 7.26–7.20 (m, 2H), 7.15 (d, 2H), 4.88–4.80 (m, 0.5H), 4.51–4.41 (m, 0.5H), 3.70–3.39 (m, 4H), 1.24–1.22 (m, 6H);

MS (ESI) m/e 480 (M+H)$^+$;

Anal. calcd for $C_{21}H_{22}FN_3O_7S$: C, 52.60; H, 4.62; N, 8.76. Found: C, 52.79; H, 4.57; N, 8.68.

EXAMPLE 107

N-(1-((4-(4-pyridinyl)phenoxy)methyl)-2-(3,4,4-trimethy-2,5-dioxo-1-imidazolidinyl)ethyl)-N-hydroxyformamide The desired product was prepared following the procedures of Examples 16C and 16E, substituting4-(4-pyridinyl)-phenol for 4-bromophenol in Example 16C.

mp: 217–218° C.

1H NMR (DMSO-d6): δ 9.53–9.97 (c, 1H), 8.55–8.60 (c, 2H), 8.32 (s, ½H), 7.92 (s, ½H), 7.77 (s, 1H), 7.75 (s, 1H), 7.65 (s, 1H), 7.64 (s, 1H), 7.01–7.08 (c, 2H), 4.82–4.89 (c, ½H), 4.39–4.46 (c, ½H), 4.18–4.25 (c, 1H), 4.084.17 (c, 1H), 3.71–3.83 (c, 1H), 3.57–3.66(c, 1H), 2.78(s, 1.5H), 2.77(s, 1.5H), 1.27(s, 3H), 1.26(s, 3H);

MS (ESI(+)) 413 (M+H), 435 (M+Na), 847 (2M+Na);

Anal. Calcd for: $C_{21}H_{24}N_4O_5$·0.5H$_2$O C, 59.84; H. 5.98; N, 13.29. Found: C, 60.18; H, 6.05; N, 13.10.

EXAMPLE 108

(S)-N-(1-((4,4-dimethy-2,5-dioxo-1-imidazolidinyl)methyl)-2-((4'-(trifluoromethoxy)(1,1'-biphenyl)-4-yl)oxy)ethyl)-N-hydroxyformamide

EXAMPLE 108A (R) 1-(4-(4'-(trifluoromethoxyphenyl)phenoxy)-3-benzyloxy-2-propanol A solution of 4-(4'-trifluoromethoxyphenyl)-phenol (1.854 g, 7.3 mmol) and (S)-2-(benzyloxymethyl)-oxirane (1.0 g, 6.1 mmol) in DMF (15 mL) was treated with potassium carbonate (1.007 g, 7.3 mmol), then stirred at 80° C. overnight. The reaction mixture was allowed to cool to 25° C., poured into water (100 mL) and extracted twice with ethyl acetate (200 mL×2). The combined organics were washed with sat. aq. NH$_4$Cl, water, brine, dried (Na$_2$SO$_4$), filtered, and concentrated. Purification by flash silica gel column chromatography eluting with 20 to 25% ethyl acetate: hexane afforded 2.03 g (80% yield) of the desired product as a white solid.

EXAMPLE 108B

A solution of Example 108A (1.505 g, 3.6 mmol), di-Boc hydroxylamine (1.007 g, 4.3 mmol), and triphenyl phosphine (1.23 g, 4.7 mmol) in THF (15 mL) was treated with diethylazodicarboxylate (0.735 mL, 4.7 mmol) at room temperature, stirred for 1 hour, then concentrated. The crude was purified by column chromatography eluting with 10% ethyl acetate:hexane to give 1.16 g (50%)of 108B.

EXAMPLE 108C

A solution of Example 108B (248 mg, 0.4 mmol) in THF (3mL) was hydrogenated (H$_2$ balloon) overnight in the presence of 23 mg of 10% Pd on carbon. The reaction mixture was filtered, concentrated and purified by silca gel column chromatography eluting with 25% ethyl acetate: hexane to afford 180 mg (85%)of the desired product.

EXAMPLE 108D

A solution of Example 108C (228 mg, 0.42 mmol), 5,5-dimethyl hydantoin (94 mg, 0.73 mmol) and triphenyl phospine (165 mg, 0.63 mmol) in THF (4 mL) was treated with diethylazodicarboxylate (0.1 mL, 0.63 mmol) drowise via syringe. The resulting light yellow solution was stirred at 25° C. for 45 minutes, concentrated, and purified by silca gel column chromatography eluting with 25% ethyl acetate:hexane to afford 193 mg (71%)of the desired product.

EXAMPLE 108E (S)-N-(1-((4,4-dimethy-2,5-dioxo-1-imidazolidinyl) methyl)-2-((4'-(trifluoromethoxy)(1,1'-biphenyl)-4-yl)oxy)ethyl)-N-hydroxy Amine A solution of Example 108D (191 mg, 0.29 mmol) in dichloromethane (3 mL) was treated with TFA (1.5 mL) dropwise via syringe. The reaction was stirred at rt for 40 minutes then concentrated and the residue was partitioned between ethyl acetate and NaHCO$_3$. The organic extract was washed with brine, dried (Na$_2$SO$_4$), filtered, and concentrated to afford 113 mg (86%) of the desired product as a white solid.

EXAMPLE 108F (S)-N-(1-((4,4-dimethy-2,5-dioxo-1-imidazolidinyl) methyl)-2-((4'-(trifluoromethoxy)(1,1'-biphenyl)yl) oxy)ethyl)-N-hydroxyformamide The desired product was prepared from 108E following the procedure of Example 2F.

MS (ESI) m/e 482 (M+H)$^+$.

EXAMPLE 109

(R)-N-(1-((4,4-dimethy-2,5-dioxo-1-imidazolidinyl) methyl)-2-((4'-(trifluoromethoxy)(1,1'-biphenyl)-4-yl)oxy)ethyl)-N-hydroxyformamide The desired product was prepared following the procedures of Example 108, substituting (R)-2-(benzyloxymethyl)-oxirane for (S)-2-(benzyloxymethyl)-oxirane.

$^1$H NMR (300 MHz, d$_6$-DMSO) δ 9.86 (s, 0.5H), 9.55 (s, 0.5H), 8.39 (s, 0.5H), 8.35 (s, 0.5H), 8.33 (s, 0.5H), 7.93 (s, 0.5H), 7.76–7.73 (m, 2H), 7.64 (d, 2H), 7.42 (d, 2H), 7.02 (dd, 2H), 4.91–4.80 (m, 0.5H), 4.474.38 (m, 0.5H), 4.23–4.06 (m, 2H), 3.79–3.50 (m, 2H), 1.27 (s, 1.5H), 1.26 (s, 1.5H);

MS (ESI) m/e 482 (M+H)$^+$.

EXAMPLE 110

N-(1-(((4'-(trifluoromethoxy)(1,1'-biphenyl)-4-yl) oxy)methyl)-3-(4,4-dimethyl-2,5-dioxo-1-imidazolidinyl)propyl)-N-hydroxyformamide The desired product was prepared according to the procedures of Example 5, omitting the methylation step in Example SB and substituting 4-(4'-trifluoromethoxyphenyl) phenol for 4'-hydroxy-4-biphenylcarbonitrile in Example 5F.

mp: 197.1–197.9° C.;

$^1$H NMR (300 MHz, DMSO-δ6) δ; 1.27 (s, 6H), 1.70–2.00 (m, 2H), 3.35–3.46 (2H), 3.97–4.16 (m, 2.75H), 4.51 (br s, 0.25H), 7.00–7.03 (d, 2H, J=9 Hz), 7.39–7.42 (d, 2H, J=9 Hz), 7.60–7.63 (d, 2H, J=9 Hz), 7.72–7.75 (d, 2H, J=9 Hz), 8.25–8.35 (2H), 9.55 (s, 0.75H), 9.95 (br s, 0.25H);

MS (ESI) m/e 496 (M+H)$^+$, 518 (m+Na)+, 494 (m–H)$^-$, 530 (m+Cl)–;

Anal. calcd for CH$_{23}$H$_{24}$F$_3$N$_3$O$_6$: C, 55.75; H, 4.88; N, 8.48. Found: C, 55.72; H, 5.07; N, 8.59.

EXAMPLE 111

N-(1-(4-((4-pyridinylthio phenoxy)methyl)-2-(4,4-dimethyl-2,5-dioxo-1-imidazolidinyl)ethyl)-N-hydroxyformamide The desired product was prepared following the procedures of Example 23B, substituting the compound prepared by the addition of 4-hydroxythiophenol to 4-chloropyridine for 4-(4'-butyloxyphenyl)-phenol.

$^1$H NMR (300 MHz, DMSO-δ6) δ; 1.258–1.272 (6H), 3.492–3.793 (m, 2H), 4.082–4.248 (m, 2H), 4.437 (m, 0.5H), 3.861 (m, 0.5H), 5.759 (s, 1H), 6.927–6.948 (dd, 2H, J=1.5, 4.8 Hz), 7.063–7.102 (dd, 2H, J=3, 8.7 Hz), 7.529–7.557 (d, 2H, J=8.4 Hz), 7.939 (s, 0.5H), 8.323–8.343 (dd, 2H, J=1.2, 4.8 Hz), 8.391 (s, 0.5H), 9.555 (s, 0.5H), 9.866 (s, 0.5H); MS (ESI) m/e 431 (M+H)$^+$, 453 (m+Na)+, 429 (m–H)–, 465 (m+Cl)–.

EXAMPLE 112

N-(1-((((4-chlorophenoxy)phenyl)sulfonyl)methy)-3-(4,4-dimethyl-2,5-dioxo-1-imidazolidinyl)propyl)-N-hydroxyformamide The desired product was prepared according to the procedures of Example 61, substituting 4-(4'-chlorophenoxy) benzene thiol for 4'-thiol-4-biphenylcarbonitrile and Example 47A for Example 16B in Example 61A.

$^1$H NMR (d6-DMSO) δ 9.94 (s, 0.5H), 9.58 (s, 0.5H), 8.23 (d, 0.5H, J=9.5 Hz), 8.11 (s, 0.5H), 8.05 (d, 0.5H, J=9.2 Hz), 7.89–7.83 (m, 2H), 7.76 (s, 0.5H), 7.54–7.50 (m, 2H), 7.22–7.16 (m, 4H), 4.52–4.41 (m, 0.5H), 4.10–3.92 (m, 0.511), 3.66–3.37 (m, 2H), 3.31–3.24 (m, 3H), 1.96–1.84 (m, 1H), 1.74–1.62 (m, 1H), 1.28–1.21 (m, 6H);

MS (ESI) 508 (M–H), 510 (M+H), 532 (M+Na).

EXAMPLE 113

N-(1-((4'-cyano(1,1"-biphenyl)-4-yl)oxyl)methyl)-2-(1,6-dihydro-6-oxo-1-pyridazinyl)ethyl)-N-hydroxyformamide The desired product was prepared following the procedures of Example 104, substituting pyridazinone for 6-methyl-3(2H)-pyridazinone.

¹H NMR (d6-DMSO) δ 9.99 (s, 0.5H), 9.64 (s, 0.5H), 8.28 (s, 0.5H), 7.96–7.83 (m, 5.5H), 7.75–7.71 (m, 2.0H), 7.47–7.41 (m, 1H), 7.07–6.95 (m, 3H), 5.11–5.00 (m, 0.5H), 4.62–4.12 (m, 4.5H);

MS (ESI) 391 (M+H), 413 (M+Na), 389 (M−H);

Anal. Calcd for: $C_{21}H_{18}N_4O_4 \cdot 0.5H_2O$ C, 63.15; H, 4.79; N. 14.02. Found: C, 63.33; H, 4.66; N, 13.68.

EXAMPLE 114

N-(1-(((4'-(aminosulfonyl)(1,1'-biphenyl)-4-yl)oxy)methyl)-2-(3,4,4-trimethyl-2,5-dioxo-1-imidazolidinyl)ethyl)-N-hydroxyformamide The desired product was prepared following the procedures of Examples 16C and 16E, substituting 4-(4'-sulfonamidephenyl)-phenol for 4-bromophenol.

mp 203–205° C.;

1H NMR (DMSO-d6): d 9.88 (bs, 112H), 9.54 (bs, ½H), 8.32 (s, ½H), 7.56–8.01 (c, 5 ½H), 7.34 (s, 1H), 7.00–7.14 (c, 4H), 4.78–4.97 (c, ½H), 4.34–4.50 (c, ½H), 4.0–4.27 (c, 2H), 3.69–3.85 (c, 1H), 3.57–3.68 (c, 1H), 2.78 (s, 3H), 1.17–1.28 (c, 6H);

13C NMR (DMSO-d6): δ 176.5, 176.2, 163.1, 158.1, 154.2, 154.1, 128.3, 128.2, 128.0, 127.0, 126.8, 126.2, 115.2, 64.8, 60.7, 36.7, 36.4, 24.2, 21.4;

MS (ESI(+)) 491 (M+H), 508 (M+NH), 513 (M+Na).

EXAMPLE 115

N-(1-(((4'-(trifluoromethoxy)(1,1'-biphenyl)-4-yl)sulfonyl)methyl)-2-(4,4-dimethyl-2,5-dioxo-1-imidazolidinyl)ethyl)-N-hydroxyformamide The desired product was prepared following the procedures of Example 46, substituting 4-trifluoromethoxybenzeneboronic acid for 4-butyloxybenzeneboronic in Example 46B.

mp 195–197° C.;

1H NMR, (DMSO-d6): δ 9.62 (bs, 1H), 8.29–8.43 (c, 1H), 8.10 (s, ½H), 7.95–8.05 (c, 4H), 7.92 (d, 1H, J=3 Hz), 7.88 (d, 1H, J=3 Hz), 7.74 (s, ½H), 7.54 (s, 1H), 7.49 (s, 1H), 4.87–4.99 (c, ½H), 4.50–4.63 (c, ½H), 3.43–3.80 (c, 4H), 1.22 (s, 6H);

13C NMR (DMSO-d6): δ 177.2, 177.1, 162.3, 157.1, 155.0, 154.8, 148.7, 144.0, 143.9, 138.0, 137.8, 137.5, 129.2, 128.6, 128.4, 127.9, 127.7, 121.5, 118.4, 57.8, 53.3, 53.0, 51.3, 47.5, 38.8, 38.1, 24.31, 24.30;

MS (ESI(+)) 530 (M+H), 547 (M+NH₄), 552 (M+Na), 1076 (2M+NH), 1081 (2M+Na);

HRMS: Calcd: 530.120. Found: 530.1193;

Anal. Calcd for: $C_{22}H_2F_3N_3,_7S$ C, 49.90; H, 4.19; N, 7.94; F, 10.76; S,6.06. Found: C, 49.58; H, 4.10; N, 7.75; F, 11.04; S, 5.96.

EXAMPLE 116

N-(1-(4-((4-pyridinyloxy)phenyl)sulfonyl))ethyl)-N-hydroxyformamide

EXAMPLE 116A 4-(4-(methylsulfonyl)phenoxy)pyridine

A mixture of 4-methylsulfonylphenol (2.93 g, 17 mmol) and 4-chloropyridine hydrochloride (2.93 g, 19.5 mmol) was heated at 150° C., resulting in a gradual melt, which was stirred at 150° C. for 4 hours, then partitioned between ethyl acetate and 1N NaOH. The organic extract was dried over MgSO₄, filtered, and concentrated to 1.3 g of a yellow solid. The solid was recrystallized from ethyl acetate-ether to give 0.81 g of the desired product as a white solid.

EXAMPLE 116B

N-(1-(4-((4-pyridinyloxy)phenyl)sulfonyl))ethyl)-N-hydroxyformamide

The desired product was prepared following the procedures of Examples 75, substituting Example 116A for Exaple 71B and acetaldehyde for propionaldehyde.

mp 180–181° C.;

1H NMR, 400 MHz (DMSO-d6): δ 9.71 (bs, 1H), 8.54 (d, 2H, J=3 Hz), 8.05 (s, ½H), 7.97 (d, 2H, J=6 Hz), 7.84 (s, ½H), 7.49 (d, 2H, J=6 Hz), 7.03–7.13 (c, 2H), 4.63–4.73 (c, ½H), 4.28–4.39 (c, ½H), 3.59–3.78 (c, 1H),3.48 (dd, 1H, J=3,10.5 Hz), 1.20 (dd, 3H, J=4.5, 10.5 Hz);

13C NMR (DMSO-d6): δ 162.62, 162.61, 161.33, 158.33, 158.31, 156.74, 151.77, 135.40, 135.13, 130.74, 130.45, 120.56, 120.34, 113.27,56.50,49.69, 45.02, 19.05, 17.71;

MS (ESI(+)) 337 (M+H), 359 (M+Na),391 (M+Na+MeOH), 695 (2M+Na);

Anal. Calcd for: $C_{15}H_{16}N_2O_5S \cdot 0.5H_2O$: C, 52.16; H, 4.96; N, 8.11; S, 9.28. Found: C, 52.32; H, 4.78; N, 7.98; S, 9.45.

EXAMPLE 117

N-(1-((((4-cyanophenoxy)phenyl)sulfonyl)methyl)-2-(4,4-dimethyl-2,5-dioxo-1-imidazolidinyl)ethyl)-N-hydroxyformamide The desired product was prepared according to the procedures of Example 61, substituting 4-(4'-cyanophenoxy)benzene thiol for 4-thiol-4-biphenylcarbonitrile and Example 23A for Example 16B, in Example 61A.

¹H NMR (300 MHz, d₆-DMSO) δ 9.70 (s, 0.5H), 9.50 (s, 0.5H), 8.39 (s, 0.5H), 8.34 (s, 0.5H), 8.10 (s, 0.5H), 7.98–7.91 (m, 4H), 7.68 (s, 0.5H), 7.37–7.27 (m, 4H), 4.88–4.77 (m, 0.5H), 4.52–4.41 (m, 0.5H), 3.78–3.39 (m, 4H), 1.24–1.22 (m, 6H);

MS (ESI) m/e 487 (M+H)⁺;

Anal. calcd for $C_{22}H_{22}N_4O_7S$: C, 54.31; H, 4.56. Found: C, 54.17; H, 4.79.

EXAMPLE 118

N-(1-((4-((4-(trifluoromethoxy)phenoxy)phenyl)sulfonyl)methyl)-3-(4,4-dimethyl-2,5-dioxo-1-imidazolidinyl)propyl-N-hydroxyformamide The desired product was prepared according to the procedures of Example 61, substituting 4-(4'-trifluoromethoxyphenoxy)benzene thiol for 4'-thiol-4-biphenylcarbonitrile and Example 47A for Example 16B, in Example 61A.

1H NMR (d6-DMSO) δ 9.96 (s, 0.5H), 9.60 (s, 0.5H), 8.32 (s, 0.5H), 8.23 (s, 0.5H), 8.11 (s, 0.5H), 7.93–7.86 (m, 2H), 7.75 (s, 0.5H), 7.48 (d, 0.5H, J=8.8 Hz), 7.25 (dd, 4H, J=22.8, 8.8 Hz), 4.53–4.42 (m, 0.5H), 4.04–3.93 (m, 0.5H), 3.65–3.46 (m, 2H), 3.34–3.22 (m, 2H), 2.02–1.62 (m, 2H), 1.26 (s, 3H), 1.23 (s, 3H);

MS (ESI) 560 (M+H), 577 (M+NH), 582 (M+Na), 558 (M−H);

Anal. Calcd for: $C_{23}H_{24}N_3O_8SF_3$: C, 49.37; H, 4.32; N, 7.51. Found: C, 49.46; H, 4.23; N, 7.47.

EXAMPLE 119

N-(1-((4-((4-(trifluoromethoxy)phenoxy)phenyl) sulfonyl)methyl)-2-(4,4-dimethyl-2,5-dioxo-1-imidazolidinyl)ethyl)-N-hydroxyformamide The desired product was prepared according to the procedures of Example 61, substituting 4-(4'-trifluoromethoxyphenoxy)benzene thiol for 4'-thiol-4-biphenylcarbonitrile in Example 61A.

1H NMR (d6-DMSO) δ 9.51 (s, 0.5H), 9.70 (s, 0.5H), 8.09 (s, 0.5H), 7.91 (dd, 2H, J=8.9, 3.1 Hz), 7.68 (s, 0.5H), 7.47 (d, 2H, J=9.2 Hz), 7.31–7.21 (m, 4H), 4.90–4.78 (m, 0.5H), 4.51–4.40 (m, 0.5H), 3.74–3.40 (m, 4H), 2.76 (d, 3H, J=1.7 Hz), 1.27–1.22 (m, 6H);

MS (ESI) 558 (M–H), 560 (M+H), 577 (M+NH$_4$), 582 (M+Na);

Anal. Calcd for: $C_{23}H_{24}N_3O_8SF_3$: C, 49.37; H. 4.32; N, 7.51. Found: C, 49.41; H1 4.29; N, 7.36.

EXAMPLE 120

(±)-N-hydroxy-N-(1-methyl-3-((4-phenoxyphenyl) sulfonyl)propyl)formamide

EXAMPLE 120A (±)-4-((4-phenoxyphenyl)sulfonyl)-2-butanol

A solution of 4-phenoxyphenyl methyl sulfone (1.0 g, 4.0 mmol) in 40 mL of THF at –78° C. was treated with n-butyllithium (1.6 mL, 2.5 M in hexanes), stirred 15 minutes at –78° C., treated with propylene oxide (257 μL), stirred from –78° C. to 23° C. over 16 hours, quenched with H$_2$O, extracted with ethyl acetate, washed with brine, dried over Na$_2$SO$_4$, filtered, and concentrated. Purification on silica gel with 1:1 hexanes/ethyl acetate provided 1.1 g (100%) of the desired product.

MS (ESI) m/e 307 (M+H)$^+$.

EXAMPLE 120B (±)-1,1-dimethylethyl (((1,1-dimethylethoxy) carbonyl)oxy)(3-((4-phenoxyphenyl)-sulfonyl)-1-methylpropyl)carbamate A solution of 120A (200 mg, 0.65 mmol) in 20 mL of THF at 0° C. was treated with tert-butyl N-(tert-butoxycarbonyloxy)carbamate (168 mg), triphenylphosphine (188 mg), and diethyldiazocarbodiimide (113 μL), stirred at 23° C. for 2 h, and concentrated. Purification on silica gel with 5:1 hexanes/ethyl acetate provided 289 mg (85%) of the desired product.

MS (ESI) 522 (M+H)$^+$.

EXAMPLE 120C (±)-N-hydroxy-1-methyl-3-((4-phenoxyphenyl) sulfonyl)propanamine A solution of Example 120B (1.59 g, 3.05 mmol) in 20 mL of dichloromethane at 0° C. was treated with trfluoroacetic acid (5 mL), stirred at 23° C. for 1 hour, concentrated, dissolved in ethyl acetate, washed with saturated NaHCO$_3$ and brine, dried over Na$_2$SO$_4$, filtered, and concentrated. Purification on silica gel with 5% methanol/dichloromethane provided 820 mg (84%) of the desired product.

MS (ESI) m/e 322 (M+H)$^+$.

EXAMPLE 120D (±)-N-hydroxy-N-(1-methyl-3-((4-phenoxyphenyl) sulfonyl)propyl)formamide A solution of 120C (820 mg, 2.55 mmol) in 50(mL of THF at 0° C. was treated with acetic formic anhydride (200 μL), stirred at 0° C. for 20 min, quenched with saturated NaHCO$_3$, extracted with ethyl acetate, washed with brine, dried over Na$_2$SO$_4$, filtered, and concentrated. Purification on silica gel with 5% methanol/dichloromethane provided 314 mg (35%) of the desired product.

$^1$H NMR (300 MHz, d$_6$-DMSO) δ 9.77 (br, 0.5H), 9.37 (br, 0.5H), 8.22 (s, 0.5H), 7.86 (d, 2.5H, J=8.1 Hz), 7.49 (t, 2H, J=8.1 Hz), 7.29 (t, 1H, J=7.8 Hz), 7.17 (dd, 4H, J=7.4, 1.1 Hz), 4.36–4.23 (m, 0.5H), 3.93–3.80 (m, 0.5H), 3.30–3.06 (m, 2H), 1.90–1.61 (m, 2H), 1.13 (d, 1.5H, J=6.6 Hz), 1.07 (d, 1.5H, J=6.6 Hz);

MS (ESI) m/e 350 (M+H)$^+$;

Anal. calcd for $C_{17}H_{19}NO_5S$: C, 58.43; H, 5.48; N, 4.00. Found: C, 58.65; H, 5.73; N, 3.95.

EXAMPLE 121

(±)-N-hydroxy-N-(1-methyl-3-((4-(4-(trifluoromethoxy)phenoxy)phenyl)-sulfonyl)propyl) formamide The desired product was prepared following the procedure described in Examples 120A, 120B, 120C, and 120D, substituting 4-(4-trifluoromethoxyphenoxy)phenyl methyl sulfone for 4-phenoxyphenyl methyl sulfone in Example 120A.

$^1$H NMR (300 MHz, d$_6$-DMSO) δ 9.76 (br, 0.5H), 9.35 (br, 0.5H), 8.22 (s, 0.5H), 7.89 (d, 2.5H, J=8.8 Hz), 7.48 (d, 2.5H, J=9.2 Hz), 7.29 (d, 2H, J=9.1 Hz), 7.22 (d, 2H, J=8.8 Hz), 4.36–4.24 (m, 0.5H), 3.94–3.80 (m, 0.5H), 3.30–3.07 (m, 2H), 1.90–1.63 (m, 2H), 1.13 (d, 1.5H, J=6.8 Hz), 1.07 (d, 1.5H, J=6.8 Hz);

MS (ESI) m/e 432 (M–H)$^-$.

Anal. calcd for $C_{18}H_{18}F_3NO_6S$: C, 49.88; H. 4.18; N, 3.23. Found: C, 49.99; H1 4.12; N, 3.19.

EXAMPLE 122

(±)-N-(3-((4-(4-fluorophenoxy)phenyl)sulfonyl)-1-methylpropyl)-N-hydroxyformamide The desired product was prepared following the procedure described in Examples 120A, 120B, 120C, and 120D, substituting 4-(4-fluorophenoxy)phenyl methyl sulfone for 4-phenoxyphenyl methyl sulfone in Example 120A.

$^1$H NMR (300 MHz, d$_6$-DMSO) δ 9.77 (br, 0.5H), 9.37 (br, 0.5H), 8.22 (s, 0.5H), 7.87–7.84 (m, 2.5H), 7.36–7.22 (m, 4H), 7.15 (d, 2H), 4.31–4.26 (m, 0.5H), 3.88–3.83 (m, 0.5H), 3.31–3.07 (m, 2H), 1.88–1.65 (m, 2H), 1.13 (d, 1.5H), 1.07 (d, 1.5H);

MS (ESI) m/e 368 (M+H)$^+$;

Anal. calcd for $C_{17}H_{18}FNO_5S$: C, 55.58; H1 4.94; N, 3.81. Found: C, 55.73; H, 5.14; N, 3.76.

EXAMPLE 123

(R)-N-(1-((4,4-dimethyl-2,5-dioxo-1-imidazolidinyl) methyl)-3-((4-phenoxyphenyl)sulfonyl)propyl)-N-hydroxyformamide

EXAMPLE 123A (R)-1,1-dimethylethyl (((1,1-dimethylethoxy) carbonyl)oxy)(3-((4-phenoxyphenyl)-sulfonyl)-1-((phenylmethoxy)methyl)propyl)carbamate The desired product was prepared following the procedures described in Examples 120A and 120B substituting benzyl (S)-(+)-glycidyl ether for propylene oxide.

EXAMPLE 123B (R)-1,1-dimethylethyl((((1,1-dimethylethoxy)
carbonyl)oxy)(3-((4-phenoxyphenyl)-sulfonyl)-1-
(hydroxymethyl)propyl)carbamate A solution of Example 123A (7.5 g) in methanol (75 mL) and acetic acid (7.5 mL) was hydrogenated at 60 psi in the presence of 10% Pd/carbon (0.75 g) for 4 h. The reaction was filtered and concentrated to give 6.07 g (95%) of 123B.
MS (ESI) m/e 538 (M+H)$^+$.

EXAMPLE 123C (R)-1,1-dimethylethyl (((((1,1-dimethylethoxy)
carbonyl)oxy)(1-(4,4-dimethyl-2,5-dioxo-1
imidazolidinyl)methyl)-3-((4-phenoxyphenyl)
sulfonyl)propyl)carbamate A solution of 123B (1 g, 1.86 mmol) in 9 mL of THF at 0° C. was treated with 5,5-dimethylhydantoin (357 mg), triphenylphosphine (731 mg), and diethyldiazocarbodiimide (439 µL), stirred at 23° C. for 5 hours, and concentrated. Purification on silica gel with 2:1 hexanes/ethyl acetate provided 964 mg (80%) of the desired product.
MS (ESI) m/e 646 (M–H)$^-$.

EXAMPLE 123D (R)-N-(1-((4,4-dimethyl-2,5-dioxo-1-imidazolidinyl)
methyl)-3-((4-phenoxyphenyl)-sulfonyl)propyl)-N-
hydroxyformamide Example 123C was converted to the desired product following the procedures of Examples 120C and 120D.
$^1$H NMR (300 MHz, d$_6$-DMSO) δ 9.72 (br, 0.5H), 9.41 (br, 0.5H), 8.36 (s, 0.5H), 8.31 (s, 0.5H), 8.23 (br, 1H), 7.87–7.83 (m, 2H), 7.70 (br, 0.5H), 7.49 (t, 2H), 7.29 (t, 1H), 7.19–7.14 (m, 4H), 4.48–4.37 (m, 0.5H), 4.19–4.15 (m, 0.5H), 3.59–3.22 (m, 4H), 1.91–1.64 (m, 2H), 1.22 (s, 6H);
MS (ESI) m/e 476 (M+H)$^+$;
Anal. calcd for C$_{22}$H$_{25}$O$_7$N$_3$S: C, 55.57; H, 5.30; N, 8.84. Found: C, 55.52; H, 5.33; N, 8.75.

EXAMPLE 124

(R)-N-(1-((2,5-dioxo-3,4,4-trimethyl-1-
imidazolidinyl)methyl)-3-((4-phenoxyphenyl)-
sulfonyl)propyl-N-hydroxyformamide The desired product was prepared as described in Example 123 substituting 1,5,5-trimethylhydantoin for 5,5-dimethylhydantoin in Example 123C.
$^1$H NMR (300 MHz, d$_6$-DMSO) δ 9.73 (br, 0.5H), 9.41 (br, 0.5H), 8.22 (s, 0.5H), 7.87–7.83 (m, 2H), 7.69 (s, 0.5H), 7.49 (t, 2H, J=8.2 Hz), 7.28 (t, 1H, J=7.4 Hz), 7.19–7.14 (m, 4H), 4.49–4.36 (m, 0.5H), 4.19–4.07 (m, 0.5H), 3.63–3.14 (m, 2H), 2.77 (s, 1.5H), 2.76 (s, 1.5H), 1.93–1.60 (m, 2H), 1.24–1.22 (m, 6H1);
MS (ESI) m/e 490 (M+H)$^+$;
Anal. calcd for C$_{23}$H$_{27}$N$_3$O$_7$S: C, 56.43; H, 5.56; N, 8.58. Found: C, 56.52; H, 5.82; N, 8.42.

EXAMPLE 125

N-hydroxy-N-(((2-(4-(4-pyridinyloxy)phenyl)
sulfonyl)methylamino)ethyl)formamide

EXAMPLE 125A

Ethyl 2-(((4(4-pyridinyloxy)phenyl)sulfonyl)
methylamino)acetate

A cloudy solution of sarcosine ethyl ester hydrochloride (3.1 g, 20 mmol) in dichloromethane (150 mL) was treated with triethylamine (6.13 mL, 44 mmol), cooled with an ice bath, then treated with 4-(4'-pyridyloxy)benzene sulfonyl chloride (6.74 g, 22 mmol) (WO 98/50348, p.30) and stirred for 2.5 hours after which time the mixture was partitioned between water and dichloromethane. The organic layer was washed with sat. aq. NaHCO$_3$, brine, dried and concentrated. The residue was suspended in dichloromethane, filtered, and the solid was washed with dichloromethane. The filtrate and washings were concentrated to give 4.57 g (65%) of the desired product. Rf 0.35 (5% MeOH: dichloromethane).

EXAMPLE 125B

N-(2-hydroxyethyl)-N-methyl-4-(4-pyridinyloxy)
benzenesulfonamide

A solution of Example 125A (2.39 g, 6.8 mmol) in THF (20 mL) was added dropwise over 15 minutes to an ice-cold solution of LAH (0.39 g, 10.3 mmol) in THF (5 mL). The resulting suspension was stirred at 0° C. for 10 minutes then at room temperature for 3 hours. The reaction was cooled, quenched with 500 µL H$_2$O followed by addition of 1.5 mL NaOH and 500 µL 10, then stirred at room temperature for 1 hour, poured into water and extracted 3 times with ethyl acetate. The combined organics were dried, filtered, and concentrated to give 1.7 g of the desired product.

EXAMPLE 125C

N-hydroxy-N-(((2-(4-(4-pyridinyloxy)phenyl)
sulfonyl)methylamino)ethyl)formamide Example 125B was converted to the desired product following the procedures of Example 120B, 120C and 120D.
mp: 113–115° C.;
$^1$H NMR (DMSO-d6): δ 10.08 (bs, ½H), 9.70 (bs, ½H), 8.73–8.80 (c, 2H), 8.24 (s, ½H), 7.83–7.94 (c, 2.5H), 7.39 (s, 1H), 7.36 (s, 1H), 7.05–7.16 (c, 2H), 3.66–3.77 (c, 2H), 3.38–3.46 (c, 2H), 2.74 (s, 3H);
MS (ESI(+)) 352 (M+H+), 374 (M+Na+);
Anal. Calcd for: C$_{15}$H$_{17}$N$_3$O$_5$S.0.25EtOAC.0.25H$_2$O: C, 50.85; H, 5.20; N, 11.11; S, 8.48. Found: C,50.96; H, 5.10; N, 11.05; S, 8.68.

EXAMPLE 126

(±)-N-hydroxy-N-(1-(hydroxymethyl)-2-((4-((4-
(trifluoromethoxyphenyl)carbonyl)amino)phenyl)
sulfonyl)ethyl)formamide

EXAMPLE 126A 1-((3-(((1,1-dimethylethyl)dimethylsilyl)oxy)-1-
propenyl)thio)-4-nitrobenzene A solution of a 1.5 to 1 mixture of (E) and (Z) 3-(4-nitrophenylthio)-2-propenol (3.53 g, 16.71 mmol) (JCS, Perkin Trans. I, 1974, 25) in dichloromethane (40 mL) was treated with imidazole (2.28 g, 33.4 mmol) and TBDMSCl (2.77 g, 18.4 mmol), stirred at room temperature for 24 hours, and then partioned between dichloromethane and water. The organic phase was dried, concentrated, and purified on silica gel by flash column chromatography eluting with 8 to 1 hexanes/ethyl acetate to give 5.1 g (94%) of the desired product. Rf: 0.8 (2:1 hexane:ethyl acetate)

EXAMPLE 126B

4((3-(((1,1-dimethylethyl)dimethylsilyl)oxy)-1-
propenyl)thio)benzenamine

A mixture of Example 126A (1.0 g, 3.07 mmol) and NH$_4$Cl (0.164 g, 3.07 mmol) in a 4:1 mixture of ethanol/ water (15 mL) was heated to 60° C. then treated with Fe (1.37 g, 24.5 mmol) portionwise. The suspension was stirred at 70° C. for 1 hour then diluted with ethyl acetate and filtered through a pad of diatomaceous earth (Celite®). The filtrate was washed with brine, dried, and concentrated to give 0.92 g of a yellow oil. Rf: 0.2 (4:1 hexane:ethyl acetate).

EXAMPLE 126C

N-(4-(3-(((1,1-dimethylethyl)dimethylsilyl)oxy)-1-propenyl)thiophenyl)-4-(trifluoromethoxy) benzamide A 0° C. solution of Example 126B (0.92 g, 3.0 mmol) in dichloromethane (10 mL) was sequentially treated with pyridine (0.3 mL, 3.7 mmol) and 4-trifluoromethoxybenzoyl chloride (0.53 mL, 3.4 mmol), stirred at 0° C. for 0.5 hours and then at room temperature for 1 hour. The reaction was diluted with water and extracted with dichloromethane (3×15 mL). The combined extracts were washed with saturated NaHCO$_3$, dried, filtered, concentrated and purified on silica gel by flash column chromatography eluting with 6:1 hexanes/ethyl acetate to give 1.37 g of the desired product. MS (ESI): 501 (M+NH$_4^+$), 506 (M+Na$^+$).

EXAMPLE 126D

N-(4-((3-hydroxy-1-propenyl)sulfonyl)phenyl)-4-(trifluoromethoxy)benzamide

A 0° C. suspension of Example 126C (1.34 g, 2.79 mmol) in a 2:1 mixture of methanol/water (60 mL) was treated with oxone (4.28 g, 6.97 mmol) and NaHCO$_3$ (0.58 g, 6.97 mmol), stirred at 0° C. for 1 hour, and then at room temperature for 18 hours. The suspension was diluted with water then extracted with ethyl acetate (3×30 mL). The combined extracts were washed with water, brine, dried, filtered, concentrated and purified on silica gel by flash column chromatography eluting with 1 to 2 hexanes/ethyl acetate to give 1.2 g of the desired product.

MS (ESI) 402 (M+H$^+$).

EXAMPLE 126E

N-(4-((3-hydroxy-2-(hydroxyamino)propyl)sulfonyl) phenyl)-4-(trifluoromethoxy)benzamide A solution of 126D (0.4 g, 0.99 mmol) in THF (10 mL) was treated with hydroxylamine (0.6 mL, 9.9 mmol, 50% solution), stirred for 3 hours at room temperature, then diluted with water and extracted with ethyl acetate (3×40 mL). The combined extracts were washed with water, brine, dried, filtered, and concentrated. Recrystallization from ethyl acetate gave 0.34 g (77%) of the desired product.

MS (ESI) 435 (M+H$^+$).

EXAMPLE 126F (±)-N-hydroxy-N-(1-(hydroxymethyl-2-((4-((4-(trifluoromethoxyphenyl)carbonyl)-amino)phenyl) sulfonyl)ethyl)formamide A −20° C. solution of Example 126E (0.33 g, 0.77 mmol) in THF (15 mL) was treated dropwise with acetic formic anhydride (0.062 mL, 0.78 mmol) over 25 minutes. The cooling bath was allowed to warm up to 4° C. over 2 hours, after which time the reaction was diluted with water and extracted with ethyl acetate (3×30 mL). The combined extracts were washed with saturated NaHCO$_3$, water, brine, dried, filtered, and concentrated to about 5 mL. Hexane was then added and the resulting precipitate was filtered to give 0.18 g of the desired product. mp. 196° C. (decomp.);

$^1$H NMR (300 MHz, DMSO-d6): δ 10.77 (br. s, 1H), 9.81 (br. s, 0.3H), 9.41 (br. s, 0.7H), 8.15–7.80 (m, 7H), 7.57 (d, J=9.0 Hz, 2H), 4.98 (m, 1H), 4.56 (m, 0.3H), 3.98 (m, 0.7H), 3.60–3.3 (m, 4H);

MS (ESI): 463(M+H), 480(M+NH$_4$), 485(M+Na);

Anal. Calcd. for C$_{18}$H$_{17}$F$_3$N$_2$O$_7$S: C, 46.75; H, 3.70; N, 6.05. Found: C 46.46; H, 3.85; N, 5.96.

EXAMPLE 127

(±)-N-hydroxy-N-(3-hydroxy-2-((4-((phenylcarbonyl)amino)phenyl)sulfonyl)-propyl) formamide

EXAMPLE 127A

N-((4-(1-((((1,1-dimethylethyl)dimethylsilyl)oxy) methyl)ethenyl)thiol)phenyl)benzamide The desired product was prepared according to the procedures of Examples 126A, 126B and 126C, substituting 1-(4-nitrophenylthio)-1-hydroxymethyl-ethene (JCS, Perkin Trans. I, 1974, 25) for 3-(4-nitrophenylthio)-2-propenol in Example 126A and benzoyl chloride for 4-trifluoromethoxybenzoyl chloride in Example 126C. MS (ESI): 400 (M+H$^+$).

EXAMPLE 127B

N-((4-(1-((((1,1-dimethylethyl)dimethylsilyl)oxy) methyl)ethenyl)-sulfonyl)phenyl)benzamide A 0° C. solution of Example 127A (0.1 g, 0.25 mmol) in dichloromethane (3 mL) was treated with m-CPBA (0.18 g, 0.75 mmol, 70%), stirred at room temperature for 1 hour, then diluted with dichloromethane, quenched with 10 mL of 10% aq. NaHSO$_3$ and extracted twice with dichloromethane. The combined organics were washed with satureated NaHCO$_3$, dried, filtered, and concentrated to give 0.11 g of the desired product as a white solid.

MS (ESI) 432 (M+H$^+$).

EXAMPLE 127C (±)-N-(3-(((1,1-dimethylethyl)dimethylsilyl)oxy)-2-((4-((phenylcarbonyl)amino)phenyl)sulfonyl) propyl)-N-hydroxyformamide Example 127B was converted to the desired product following the procedures of Examples 126E and 126F.

MS (ESI): 493 (M+H$^+$), 510 (M+NH$_4^+$).

EXAMPLE 127D (±)-N-hydroxy-N-(3-hydroxy-2-((4-((phenylcarbonyl)amino)phenyl)sulfonyl)-propyl) formamide A solution of Example 127C (0.33 g, 0.6 mmol) in THF (12 mL) was treated with acetic acid (0.037 mL) and tetrabutylammonium fluoride (0.97 mL, 0.97 mmol, 1 M solution on THF), stirred at room temperature for 4 hours, then partitioned between water and ethyl acetate. The organic phase was washed with brine, dried, filtered, and concentrated. The residue was purified via column chromatography eluting with 8 to 10% methanol in dichloromethane to give 35 mg of the desired product.

$^1$H NMR (300 MHz, DMSO-d6): δ 10.70 (s, 1H), 10.16 (br. s, 0.4H), 9.70 (br. s, 0.6H), 8.22 (br. s, 0.4H), 8.06 (d, J=9 Hz, 2H), 7.98 (d, J=7.5 Hz, 2H), 7.88 (m, 2.6H), 7.68–7.52 (m, 3H), 5.08 (t, J=4.5 Hz, 0.6H), 4.95 (br.s, 0.4H), 3.90–3.62 (m, 4H), 3.54 (m, 1H); MS(ESI): m/z 379 (M+H$^+$), 396 (M+NH$_4^+$).

EXAMPLE 128

(±)-N-hydroxy-N-(1-(hydroxymethyl)-2-((4-(((4-pentylphenyl)carbonyl)amino)phenyl)-sulfonyl) ethyl)formamide The desired product was prepared following the procedures of Example 126 substituting 4-n-pentylbenzoyl chloride for 4-trifluoromethoxybenzoyl chloride in Example 126C.

$^1$H NMR (300 MHz, DMSO-d6): δ 10.67 (br. s, 11H), 9.91 (br. s, 0.4H), 9.45 (br. s, 0.6H), 8.15–7.80 (m, 7H), 7.38 (d, J=8.1 Hz, 2H), 5.1 (m, 1H), 4.55 (m, 0.4H), 3.96 (m, 0.6H), 3.60–3.30 (m, 4H), 2.66 (t, J=7.5 Hz, 2H), 1.61 (m, 2H), 1.29 (m, 4H), 0.87 (t, J=6.6 Hz, 3H);

MS(ESI): m/z 449 (M+H$^+$), 466 (M+NH$_4^+$), 471 (M+Na$^+$).

EXAMPLE 129

2,2-dimethyl-3-((4-phenoxyphenyl)sulfonyl)propyl (hydroxy)formamide

EXAMPLE 129A 2,2-dimethyl-3-(tetrahydro-2H-pyran-2-yloxy)propyl methanesulfonate A solution of neopentyl glycol (5.0 g, 48 mmol), pyridine (5 mL) and methanesulfonyl chloride (4.3 mL) in dichloromethane (100 mL) at room temperature was stirred for 7 hours, then partitioned between brine and ethyl acetate. The organic phase was washed sequentially with saturated NaHCO$_3$, brine, dried (Na$_2$SO$_4$), filtered, and concentrated. The concentrate was dissolved in dichloromethane (100 mL), treated with dihydropyran (15.3 mL) and p-toluenesulfonic acid (457 mg),stirred for 1 hour, then treated with saturated NaHCO$_3$ and extracted with ethyl acetate. The combined extracts were washed with brine, dried (NaSO$_4$), filtered, concentrated and purified by flash column chromatography on silica gel with 2:1/hexanes:ethyl acetate to provide the desired product.

MS (ESI) 284 (M+NH$_4$)$^+$.

EXAMPLE 129B 2-(2,2-dimethyl-3-((4-phenoxyphenyl sulfanyl) propoxy)tetrahydro-2H-pyran A solution of 4-phenoxybenzenethiol (4.0 g) in DMSO (30 mL) was treated with sodium hydride (60% oil dispersion, 790 mg) and a solution of Example 129A (4.39 g, 16.5 mmol) in DMSO (30 mL). The resulting mixture was heated to 80° C., stirred for 8 hours, cooled to room temperature, diluted with water, and extracted with ethyl acetate. The combined extracts were washed with water and brine, dried (Na$_2$SO$_4$), filtered, and concentrated. The concentrate was purified by flash column chromatography on silica gel with 95:5/hexanes:ethyl acetate to provide the desired product.

MS (ESI) 373 (M+H)$^+$.

EXAMPLE 129C 2,2-dimethyl-3-((4-phenoxyphenyl)sulfanyl)-1-propanol

A solution of Example 129B (4.2 g, 11.27 mmol) in THF (10 mL) was treated with acetic acid (20 mL) and H$_2$O (5 mL), heated at 45° C., stirred for 16 hours, cooled to 0° C., treated with saturated NaHCO$_3$ and extracted with ethyl acetate. The combined extracts were washed with brine, dried (Na$_2$SO$_4$), filtered, and concentrated. The concentrate was purified by flash column chromatography on silica gel with 5:1/hexanes:ethyl acetate to provide the desired product.

MS (DCI) 289 (M+H)$^+$.

EXAMPLE 129D 2,2-dimethyl-3-((4-phenoxyphenyl)sulfonyl)propyl (hydroxy)formamide The desired product was prepared by substituting Example 129C for Example 126C in Example 126D, then substituting the resulting product for Example 120A in Examples 120B–120D.

MS (ESI) 364 (M+H)$^+$;

$^1$H NMR (DMSO-d$_6$): δ 10.10 (bs, 0.5H), 9.68 (bs, 0.5H), 8.30 (s, 0.5H), 7.90–7.86 (m, 2.5H), 7.51–7.45 (m, 2H), 7.30–7.25 (m, 1H), 7.18–7.14 (m, 4H), 3.50 (s, 1H), 3.47 (s, 1H), 3.34 (s, 1H), 3.34 (s, 1H), 1.12 Anal. Calcd. for C$_{18}$H$_{21}$NO$_5$S: C, 59.49; H, 5.82; N, 3.85. Found: C, 59.37; H, 5.79; N, 3.69.

EXAMPLE 130

(1R)-3-((4-(4-chlorophenoxy)phenyl)sulfonyl)-1-((4,4-dimethyl-2,5-dioxo-1-imidazolidinyl)methyl) propyl)hydroxy)formamide The desired product was prepared by substituting 4-(4-chlorophenoxy)phenyl methyl sulfone for 4-phenoxyphenyl methyl sulfone in Example 123. 25 mp: 162–163° C.; (α)$_D^{25}$-2° (c 0.2, CHCl$_3$);

MS (ESI) 510 (M+H)$^+$;

$^1$H NMR (DMSO-d$_6$): δ 9.68 (bs, 0.5H), 9.38 (bs, 0.5H), 8.33 (bs, 0.5H), 8.27 (bs, 0.5H), 8.23 (s, 0.5H), 7.88–7.86 (m, 2H), 7.71 (s, 0.5H), 7.54–7.52 (m, 2H), 7.22–7.18 (m, 4H), 4.46–4.39 (m, 0.5H), 4.17–4.1- (m, 0.5H), 3.59–3.51 (m, 1H), 3.43–3.18 (m, 3H), 1.91–1.82 (m, 1H), 1.74–1.68 (m, 1H), 1.23–1.22 (m, 6H);

Anal. Calcd. for C$_{22}$H$_{24}$ClN$_3$O$_7$S: C, 51.82; H, 4.74; N, 8.24. Found: C, 51.86; H1 4.74; N, 8.21.

EXAMPLE 131

2,2-dimethyl-3-((4-(4-(trifluoromethoxy)phenoxy) phenyl)sulfonyl)propyl(hydroxy)formamide The desired product was prepared by substituting 4-(4-trifluoromethoxyphenoxy)benzenethiol for 4-phenoxybenzenethiol in Example 129.

MS (ESI) 448 (M+H)$^+$;

$^1$H NMR (DMSO-d): δ 9.75 (bs, 0.5H), 9.50 (bs, 0.5H), 8.31 (s, 0.5H), 7.93–7.88 (m, 2.5H), 7.50–7.47 (m, 2H), 7.32–7.21 (m, 4H), 3.50–3.47 (m, 2H), 3.34 (m, 2H), 1.12 (s, 6H).

EXAMPLE 132

(1R)-3-((4-(4-fluorophenoxy)phenyl)sulfonyl)-1-((3,4,4-trimethyl-2,5-dioxo-1-imidazolidinyl)methyl)propyl(hydroxy)formamide The desired product was prepared by substituting 4-(4-fluorophenoxy)phenyl methyl sulfone and 1,5,5-trimethylhydantoin for 4-phenoxyphenyl methyl sulfone and 5,5-dimethylhydantoin, respectively, in Example 123.

mp: 105° C. $(\alpha)_D^{25}$=+1.5(c=0.2, MeOH);
MS (ESI) 508 (M+H)$^+$;
$^1$H NMR (DMSO-d$_6$): δ 9.72 (s, 0.5H), 9.41 (s, 0.5H), 8.22 (s, 0.5H), 7.86–7.82 (m, 2H), 7.69 (s, 0.5H), 7.37–7.12 (m, 6H), 4.48–4.35 (m, 0.5H), 4.20–4.06 (m, 0.5H), 3.62–3.52 (m, 1H), 3.44–3.14 (m, 3H), 2.77 (s, 1.5H), 2.76 (s, 1.5H), 1.96–1.66 (m, 2H), 1.24–1.22 (m, 6H);
Anal. Calcd for: $C_{23}H_{26}N_3O_7SF.0.25\ H_2O$: C, 53.95; H, 5.21; N, 8.20. Found: C, 53.81; H, .5.42; N, 7.84.

EXAMPLE 133

(1R)-1-((4,4-dimethyl-2,5-dioxo-1-imidazolidinyl)methyl)-3-((4'-(trifluoromethyl)(1,1'-biphenyl)-4-yl)sulfonyl)propyl(hydroxy)formamide The desired product was prepared by substituting 4'-fluoro(1,1'-biphenyl)-4-yl methyl sulfone for 4-phenoxyphenyl methyl sulfone in Example 123.

mp: 125° C.; $(\alpha)_D^{25}$=+2.7 (c=0.6, MeOH);
MS (ESI) 528 (M+H)$^+$;
$^1$H NMR (DMSO-d$_6$): δ 9.72 (s, 0.5H), 9.42 (s, 0.5H), 8.36 (s, 0.5H), 8.29 (s, 0.5H), 8.24 (s, 0.5H), 8.07–7.97 (m, 6H), 7.91–7.88 (m, 2H), 7.71 (s, 0.5H), 4.52–4.40 (m, 0.5H), 4.22–4.09 (m, 0.55H), 3.60–3.50 (m, 4H), 1.98–1.64 (m, 2H), 1.20 (s, 3H), 1.19 (s, 3H);
Anal. Calcd for: $C_{23}H_{24}N_3O_6SF_3.0.25\ H_2O$ C, 51.92; H, 4.64; N, 7.89. Found: C, 51.58; H, 4.80; N, 7.76.

EXAMPLE 134

(±)-2-(((4-(4-fluorophenoxy)phenyl)sulfonyl)methyl)cyclohexyl(hydroxy)formamide

EXAMPLE 134A 2-(((4-fluorophenyl)sulfonyl)methyl)cyclohexanol

The desired product was prepared by substituting cyclohexene oxide and 4-fluorophenyl methyl sulfone for propylene oxide and 1-(methylsulfonyl)-4-phenoxybenzene, respectively, in Example 120A.

EXAMPLE 134B (1RS)-2-(((4-4-fluorophenoxy)phenyl)sulfonyl)methyl)cyclohexanol A solution of Example 134A (2.08 g, 7.6 mmol) in DMSO (25 mL) was added to a solution of 4-fluorophenol (1.29 g, 11 mmol) and potassium tert-butoxide (1.37 g, 12 mmol) in DMSO (25 mL). The mixture was heated to 120° C., stirred for 6 hours, cooled to room temperature, and partitioned between water and ethyl acetate. The organic phase was dried (MgSO$_4$), concentrated, and purified by flash column chromatography on silica gel with 9:1/ethyl acetate:dichloromethane to provide the desired product.

MS (ESI) 365 (M+H)$^+$.

EXAMPLE 134C (±)-2-(((4-(4-fluorophenoxy)phenyl) sulfonyl)methyl)cyclohexyl(hydroxy)formamide The desired product was prepared by substituting Example 134B for Example 120A in Examples 120B–120D.

MS (ESI) 408 (M+H)$^+$;
$^1$H NMR (DMSO-d$_6$): δ 9.96 (bs, 0.5H), 9.51 (bs, 0.5H), 8.05 (bs, 0.5H), 7.94–7.80 (m, 2.5H), 7.36–7.11 (m, 6H), 4.72–4.66 (m, 0.5H), 3.86–3.74 (m, 0.5H), 3.54–3.30 (m, 2H), 2.41–2.25 (m, 1H), 1.90–1.22 (m, 8H);
Anal. Calcd. for $C_{20}H_{22}FNO_5S$: C, 58.95; H, 5.44; N, 3.44. Found: C, 59.22; H, 5.77; N, 3.22.

EXAMPLE 135

Hydroxy((5-(((4-(4-(trifluoromethoxy)phenoxy)phenyl)sulfonyl)methyl)-1,3-dioxan-5-yl)methyl)formamide The desired product was prepared by substituting (5-(hydroxymethyl)-1,3-dioxan-5-yl)methanol and 4-(4-trifluoromethoxyphenoxy)benzenethiol for neopentyl glycol and 4-phenoxybenzenethiol, respectively, in Example 129.

MS (ESI) 492 (M+H)$^+$;
$^1$H NMR (DMSO-d$_6$): δ 9.90 (bs, 1H), 8.31 (s, 1H), 7.94–7.89 (m, 2H), 7.47 (d, 2H, J=9.3 Hz), 7.26 (dd, 4H, J=20.3, 8.9 Hz), 4.82–4.64 (m, 2H), 4.03–3.96 (m, 2H), 3.86 (s, 2H), 3.85–3.72 (m, 2H), 3.62–3.46 (m, 2H).
Anal. Calcd. for $C_{20}H_{20}F_3NO_8S$: C, 48.88; H, 4.10; N, 2.85. Found: C, 48.83; H, 4.12; N, 2.86.

What is claimed is:
1. A compound of formula (I),

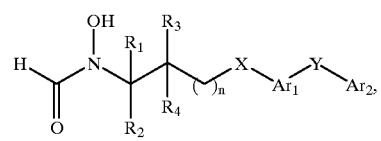

or a pharmaceutically acceptable salt or prodrug thereof, wherein
n is zero;
R$^1$ is hydrogen;
R$^2$ is selected from the group consisting of
hydrogen
and
-(alkylene)-NR$^6$R$^7$,
wherein
R$^6$ and R$^7$, taken together with the nitrogen atom to which they are attached,
R$^3$ and R$^4$ are independently selected from the group consisting of
hydrogen and
alkyl of one to six carbon atoms;
or
R$^4$ is hydrogen and R$^2$ and R$^3$, taken together with the carbon atoms to which they are attached, form a 6-membered saturated carbocyclic ring;
Ar$^1$ is phenyl, wherein the phenyl is unsubstituted;
X is
—CH$_2$SO$_2$—;
Y is selected from the group consisting of a covalent bond and
—O—; and Ar² is
   phenyl,
      wherein the phenyl can be optionally substituted with one substituent selected from the group consisting of
         halo and
         perfluoroalkoxy.

2. A compound according to claim 1 wherein R₃ and R₄ are alkyl of one to six carbon atoms.

3. A compound according to claim 2, wherein R₂ is hydrogen.

4. A compound according to claim 3 selected from the group consisting of
   2,2-dimethyl-3-((4-phenoxyphenyl)sulfonyl)propyl (hydroxy)formamide and
   2,2-dimethyl-3-((4-(4-(trifluoromethoxy)phenoxy)phenyl)sulfonyl)propyl(hydroxy)formamide.

5. A compound according to claim 1 wherein R² is -(alkylene)-NR⁶R⁷, wherein R⁶ and R⁷ taken together with the nitrogen atom to which they are attached, are

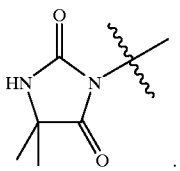

6. A compound according to claim 5 selected from the group consisting of
   (1R)-3-((4-(4-chlorophenoxy)phenyl)sulfonyl)-1-((4,4-dimethyl-2,5-dioxo-1-imidazolidinyl)methyl)propyl (hydroxy)formamide;
   (1R)-3-((4-(4-fluorophenoxy)phenyl)sulfonyl)-1-((3,4,4-trimethyl-2,5-dioxo-1-imidazolidinyl)methyl)propyl (hydroxy)formamide; and
   (1R)-1-((4,4-dimethyl-2,5-dioxo-1-imidazolidinyl)methyl)-3-((4'-(trifluoromethyl)(1,1'-biphenyl)-4-yl)sulfonyl)propyl(hydroxy)formamide.

7. A compound according to claim 1, wherein R₃ and R₄, taken together with the carbon atom to which they are attached form a dioxanyl ring.

8. A compound according to claim 7 which is hydroxy ((5-(((4-(4-(trifluoromethoxy)phenoxy)phenyl)sulfonyl)methyl)-1,3-dioxan-5-yl)methyl)formamide.

9. A compound according to claim 1 wherein R₁ and R₃, taken together with the carbon atoms to which they are attached, form a 6-membered carbocyclic ring.

10. A compound according to claim 9 which is (1RS)-2-(((4-(4-fluorophenoxy)phenyl)sulfonyl)methyl)cyclohexyl (hydroxy)-formamide.

11. A compound selected from the group consisting of 2,2-dimethyl-3-((4-phenoxyphenyl)sulfonyl)propyl (hydroxy)formamide;

(1R)-3-((4-(4-chlorophenoxy)phenyl)sulfonyl)-1-((4,4-dimethyl-2,5-dioxo-1-imidazolidinyl)methyl)propyl (hydroxy)formamide;

2,2-dimethyl-3-((4-(4-(trifluoromethoxy)phenoxy)phenyl)sulfonyl)propyl(hydroxy)formamide;

(1R)-3-((4-(4-fluorophenoxy)phenyl)sulfonyl)-1-((3,4,4-trimethyl-2,5-dioxo-1-imidazolidinyl)methyl)propyl (hydroxy)formamide;

(1R)-1-((4,4-dimethyl-2,5-dioxo-1-imidazolidinyl)methyl)-3-((4'-(trifluoromethyl)(1,1'-biphenyl)-4-yl)sulfonyl)propyl(hydroxy)formamide;

(1RS)-2-(((4-(4-fluorophenoxy)phenyl)sulfonyl)methyl)cyclohexyl(hydroxy)formamide; and hydroxy((5-(((4-(4-(trifluoromethoxy)phenoxy)phenyl)sulfonyl)methyl)-1,3-dioxan-5-yl)methyl)formamide.

12. A method for inhibiting matrix metalloproteinases in a mammal in need of such treatment, comprising administering to the mammal a therapeutically effective amount of a compound of claim 1.

13. A composition for inhibiting matrix metalloproteinases comprising a pharmaceutical carrier and a therapeutically effective amount of a compound of claim 1.

* * * * *